United States Patent
Knowlton

(10) Patent No.: US 9,149,322 B2
(45) Date of Patent: *Oct. 6, 2015

(54) METHOD FOR TREATMENT OF TISSUE

(76) Inventor: Edward Wells Knowlton, Zephyr Cove, NV (US)

(*) Notice: Subject to any disclaimer, the term of this patent is extended or adjusted under 35 U.S.C. 154(b) by 1352 days.

This patent is subject to a terminal disclaimer.

(21) Appl. No.: 10/828,703

(22) Filed: Apr. 21, 2004

(65) Prior Publication Data

US 2004/0210214 A1 Oct. 21, 2004

Related U.S. Application Data

(63) Continuation-in-part of application No. 10/813,980, filed on Mar. 31, 2004.

(60) Provisional application No. 60/459,219, filed on Mar. 31, 2003, provisional application No. 60/533,340, filed on Dec. 29, 2003.

(51) Int. Cl.
| A61B 18/18 | (2006.01) |
| A61B 18/14 | (2006.01) |
| A61B 18/20 | (2006.01) |
| A61B 17/00 | (2006.01) |
| A61B 18/00 | (2006.01) |

(52) U.S. Cl.
CPC .............. *A61B 18/14* (2013.01); *A61B 18/203* (2013.01); *A61B 2017/00747* (2013.01); *A61B 2017/00792* (2013.01); *A61B 2018/00005* (2013.01); *A61B 2018/00452* (2013.01); *A61B 2018/00702* (2013.01); *A61B 2018/00791* (2013.01); *A61B 2018/00875* (2013.01); *A61M 2202/08* (2013.01)

(58) Field of Classification Search
CPC . A61B 18/18; A61B 18/1815; A61B 18/1492
USPC .......... 606/27–34, 44–52, 41; 607/96, 101–2, 607/104, 98–102
See application file for complete search history.

(56) References Cited

U.S. PATENT DOCUMENTS

| 6,350,276 B1 * | 2/2002 | Knowlton | 607/104 |
| 6,377,854 B1 * | 4/2002 | Knowlton | 607/101 |
| 6,470,216 B1 * | 10/2002 | Knowlton | 607/101 |

* cited by examiner

*Primary Examiner* — Aaron Roane
(74) *Attorney, Agent, or Firm* — IPR Law Group, PC

(57) ABSTRACT

An embodiment of the invention provides a method of treating a target tissue site method comprising selecting the tissue site based on a tissue profile or condition of the tissue site; delivering energy to the tissue site at a first depth to achieve a first tissue effect using an energy delivery device; delivering energy to the tissue site at a second depth to achieve a second tissue effect using an energy delivery device; and remodeling at least a portion of tissue at the tissue site.

35 Claims, 54 Drawing Sheets

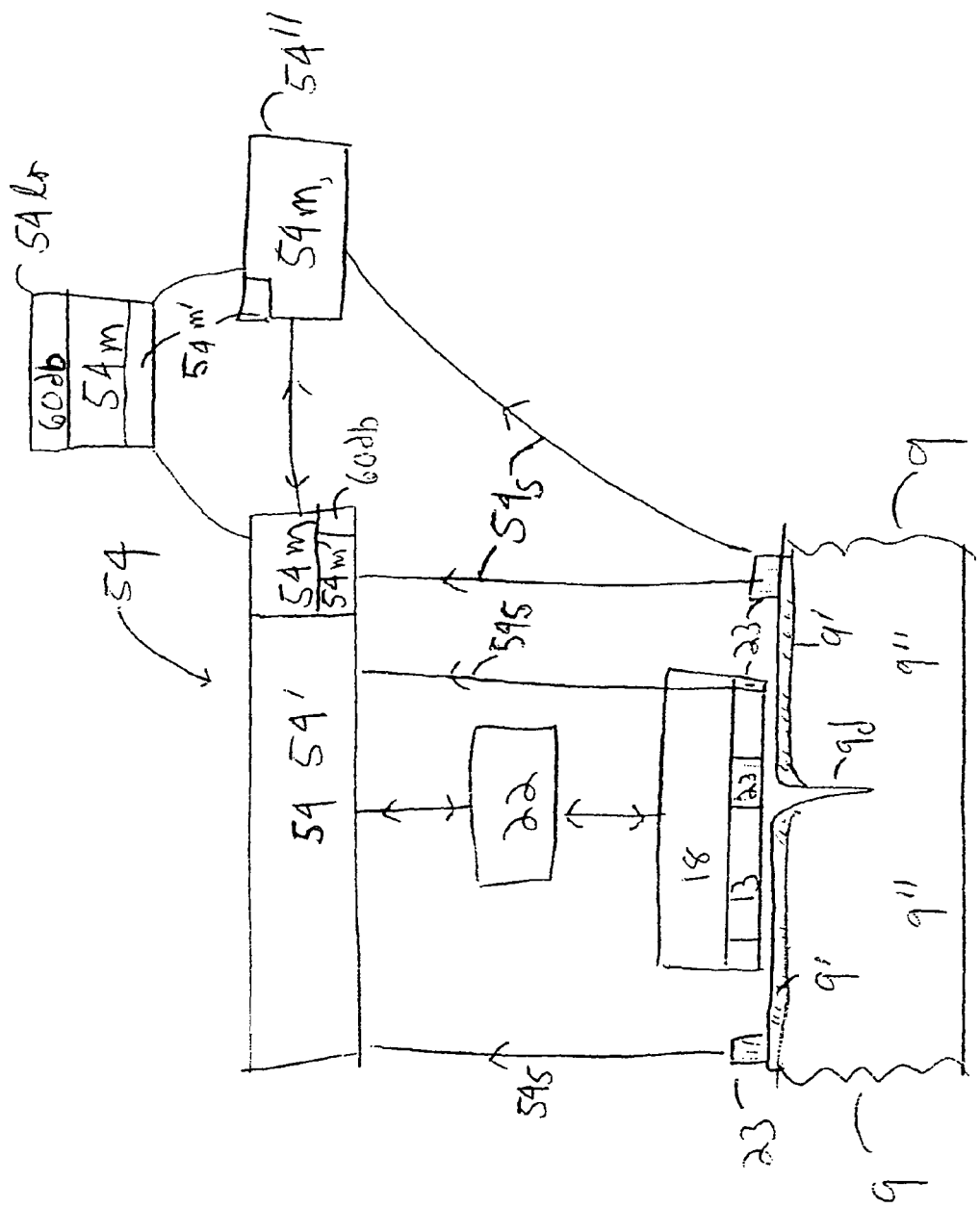

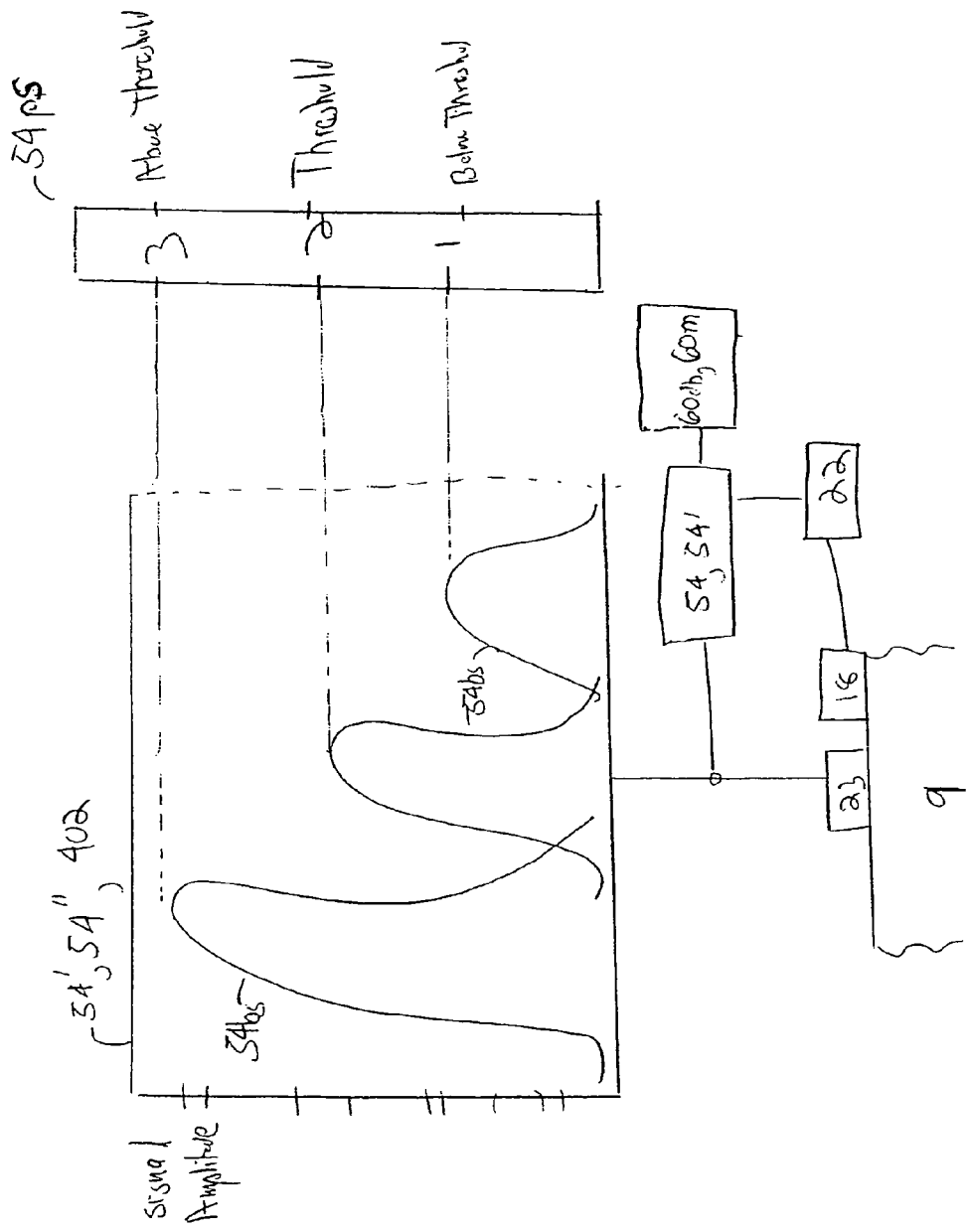

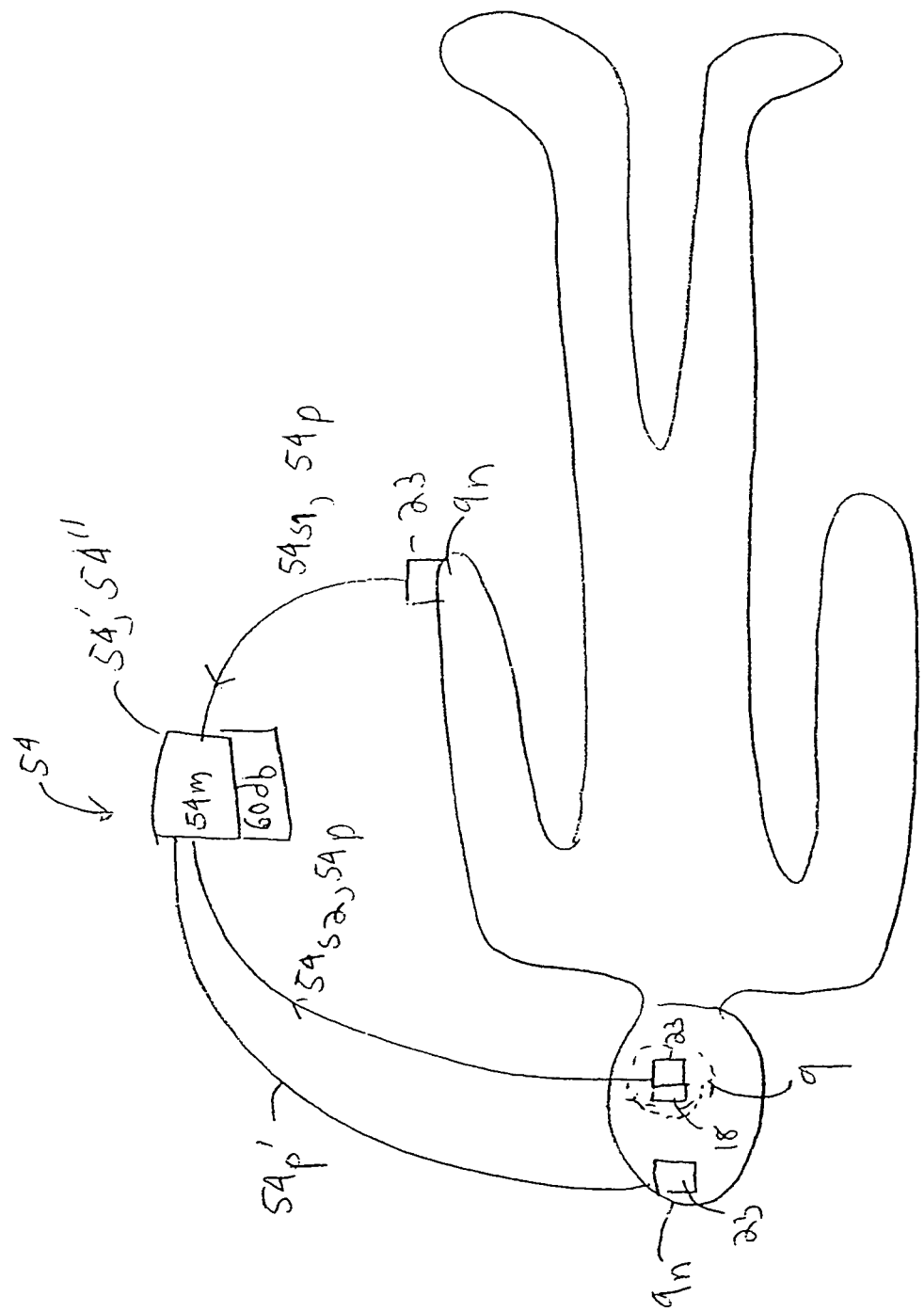

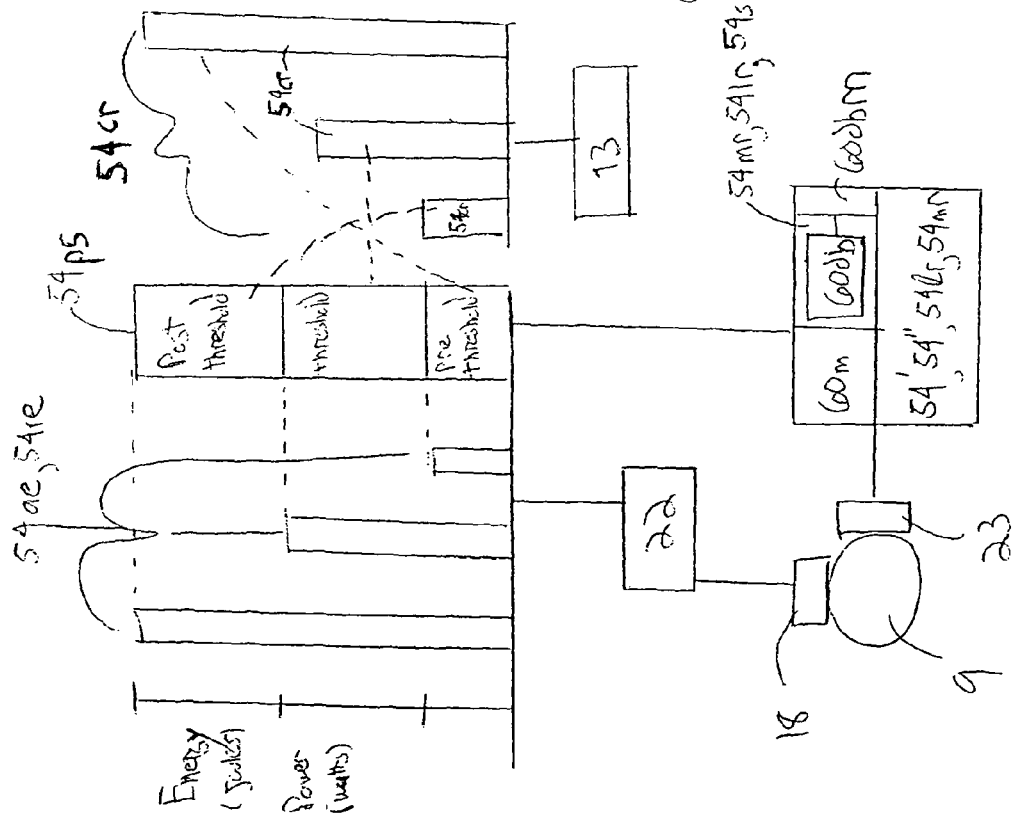

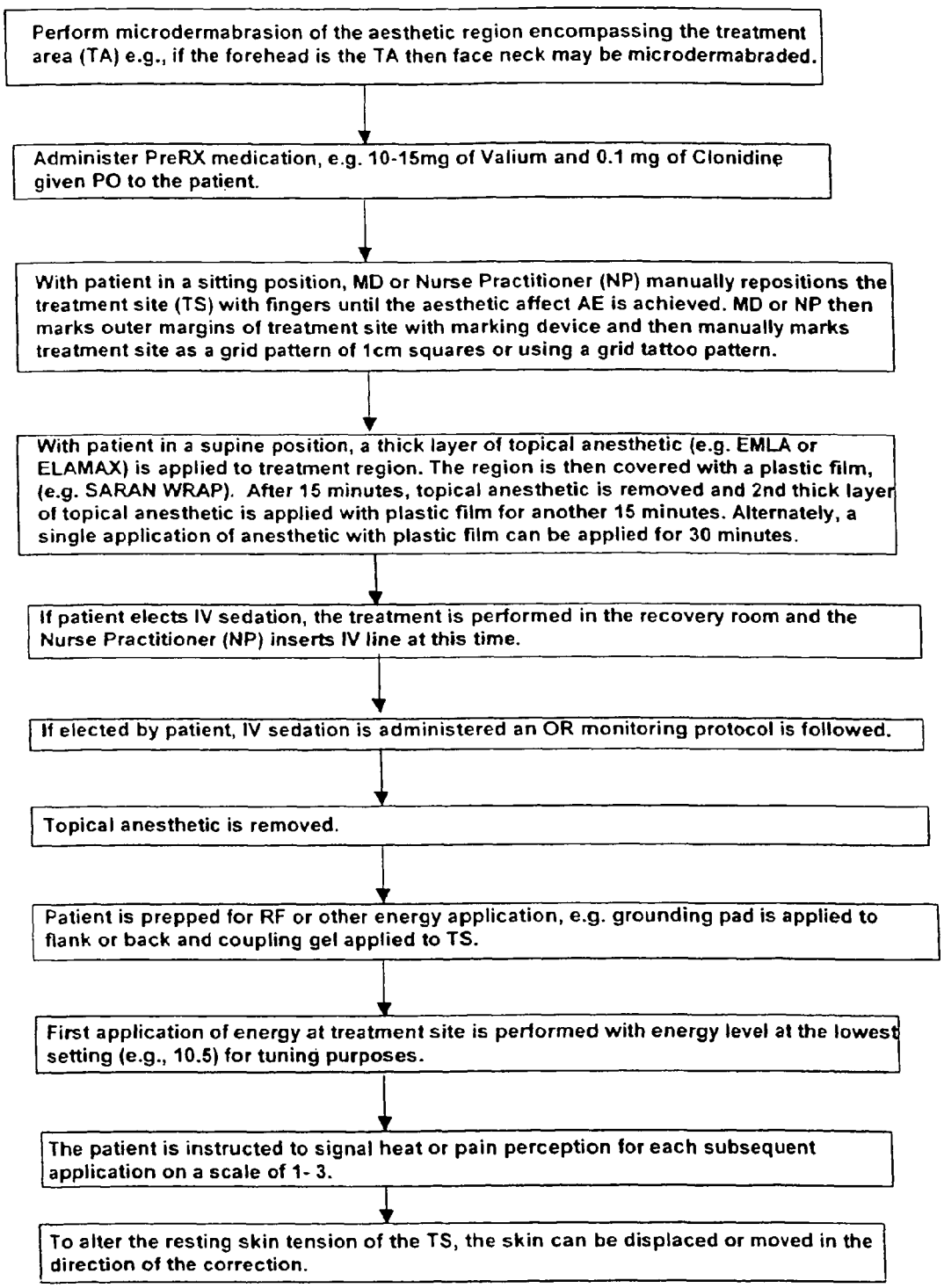
FIG. 30 Patient Treatment Algorithm Using A Topical Anesthetic

FIG. 30 Patient Treatment Algorithm, Continued

The next energy application can be started at energy level 11.0 and is applied to an adjacent grid site (all subsequent applications are applied to new adjacent grid sites). A ramp-up titration method can be used by increasing the energy level by 1 with each subsequent application until a perceived heat level of 2 is signaled by the patient. Subsequent applications can continue at that energy level until additional titration is needed because of a change in the perceived heat level by the patient. Those previous grid sites that were perceived as heat level 1 are marked with a dot in the center for re-treatment after the grid pattern is completed. Grid sites that do not exhibit erythema can also be retreated even though the patient previously signaled a level 2 at these sites.

↓

If a heat level 3 is perceived by the patient, the energy level is reset one level lower until a heat level 2 is perceived by the patient. Subsequent applications can continue at that energy level until additional titration is needed because of a change in perceived heat level by the patient. No retreatment is needed for sites that are perceived at heat level 3.

↓

Additional Passes: For under corrected areas, subsequent applications are administered to portions of a treatment site that was previously signaled as heat level 2.

↓

Post treatment stenting of the treatment site can be performed to reduce resting skin tension and preserve primary dermal collagen contraction and also assist in secondary wound healing contraction. For example, the application of RESTON at the inferior of the breast coupled with wearing of a supportive bra may initially preserve and secondarily increase the elevation of the nipple areolar complex in breast ptosis patients.

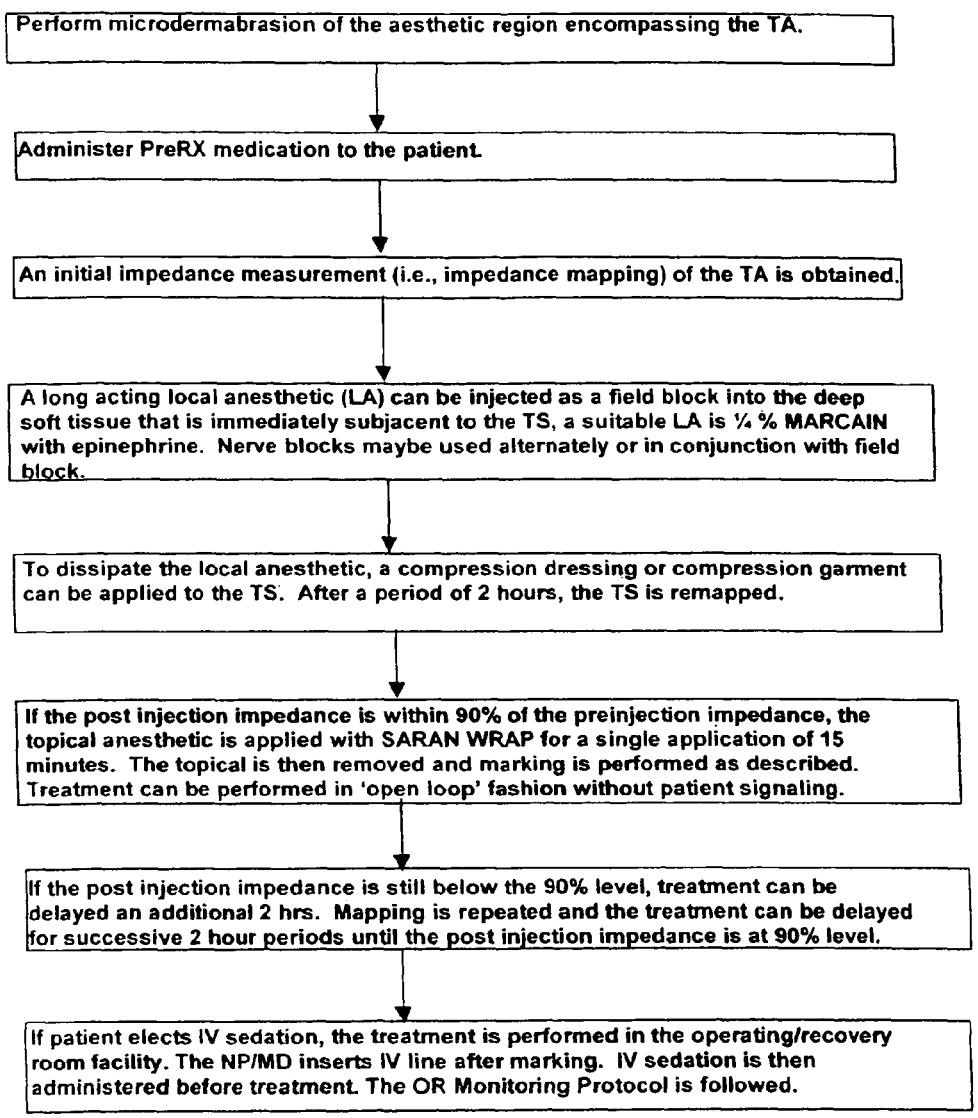
FIG. 31 Patient Treatment Algorithm Using An Injected Local Anesthetic

FIG. 32 Photographic/Visual Documentation Algorithm
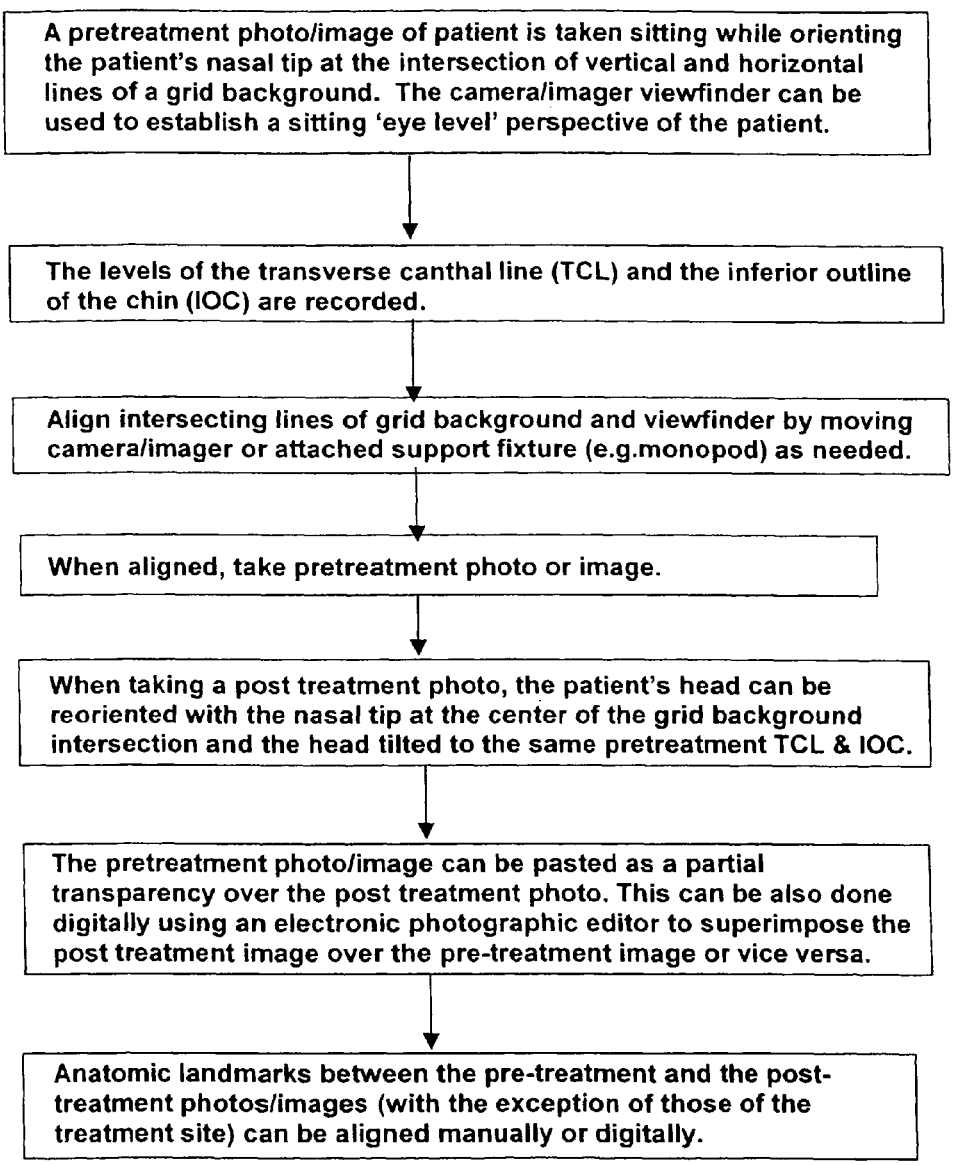

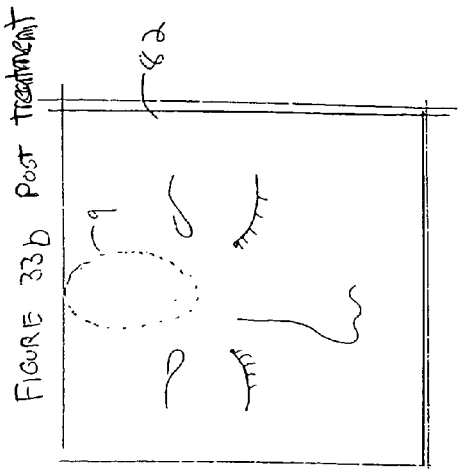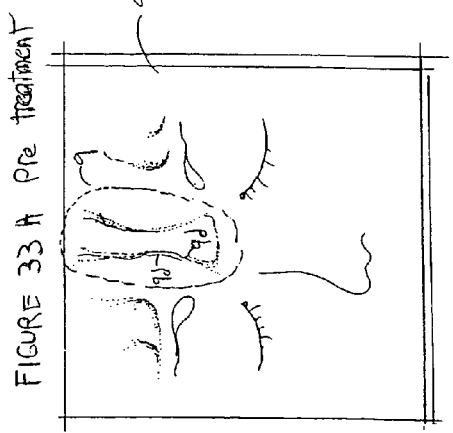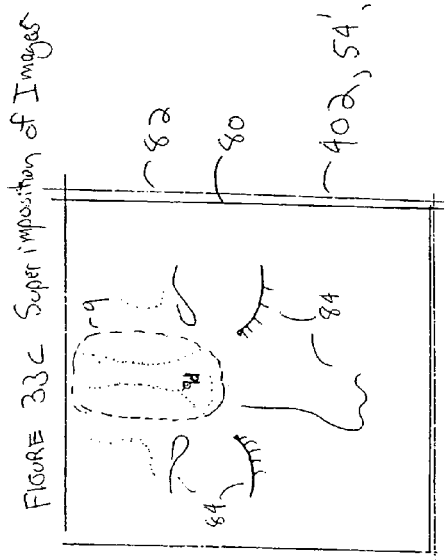

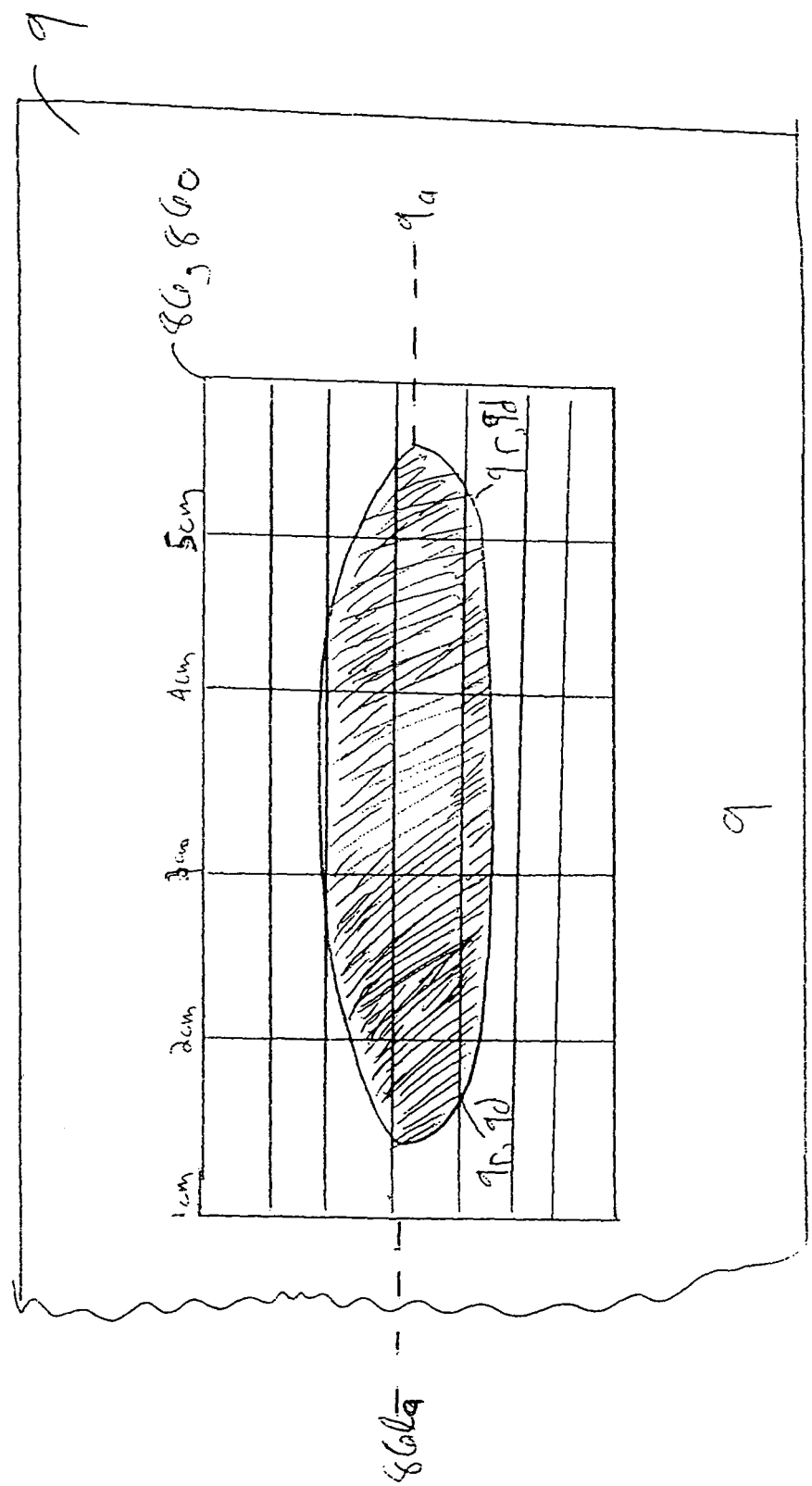

Without Vectored Thermoplasty where only compression is applied, the thermal adhesion is created at the single arrow, 90

With Vectored Thermoplasty where compression and tangential forces are applied, the thermal adhesion of the tissue is created at the double arrow, 91 in a more aesthetically corrected configuration.

Typical Facelift Incision, 500

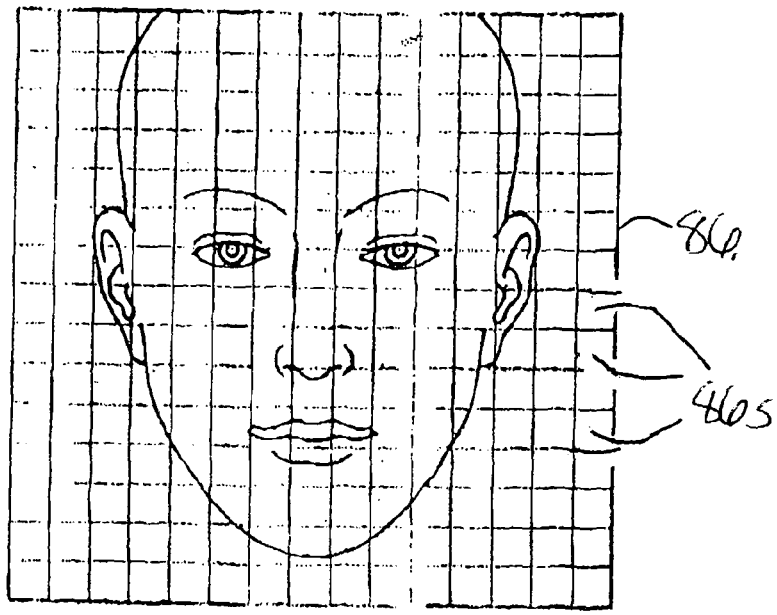
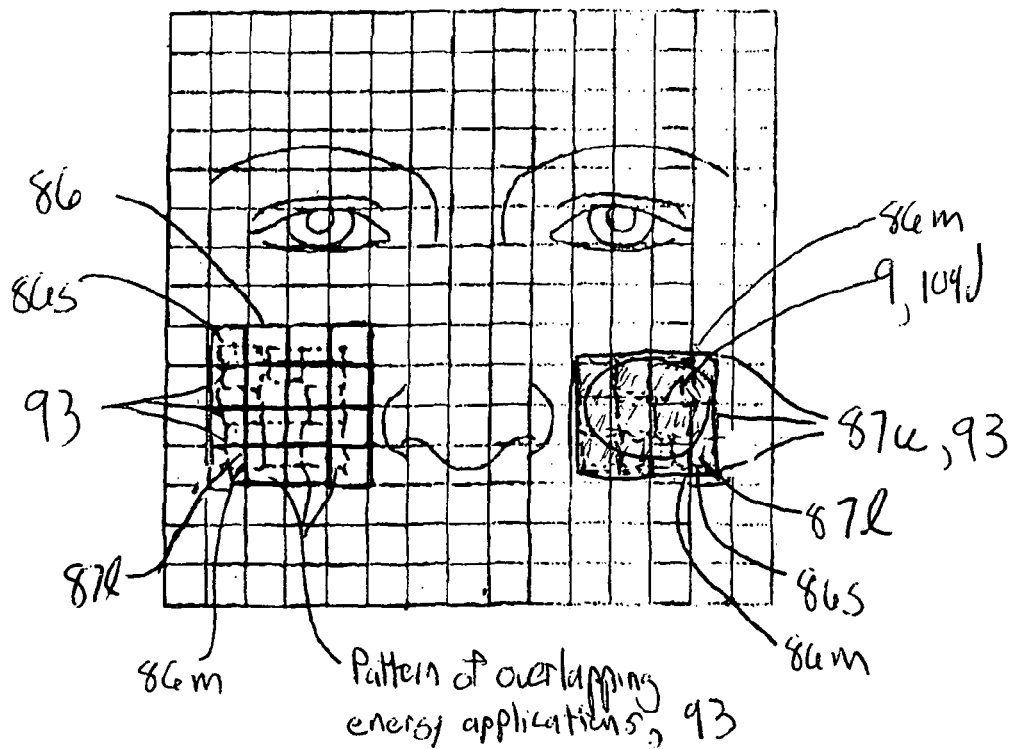

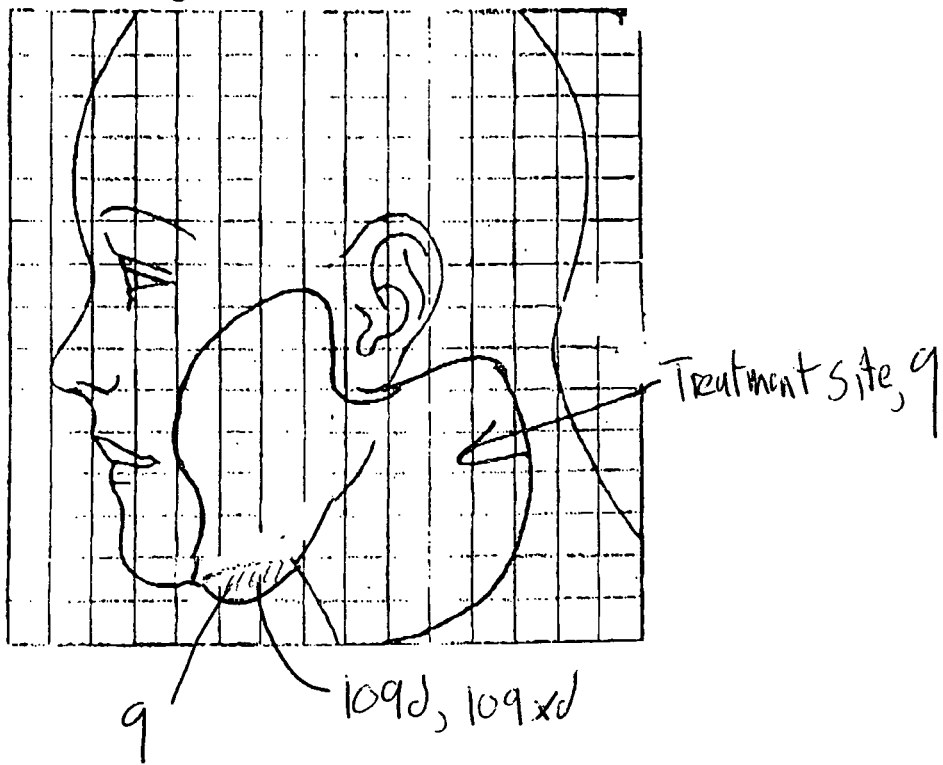
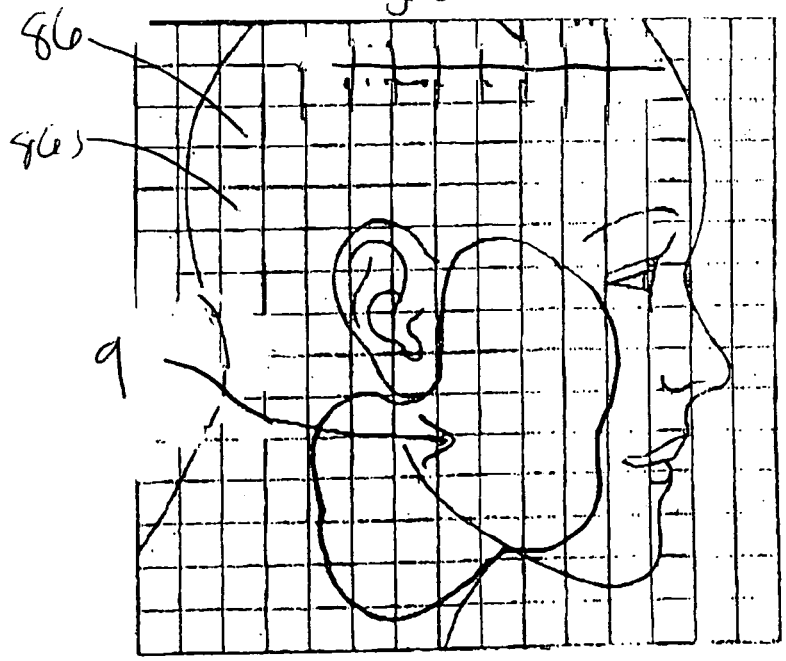

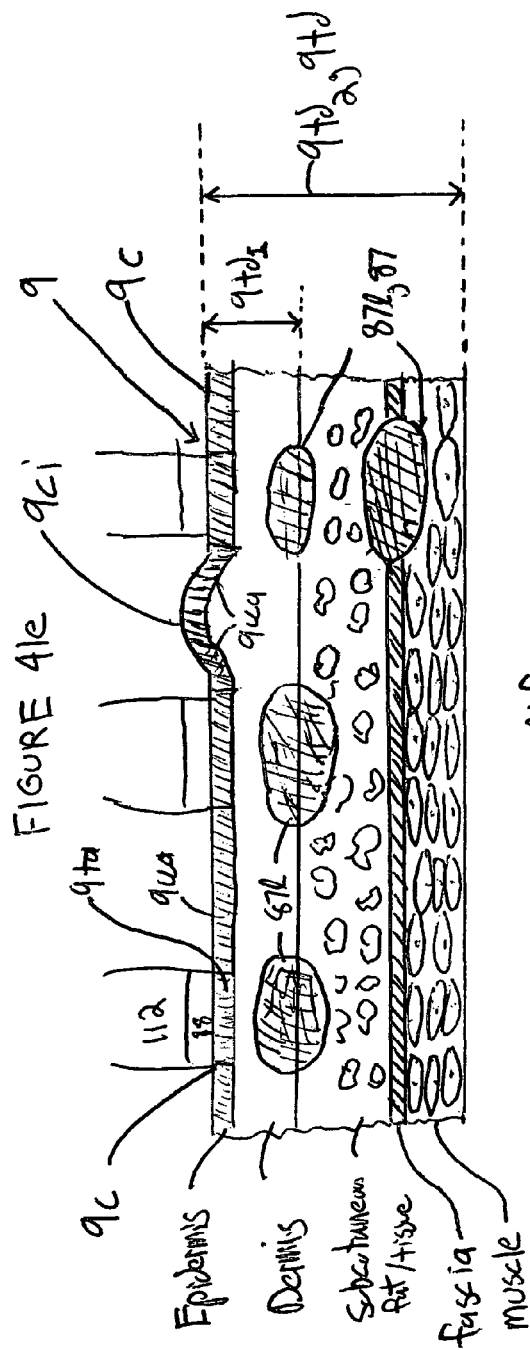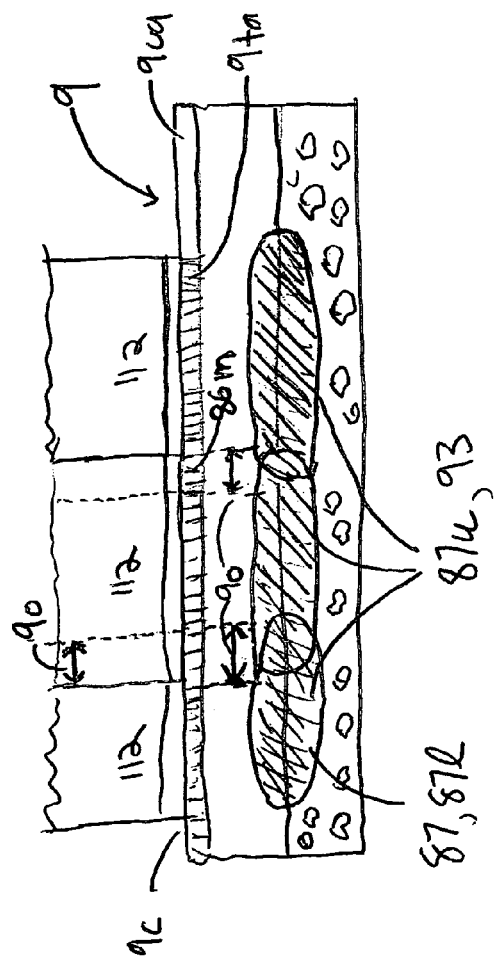

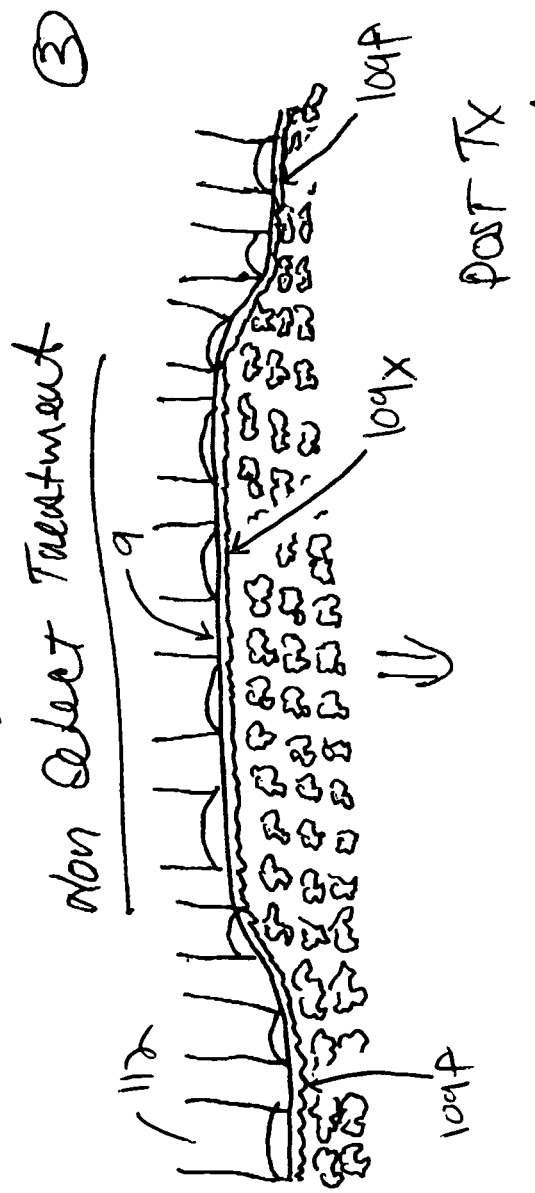
Figure 43A — Non Ulcer Treatment
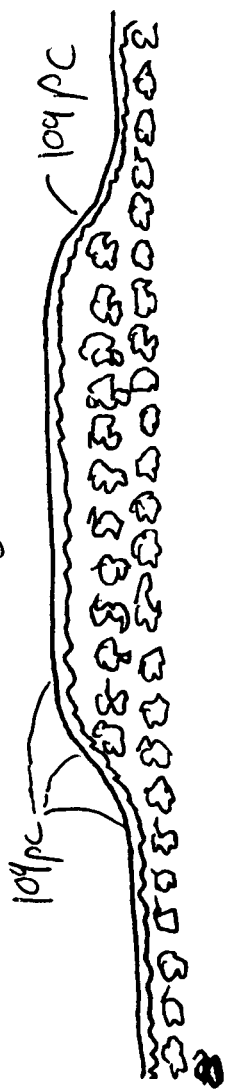
Figure 43b — Post TX Ulcer+

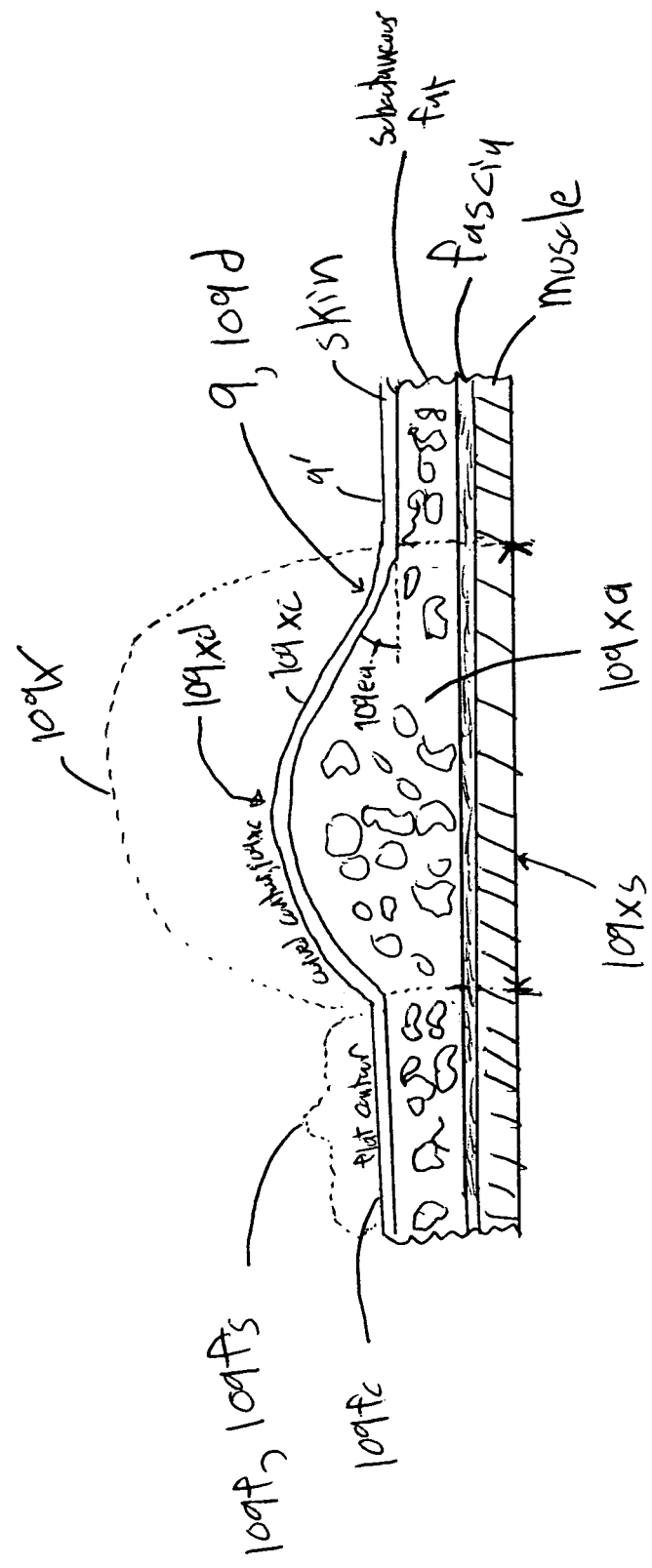

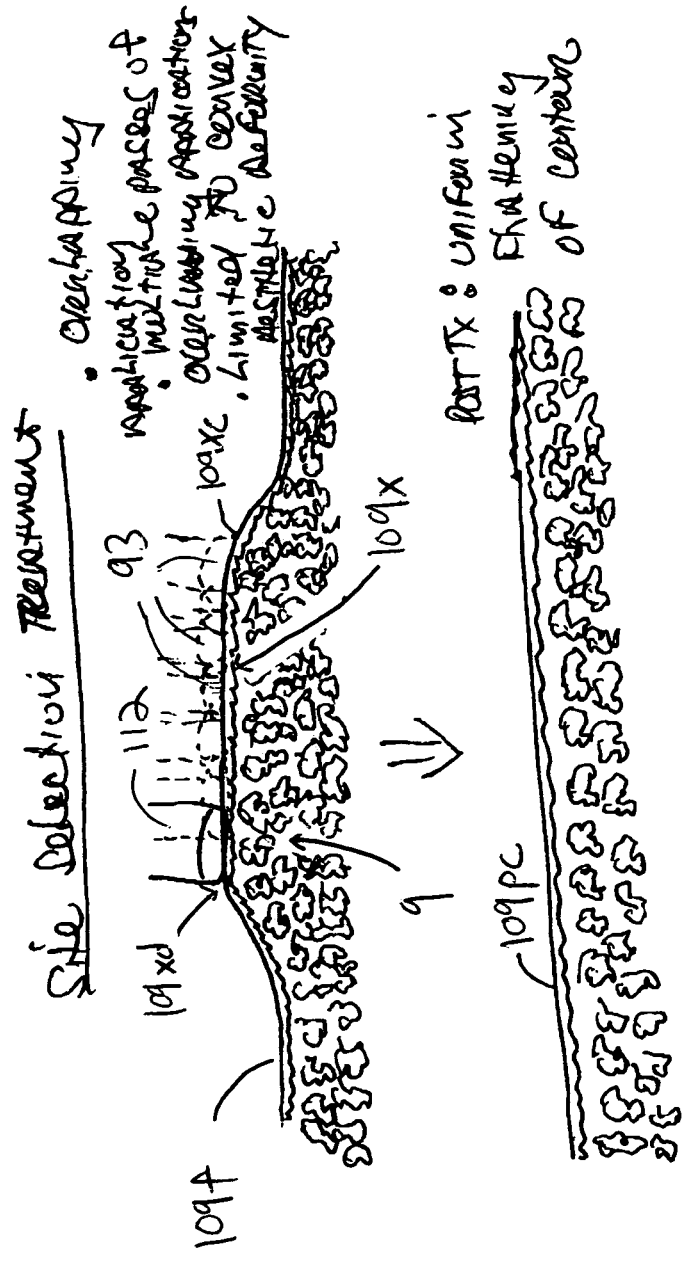

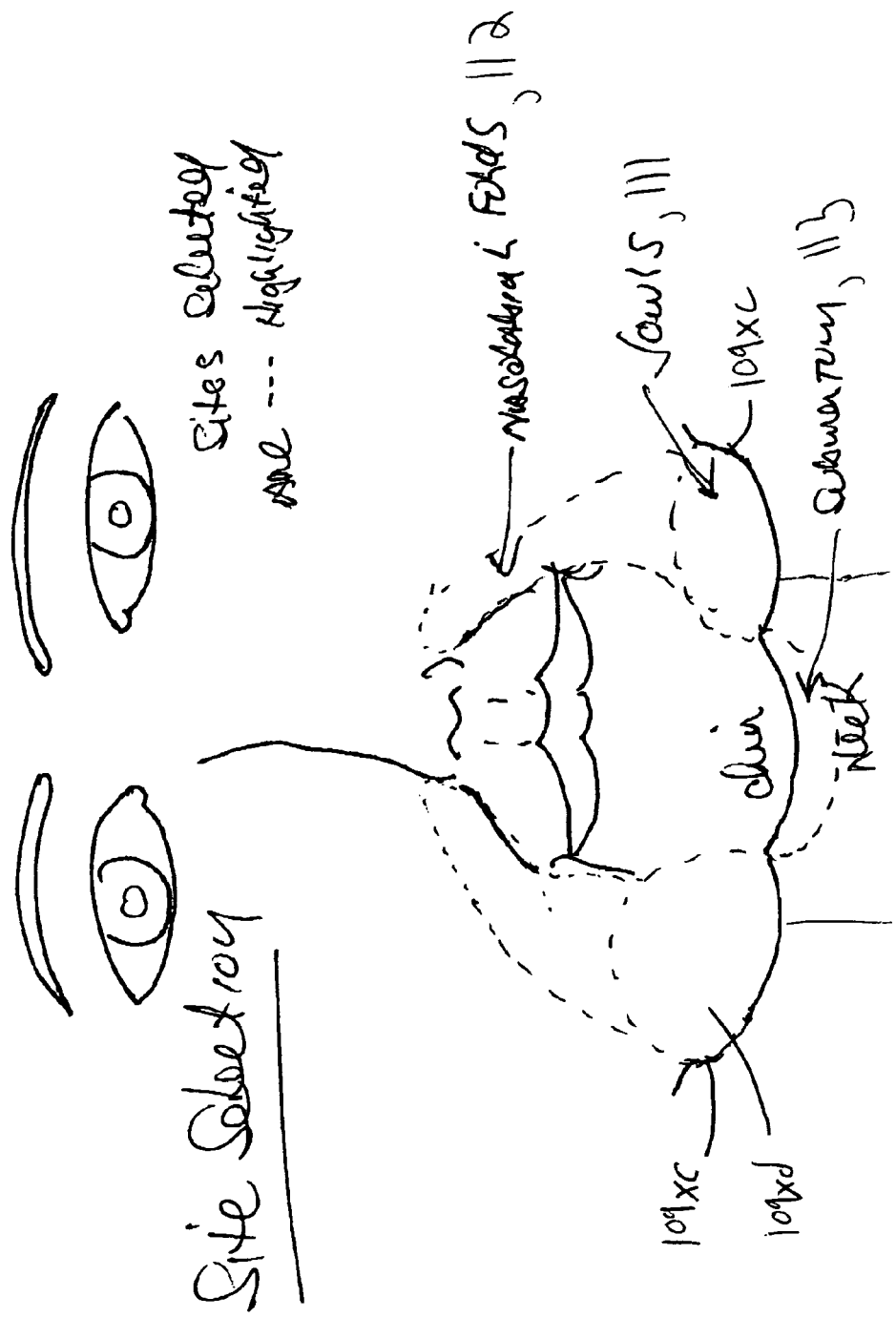

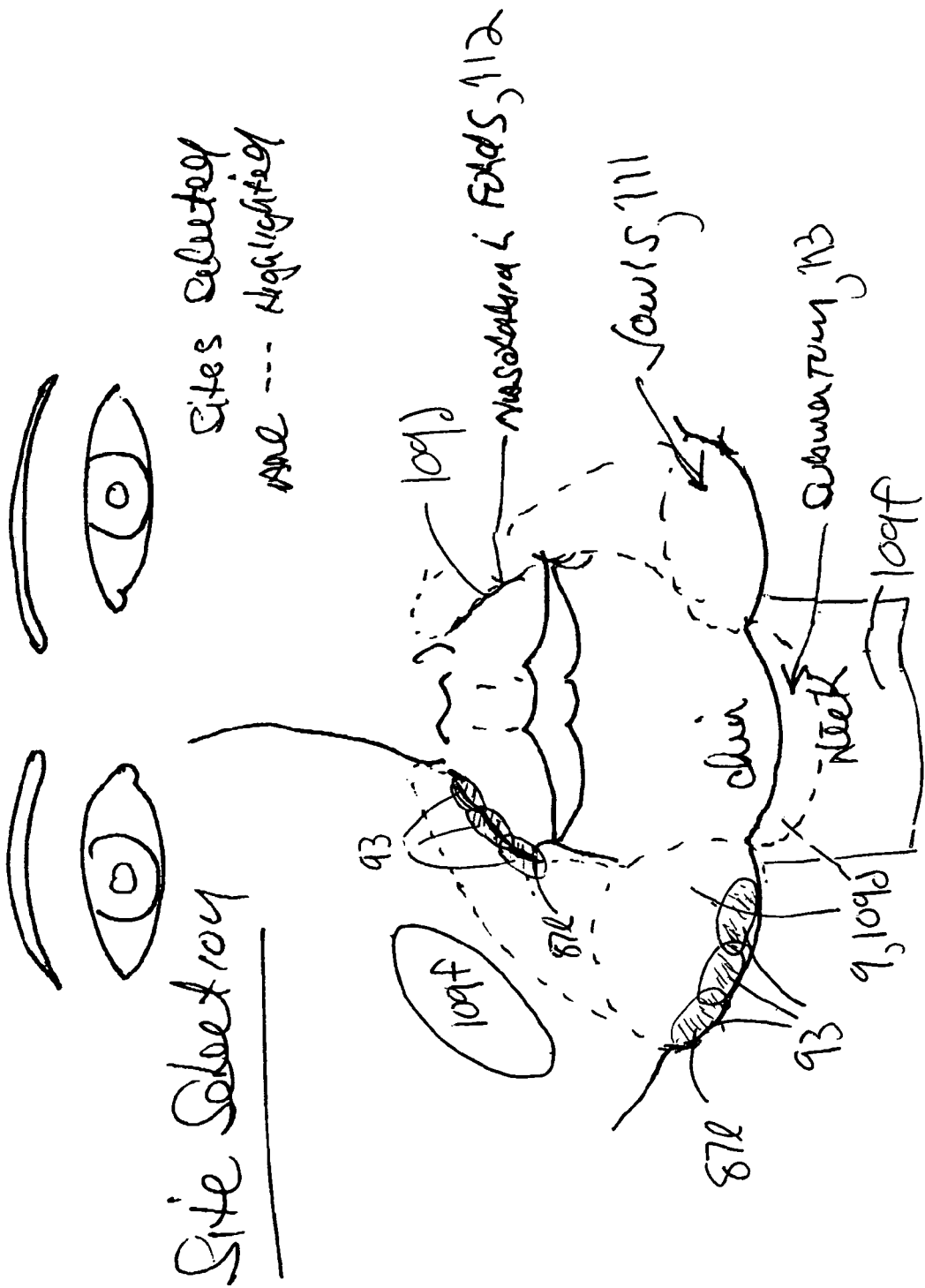

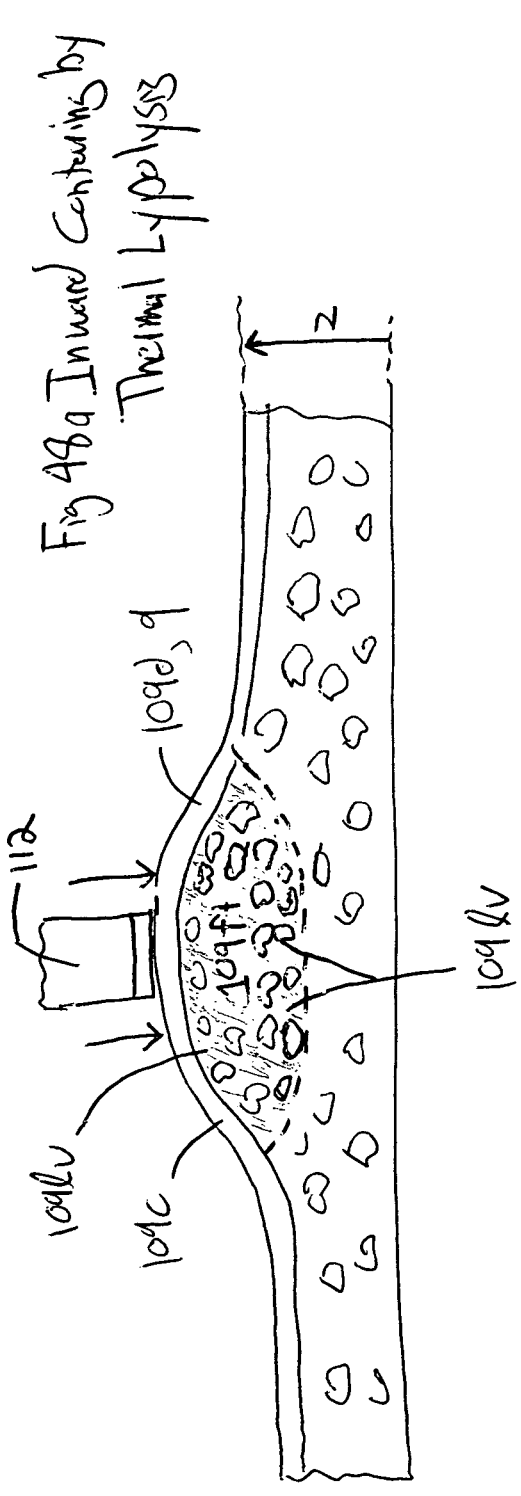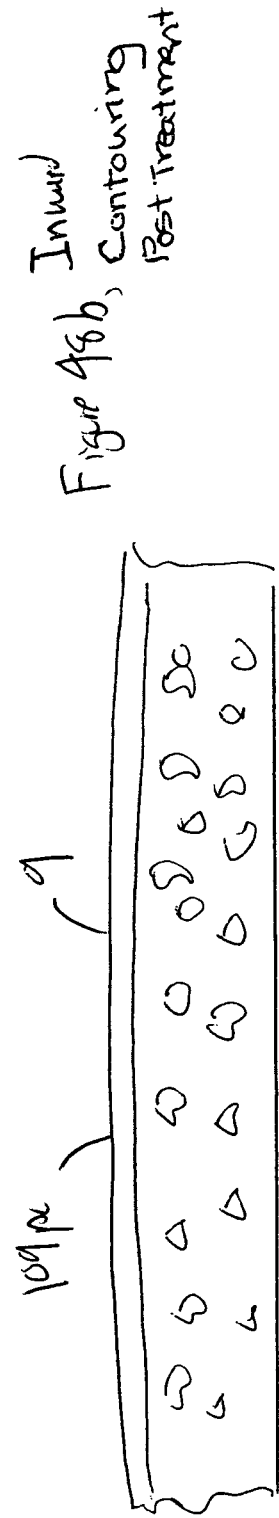

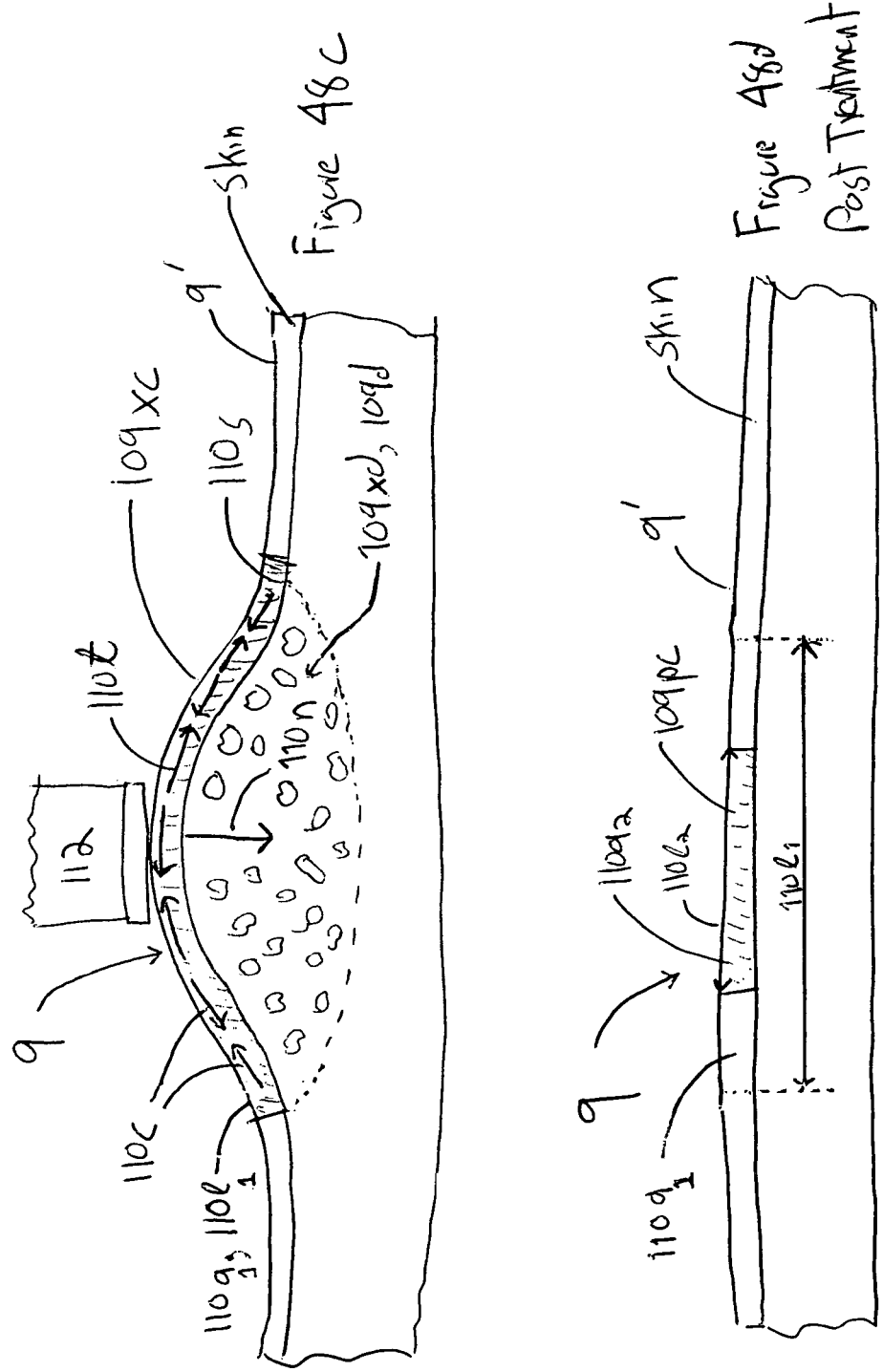

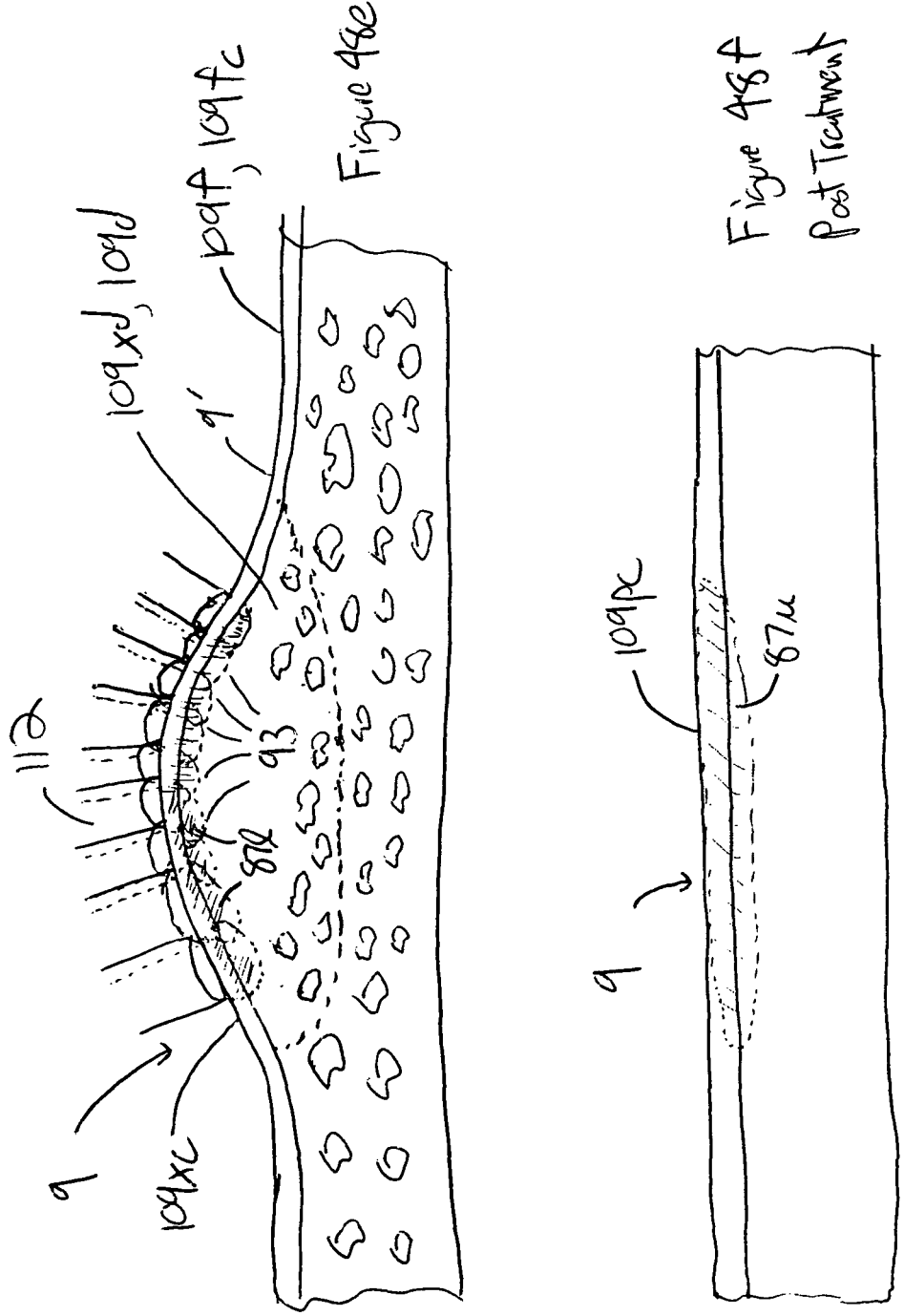

METHOD FOR TREATMENT OF TISSUE

RELATED APPLICATIONS

This application is a continuation-in-part of U.S. patent application Ser. No. 10/813,980, filed Mar. 31, 2004, entitled "Method for Treatment of Tissue" which claims the benefit of priority to U.S. Provisional Application Ser. No. 60/459,219, filed Mar. 31, 2003, entitled "Method for Treatment of Tissue Using Vectored Force", and U.S. Provisional Application Ser. No. 60/533,340, filed Dec. 29, 2003, entitled "Method For Treatment Of Tissue Using Force And Energy", each application being fully incorporated by reference herein.

TECHNICAL FIELD

The disclosed embodiments relate to a method for treating tissue using the delivery of force and/or energy.

BACKGROUND

The human skin is composed of two elements: the epidermis and the underlying dermis. The epidermis with the stratum corneum serves as a biological barrier to the environment. The underlying dermis provides the main structural support of the skin. It is composed mainly of an extracellular protein called collagen. Collagen is produced by fibroblasts and synthesized as a triple helix with three polypeptide chains that are connected with heat labile and heat stable chemical bonds. When collagen-containing tissue is heated, alterations in the physical properties of this protein matrix occur at a characteristic temperature. The structural transition of collagen contraction occurs at a specific "shrinkage" temperature. The shrinkage and remodeling of the collagen matrix with heat is the basis for the technology.

Collagen crosslinks are either intramolecular (covalent or hydrogen bond) or intermolecular (covalent or ionic bonds). The thermal cleavage of intramolecular hydrogen crosslinks is a scalar process that is created by the balance between cleavage events and relaxation events (reforming of hydrogen bonds). No external force is required for this process to occur. As a result, intermolecular stress is created by the thermal cleavage of intramolecular hydrogen bonds. Essentially, the contraction of the tertiary structure of the molecule creates the initial intermolecular vector of contraction.

Collagen fibrils in a matrix exhibit a variety of spatial orientations. The matrix is lengthened if the sun of all vectors acts to distract the fibril. Contraction of the matrix is facilitated if the sum of all extrinsic vectors acts to shorten the fibril. Thermal disruption of intramolecular hydrogen bonds and mechanical cleavage of intermolecular crosslinks is also effected by relaxation events that restore preexisting configurations. However, a permanent change of molecular length will occur if crosslinks are reformed after lengthening or contraction of the collagen fibril. The continuous application of an external mechanical force will increase the probability of crosslinks forming after lengthening or contraction of the fibril.

Hydrogen bond cleavage is a quantum mechanical event that requires a threshold of energy. The amount of (intramolecular) hydrogen bond cleavage required corresponds to the combined ionic and covalent intermolecular bond strengths within the collagen fibril. Until this threshold is reached, little or no change in the quaternary structure of the collagen fibril will occur. When the intermolecular stress is adequate, cleavage of the ionic and covalent bonds will occur. Typically, the intermolecular cleavage of ionic and covalent bonds will occur with a ratcheting effect from the realignment of polar and non-polar regions in the lengthened or contracted fibril.

Cleavage of collagen bonds also occurs at lower temperatures but at a lower frequency. Low-level thermal cleavage is frequently associated with relaxation phenomena in which bonds are reformed without a net change in molecular length. An external force that mechanically cleaves the fibril can reduce the probability of relaxation phenomena and provides a means to lengthen or contract the collagen matrix at lower temperatures while reducing the potential of surface ablation.

Soft tissue remodeling is a biophysical phenomenon that occurs at cellular and molecular levels. Molecular contraction or partial denaturization of collagen involves the application of an energy source, which destabilizes the longitudinal axis of the molecule by cleaving the heat labile bonds of the triple helix. As a result, stress is created to break the intermolecular bonds of the matrix. This is essentially an immediate extracellular process, whereas cellular contraction can require a lag period for the migration and multiplication of fibroblasts into the wound as provided by the wound healing sequence. In higher developed animal species, the wound healing response to injury involves an initial inflammatory process that subsequently leads to the deposition of scar tissue.

The initial inflammatory response consists of the infiltration by white blood cells or leukocytes that dispose of cellular debris. Seventy-two hours later, proliferation of fibroblasts at the injured site occurs. These cells differentiate into contractile myofibroblasts, which are the source of cellular soft tissue contraction. Following cellular contraction, collagen is laid down as a static supporting matrix in the tightened soft tissue structure. The deposition and subsequent remodeling of this nascent scar matrix provides the means to alter the consistency and geometry of soft tissue for aesthetic purposes.

In light of the preceding discussion, there are a number of dermatological procedures, which may lend themselves to treatments which deliver thermal energy to the skin and underlying tissue to cause a contraction of collagen, and/or initiate a wound healing response at or near the treatment site. There is a need for systems and methods utilizing patient feedback to control the delivery of energy in such procedures and treatments.

SUMMARY OF THE INVENTION

Embodiments of the invention provide a method and apparatus for treating the skin using energy and vectored application of force to reposition the skin or other selected tissue portion, secure the repositioned skin in place using thermal adhesions or lesions and produce collagen contraction and/or a wound healing within the tissue site to produce a desired amount of tissue remodeling, tightening and/or rejuvenation. In use, these embodiments allow for an improved aesthetic outcome in tissue remodeling procedures such as face lifts, eyebrow lifts and liposuction of the face, thighs, buttocks and stomach by producing substantially uniform amounts of skin tightening and/or controlled release or severing of the fibrous septae. Specific embodiments can also include a combination of energy and force delivery with liposuction and related plastic surgery procedures using a port incision or other minimally invasive surgical methods known in the art. Other embodiments can also include a site selection step based on the degree of convexity of an aesthetic deformity.

An embodiment of the invention provides a method of treating a target tissue site, the method comprising selecting the tissue site based on a tissue profile or condition of the tissue site; delivering energy to the tissue site at a first depth to achieve a first tissue effect using an energy delivery device;

delivering energy to the tissue site at a second depth to achieve a second tissue effect using an energy delivery device; and remodeling at least a portion of tissue at the tissue site.

Another embodiment of the invention provides a method for treating a tissue site comprising delivering energy to the tissue site using an energy delivery device; delivering a vectored mechanical force to the tissue site; producing a thermal adhesion or lesion at the tissue site and remodeling at least a portion of tissue at the tissue site. In related embodiments, the delivery of force can be vectored responsive to one of an energy delivery parameter, a tissue property or patient feedback. Other related embodiments can include the performance of a liposuction procedure substantially at the tissue site. Still other related embodiments can include skeletonizing at least a portion of fibrous septae at the tissue site. In another related embodiment, the thermal adhesion can include a plurality of thermal adhesions wherein the plurality of adhesions is substantially continuous or uniform in thickness or other dimension.

Yet another embodiment provides a method of treating a target tissue site, comprising delivering energy to the tissue site using an energy delivery device; delivering a vectored mechanical force to the tissue site; producing a thermal adhesion or lesion at the tissue site; and remodeling at least a portion of tissue at the tissue site utilizing the thermal adhesion or lesion.

Still another embodiment provides a method of energetically treating a target tissue comprising delivering a thermal dose to a tissue site using substantially overlapping applications of energy from an energy delivery device; producing a substantially uniform thermal lesion at the tissue site; and remodeling at least portion of tissue at the tissue site while minimizing aesthetic discontinuities or irregularities in the remodeled portion. The thermal dose is sufficient to cause at least one of tissue tightening, collagen contraction or remodeling of at least a portion tissue at the target site.

Other embodiments of the invention provide a method and apparatus whereby energy is delivered to a tissue site to heat tissue to cause a contraction of collagen, and/or initiate a would healing response to reshape, tighten or rejuvenate tissue at the tissue site, wherein patient feedback is utilized to reduce the thermal injury to non target tissue and/or the patient's level of pain or discomfort resulting from the delivery of energy to the tissue site.

Still another embodiment provides a method whereby electromagnetic energy is delivered to a tissue site and the surface of the tissue site is cooled using a heat transfer fluid whereby a reverse thermal gradient is achieved within the tissue site sufficient to produce collagen contraction and/or a subsequent wound healing response within the tissue site. Patient feedback is utilized to control one of the energy delivery or cooling rate to reduce an amount of pain or thermal injury to the surface of the tissue site or non-target adjacent tissue.

Yet another embodiment provides a method whereby RF energy is topically delivered to a tissue site using an energy delivery device and the surface of the tissue site is cooled using a cooling or cryogenic fluid whereby a reverse thermal gradient is achieved within the tissue site sufficient to produce collagen contraction and/or a subsequent wound healing response within the tissue site. Patient feedback is utilized to control one of the energy delivery or cooling rate to reduce an amount of pain or thermal injury to the surface of the tissue site or non-target adjacent tissue.

Another embodiment provides a method whereby RF energy is topically delivered to a tissue site to produce collagen contraction and/or a subsequent wound healing response within the tissue site. Patient feedback is utilized to control the energy delivery to reduce an amount of pain or thermal injury to the surface of the tissue site or non-target adjacent tissue.

Yet another embodiment provides a method wherein patient feedback is used to titrate the delivery of energy to a target tissue site to produce heating of the subjacent dermis to contract a tissue collagen matrix within or adjacent the target tissue site.

Still yet another embodiment provides a method wherein patient feedback and a feedback module or processor are used to titrate the delivery of energy to a target tissue site to produce heating of the subjacent dermis to contract a tissue collagen matrix.

Another embodiment provides a method whereby energy is topically delivered produce heating of the subjacent dermis to contract a tissue collagen matrix and patient feedback is utilized to facilitate preservation of the epidermis.

Yet another embodiment provides a method whereby energy is topically delivered to produce heating of the subjacent soft tissue such as the subcutaneous fat layer, muscle fascia and muscle and to contract a tissue collagen matrix of the subjacent soft tissue, wherein patient feedback is utilized to facilitate preservation of the epidermis.

Still yet another embodiment provides a method whereby energy is topically delivered to produce heating of the subjacent soft tissue such as the subcutaneous fat layer to cause thermal lipolysis and patient feedback is utilized to optimize or increase lipolysis while substantially preserving or reducing injury to the epidermis or other skin layer.

Another embodiment provides a method whereby energy is topically delivered to produce heating of the subjacent dermis to contract a tissue collagen matrix to produce an amount of skin tightening and patient feedback is utilized to facilitate preservation of the epidermis or reduce an amount of epidermal injury or erythema.

Yet another embodiment provides a method whereby energy is delivered to a tissue site to heat tissue to cause a contraction of collagen and/or initiate a wound healing response, and patient feedback is utilized to reduce the thermal injury to non target tissue and/or the patient's level of pain or discomfort resulting from the delivery of energy to the tissue site.

Still yet another embodiment provides a method whereby energy is delivered to a tissue site to heat tissue to cause a contraction of collagen and/or initiate a would healing response, and patient feedback in the form of a patient determined pain/thermal sensation scale is utilized to reduce the thermal injury to non target tissue and/or the patient's pain or discomfort resulting from tissue heating.

Another embodiment provides an apparatus for treating the skin comprising a template having a tissue interface surface and an energy delivery device coupled to the template. The energy delivery device is configured to be coupled to a power source. A sensor is coupled to at least one of the template, a tissue surface, the energy delivery device, the tissue interface surface or a power source coupled to the energy delivery device. A feedback control system is coupled to at least one of the power source or the sensor. The feedback control system is configured to utilize a feedback signal indicative of a level of pain or discomfort felt by the patient resulting from tissue heating or injury to titrate the delivery of energy to the tissue site.

Yet another embodiment provides a method whereby patient heat or pain perception is utilized as an indicator of energy delivery or net heat transfer to the tissue site. Patient pain or thermal sensation can be correlated to total energy delivery, energy delivery rates or net heat transfer rates (i.e.

balance between heating due to energy delivery and cooling from a cooling media). A database can be generated of one or more of these correlations and utilized to control or titrate the delivery of energy and/or cooling.

Still another embodiment provides a system for regulating a tissue treatment procedure using patient feedback comprising a processor, a database coupled to the processor and a control module coupled to at least one of the database or the processor. The database includes a plurality of records. At least one record of the plurality includes at least one tissue treatment parameter and a pain or thermal sensation level associated with the at least one treatment parameter. The control module is configured to control an energy delivery parameter responsive to an input from at least one of a patient or the database.

Still yet another embodiment provides a computer readable medium on which is stored a database. The database includes a plurality of records, at least one record of the plurality including at least one tissue treatment parameter and a pain or thermal sensation level associated with the at least one treatment parameter. The database is configured to be coupled to a control module or a control system configured to control an energy delivery parameter responsive to an input from at least one of a patient or the database.

Another embodiment provides a system for regulating a tissue treatment procedure using patient feedback comprising a computing means, a database means coupled to the computing means and a control means coupled to at least one of the database means or the computing means. The database means includes a plurality of records. At least one record of the plurality includes at least one tissue treatment parameter and a pain or thermal sensation level associated with the at least one treatment parameter. The control means is configured to control an energy delivery parameter responsive to an input from at least one of a patient or the database means.

Yet another embodiment provides a method for energetically treating a tissue site comprising delivering energy to the tissue site using an energy delivery device; utilizing patient feedback to titrate the delivery of energy to the tissue site to reduce injury to a surface of the tissue site; and imparting a thermal injury to a portion of tissue within the tissue site.

Still yet another embodiment provides a method for treating a tissue site comprising delivering energy to a target tissue site of a patient using an energy delivery device; receiving feedback indicative of a patient pain or thermal sensation level; utilizing a database of digitally encoded correlations between at least one tissue treatment parameter and an associated pain or thermal sensation level to titrate the delivery of energy to the tissue site to reduce injury to a surface or layer of the tissue site; and imparting a thermal injury to a portion of tissue within the tissue site.

Another embodiment provides a system for regulating a tissue treatment procedure using erythema feedback comprising a processor, a database coupled to the processor and a control module coupled to at least one of the database or the processor. The database includes a plurality of records, at least one record of the plurality including at least one tissue treatment parameter and a level of erythema associated with the at least one treatment parameter. The control module is configured to control an energy delivery parameter responsive to a measurement of erythema.

Another embodiment provides a method for treating tissue using visual or photographic documentation or data. Pre-treatment photographs or images can be made of a selected treatment site using photographic or video imaging means and stored digitally or in analog form. Then an energy delivery treatment can be performed to obtain a desired tissue effect such as tissue reshaping, remodeling, smoothing, tightening or rejuvenation. A post treatment image can then be made and anatomical landmarks utilized to align the post-treatment and pre-treatment images manually or using computational means. A comparison can then be made between the pre and post treatments to qualitatively and/or quantitatively determine the effect of a given treatment session and/or a treatment endpoint. The comparison can be done using projection means, magnification means or electronic image analysis means such as an image analysis or spatial analysis software module. The comparison and/or alignment can also be made utilizing a grid pattern drawn or superimposed onto the treatment site using computation means. Subsequent energy delivery treatments can be performed if needed and controlled utilizing information derived from the comparison until the desired tissue effect or endpoint is obtained.

BRIEF DESCRIPTION OF THE DRAWINGS

FIG. 26 is a schematic diagram illustrating an embodiment for using patient feedback during tissue treatment.

FIG. 27 is a schematic diagram illustrating the use of correlations between biometric signals and a patient determined scale of thermal/pain sensation feedback.

FIG. 28 is a schematic diagram illustrating an embodiment for using biometric feedback signals (from the same or different locations on the body) to determine patient pain or thermal sensation resulting from a tissue treatment.

FIG. 29a is a schematic diagram illustrating an embodiment for using a patient determined scale of pain or thermal sensation as well a model or database to calibrate and/or correlate the scale.

FIG. 29b is a block diagram illustrating a configuration of a database used in an embodiment of the invention.

FIG. 29c illustrates an embodiment of a database table or an object table.

FIG. 30 is a flow chart illustrating a tissue treatment algorithm with patient feedback using a topical anesthetic.

FIG. 31 is a flow chart illustrating a tissue treatment algorithm with patient feedback using an injected local anesthetic.

FIG. 32 is a flow chart illustrating a photographic/visual documentation algorithm that can be used in one or more embodiments of the invention.

FIGS. 33a-33b are lateral views illustrating alignment and/or superimposition of pre and post images of the tissue site and surrounding tissue.

FIG. 34 is a lateral view illustrating use of a grid pattern aligned with a selected tissue feature or axis in an embodiment of a method to correct an aesthetic deformity.

FIG. 38 is a schematic diagram illustrating embodiments of the invention for measurement of tissue impedance.

FIGS. 41a-41b are frontal views illustrating a treatment grid and the use of the treatment grid to make a pattern of overlapping energy applications.

FIGS. 41c-41d are lateral views illustrating facial treatment sites for making overlapping or non-overlapping energy applications using an energy delivery device.

FIG. 41e is a cross sectional view illustrating the use of non-over-lapping energy applications to create separate thermal lesions.

FIG. 41f is a cross sectional view illustrating the use of over-lapping energy applications to create a continuous thermal lesion.

FIGS. 43a and 43b are lateral views illustrating the energetic tissue treatment without site selection.

FIG. 44 is a lateral view illustrating a convex aesthetic deformity.

FIGS. 45a and 45b are lateral views illustrating treatment of a tissue site using site selection tissue treatment based on convexity (45a) and the resulting uniformly flattened contour (45b).

FIG. 46 is a frontal view illustrating aesthetic deformities in the facial region including jowls, nasolabial folds and the submentum.

FIG. 47 is a frontal view illustrating treatment of aesthetic deformities in the facial region including jowls, nasolabial folds and the submentum.

FIGS. 48a-48e are lateral views illustrating mechanisms for treating convex deformities including downward contouring by thermal lipolysis (48a-48b), two dimensional skin tightening (48c-48d) and site selection treatment localized to areas of convexity (48e-48f).

DETAILED DESCRIPTION

Embodiments of the invention provide a method and apparatus to deliver energy to modify tissue including, collagen containing tissue, in the epidermal, dermal and subcutaneous tissue layers including adipose tissue. The energy can include electromagnetic, optical, thermal, acoustic and mechanical energy and combinations thereof. The modification of tissue can include modifying a physical feature of the tissue, a structure of the tissue or a physical property of the tissue and combinations thereof. The modification can be achieved by delivering sufficient energy to cause collagen shrinkage, and/or a wound healing response including the deposition of new or nascent collagen. For embodiments using topical energy delivery, energy can be delivered coupled with topical cooling to achieve heating of the subjacent dermis while preserving the epidermis. This provides a means to tighten or otherwise rejuvenate skin via two mechanisms. First an initial molecular contraction of pre-existing dermal collagen immediately tightens the skin during treatment. Then after 2 to 3 weeks, a secondary wound healing response further tightens skin from a cellular based contraction of dermal fibroblasts In various embodiments of the invention, the tissue modification procedure can be performed using patient feedback to control one or more aspects of the procedure including, without limitation, the delivery of energy to the tissue site, the delivery of a cooling medium to the tissue site and the level of thermal injury to the tissue site. Also, embodiments of the invention can be configured to use feedback to perform one or more of the following (i) reduce patient pain and discomfort before during or after a tissue treatment procedure; (ii) reduce the incidence of unwanted tissue injury including thermal injury, burns, blistering, and the like to selected tissue, tissue layers or tissue structures; (iii) increase the delivery of energy to a target tissue site or the temperature of the site with reduced injury to non target tissue; (iv) reduce procedure time; and (v) provide a more uniform therapeutic pattern of energy delivery over all or a portion of the treatment area that will at least partially increase skin tightening. Forms of patient feedback that can be utilized include without limitation, verbal feedback, biometric feedback, manual feedback and combinations thereof.

Figure 1:
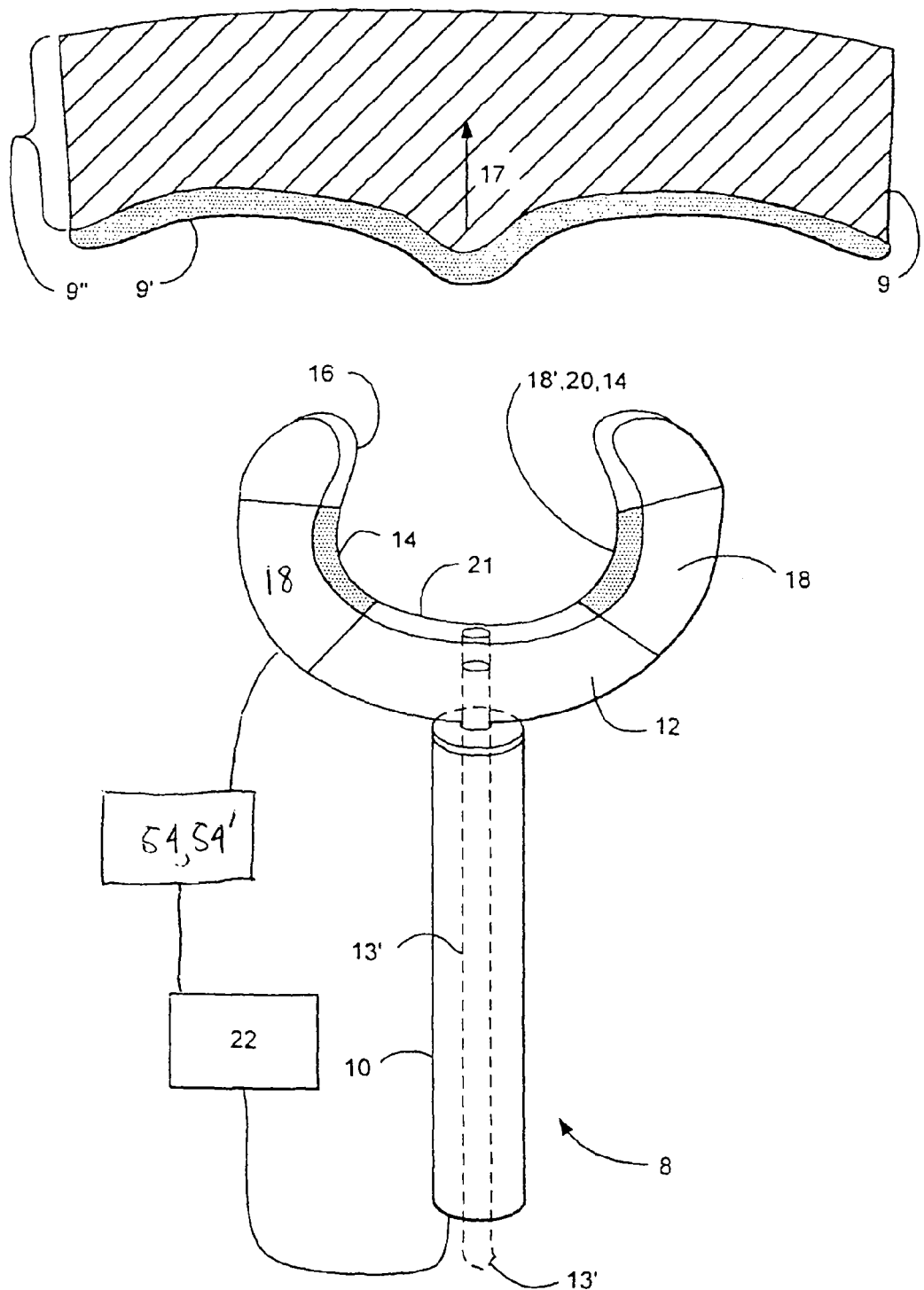
FIG. 1 is a lateral view of an embodiment of a skin treatment apparatus illustrating components of the apparatus including a feedback control system.

Biometric feedback can include without limitation, temperature measurement (on one or more sites on the body), EGK, EEG, blood pressure, pulse rate, respirations rate, electromyograms, skin electro-conductivity, other physiological measurements, voice stress recognition and combinations thereof. The biometric measurements can be made using one or more sensors described herein or known in the biomedical engineering, physiology or medical instrument arts. Manual feedback can be signaled by a variety of means known in the art including use of a keyboard, handgrip with pressure/force sensors, handheld device having a knob (coupled to a rheostat), switch, rocker switch, other hand or foot actuated device or other input/output device known in the art. The pressure or forces sensors can include solid-state sensors such as silicon strain gauges and MEM (micro electronic machines) and/or nanotechnology devices known in the art. Examples of MEMS devices include those manufactured by the Motorola® Corporation. Verbal feedback can include pain levels communicated to the physician as well as stress levels in the patient's voice determined by speech or pattern recognition software A discussion will now be presented of the use of various treatment apparatuses, energy devices, power sources, cooling devices, sensors and tissue treatment procedures which may be utilized with one or more embodiments of the invention. An exemplary embodiment of an apparatus 8 to treat or modify tissue 9 utilizing one or more methods of patient feedback described herein is shown in FIG. 1. This apparatus is exemplary and other tissue treatment apparatuses and methods are equally applicable. An example of an alternative apparatus can include one or more dermatological lasers known in the art. Other alternatives can include use of heat lamps, ultrasound or heat transfer fluids.

Tissue 9 can include a surface tissue layer 9' and underlying tissue 9". Surface tissue 9' can include the skin, epidermal skin layer or any collagen containing tissue and underlying tissue 9" can include dermal and sub-dermal layers including collagen containing underlying tissue.

In various embodiments, apparatus 8 can be configured to have one or more of the following components or functions: i) feedback control of energy delivery and applied force and other parameters discussed herein ii) cooled energy delivery devices, iii) delivery of cooling fluid to tissue site and/or energy devices iv) contact sensing of electrodes, v) control of energy delivery and applied force via the use of a database of combinations of energy, force, pressure, etc including direction, rates and total amounts delivered over time, the data base can alone or in combination with feedback control.

Figure 2A:
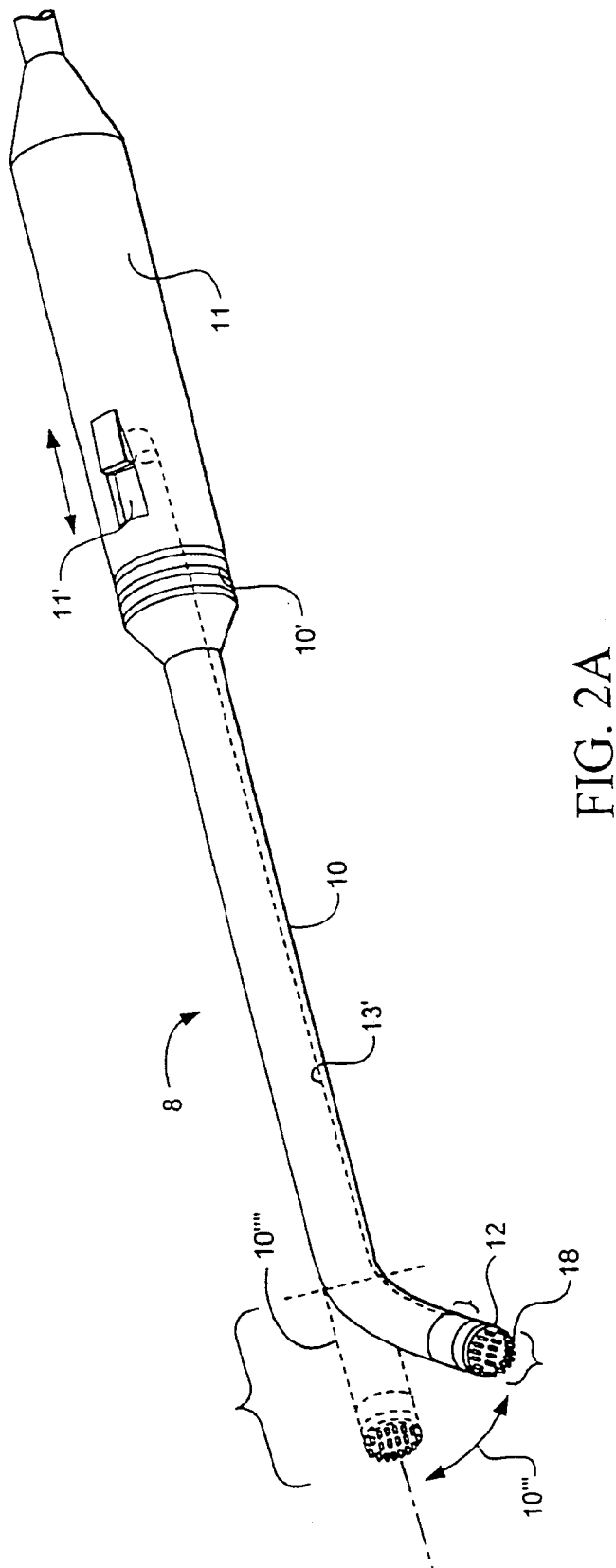
FIG. 2a is a lateral perspective view of the apparatus of FIG. 1 illustrating the introducer, template and energy delivery device.
Figure 2B:
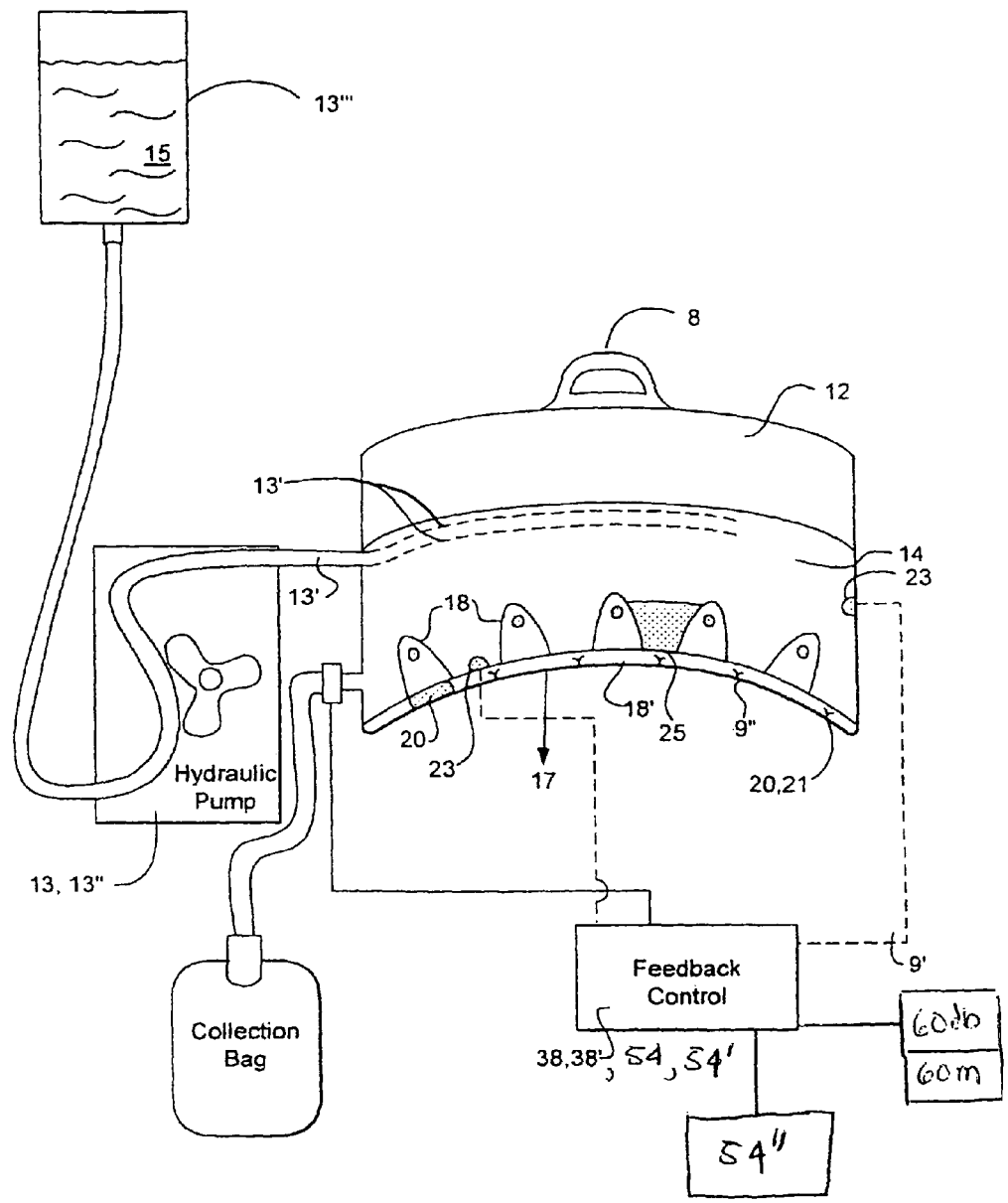
FIG. 2b is a lateral perspective view of the apparatus of FIG. 1 illustrating the use of a fluid delivery device.

Referring now to FIGS. 1, 2a and 2b, apparatus 10 can include an introducer 10 with proximal and distal ends 10' and 10". Introducer 10 is coupled at its distal end 10" to a template 12 which in turn can include a soft tissue mechanical force application surface 14 and a receiving opening 16 to receive a body structure. Mechanical force application surface 14 is configured to receive the body structure and apply force to soft tissue in the body structure, resulting in the application of a force 17 to that structure including its surface and underlying tissue.

Introducer 10 may have one or more lumens 13' that extend the fill length of the introducer or only a portion thereof. These lumens may be used as paths for the delivery of fluids and gases, as well as providing channels for cables, catheters, guide wires, pull wires, insulated wires, optical fibers, and viewing devices/scopes. In one embodiment, the introducer can be a multi-lumen catheter, as is well known to those skilled in the art. In another embodiment, introducer 10 can include or otherwise be coupled to a viewing device such as an endoscope, viewing scopes and the like.

In various embodiments, apparatus 8 can include a handpiece 11 coupled to introducer 10. Handpiece 11 can include a deflection mechanism 11' such as a pull wire or other mechanism known in the art. Deflection mechanism 11' can be used to deflect the distal end 10" of introducer 10 including template 12 by an angle 10''' relative to a lateral axis 10'''' of introducer 10. In various embodiments angle 10''' can be an acute angle (e.g. <90°) with specific embodiments of 60, 45 or 30°.

In an embodiment, an energy delivery device 18 is coupled to template 12. Energy delivery device 18 can be configured to deliver energy to template 12 to form a template energy delivery surface 20 at an interior of template 12 or at another position on template 12 (e.g., an exterior position). Energy delivery surface 20 contacts the skin or other tissue at a tissue interface 21. In various embodiments, one or more energy delivery devices 18 may deliver energy to template 12 and energy delivery surface 20. An energy source 22 (described herein) is coupled to energy delivery device 18 and/or energy delivery surface 20. Energy delivery device 18 and energy source 22 may be a single integral unit or each can be separate.

Referring now to FIG. 2b, a fluid delivery device 13 can be coupled to introducer 10 and/or template 12 including energy delivery device 18. Fluid delivery device 13 (which can also be a cooling device 13) serves to deliver fluid to tissue interface 21 and surrounding tissue to prevent or otherwise reduce thermal damage of the skin surface with the topical application of energy. Fluid delivery device 13 can be configured to be controlled by or responsive to various embodiments of patient feedback described herein. In an embodiment, fluid delivery device 13 can be configured (via means of a processor with embedded programming or electronic algorithm) to delivery an amount of fluid or cooling proportional to patient indicated level of pain or thermal sensation.

In various embodiments, fluid delivery device 13 can include one or more lumens 13' which can be the same or otherwise continuous (e.g. fluidically coupled) with lumen 13' in introducer 10 and template 12. Lumens 13' can be fluidically coupled to a pressure source 13" and fluid reservoir 13'''. Fluid delivery device 13 can also be coupled to a control system described herein. In various embodiments, pressure source 13" can be a pump (such as a peristaltic pump) or a tank or other source of pressurized inert gas (e.g. nitrogen, helium and the like).

Fluid delivery device 13 can be configured to deliver a heat transfer media 15 (also called a cooling media 15, flowable media 15 or fluid 15) to tissue interface 21, that serves to dissipate sufficient heat from the skin and underlying tissue at or near tissue interface 21 during the delivery of energy at or near this site so as to prevent or reduce thermal damage including burning and blistering. Similarly, fluid delivery device 13 may also deliver fluid 15 to and dissipate heat from energy delivery device 18 and/or template 12 to achieve a similar result. In various embodiments, introducer 10, including lumens 13' can serve as a cooling media introduction member 10 for heat transfer media 15.

Fluid 15 can serve as a heat transfer medium and its composition and physical properties can be configured to optimize its ability to dissipate heat. Desirable physical properties of fluid 15 include, but are not limited to, a high heat capacity (e.g. specific heat) and a high thermal conductivity (e.g. conduction coefficient) both of which can be of comparable values to liquid water in various embodiments or enhanced by the addition of chemical additives known in the art (e.g. sodium chloride). In other embodiments, fluid 15 may also serve to conduct RF energy and therefore have good electrical conductivity. Fluid 15 can be selected from a variety of fluids including, but not limited to water, saline solution (or other salt aqueous salt solutions), alcohol (ethyl or methyl), ethylene glycol or a combination thereof. Also, fluid 15 can be in a liquid or gaseous state, or may exist in two or more phases and may undergo a phase change as part of its cooling function, such as melting or evaporation (whereby heat is absorbed by the fluid as a latent heat of fusion or evaporation). In a specific embodiment, fluid 15 can be a liquid at or near its saturation temperature. In another embodiment, fluid 15 can be a gas which undergoes a rapid expansion resulting in a joule Thompson cooling of one or more of the following: fluid 15, tissue interface 21, energy delivery device 18 and energy delivery surface 20. In various embodiments, fluid 15 can be cooled to over a range of temperatures including but not limited to 32 to 98° F. In other embodiments fluid 15 can be configured to be cooled to cryogenic temperatures in a range including but not limited to 32 to −100° F. Fluid or heat transfer media 15 can be cooled by a variety of mechanisms, including but not limited to, conductive cooling, convective cooling (force and unforced), radiative cooling, evaporative cooling, melt cooling and ebullient cooling. Ebullient cooling involves the use of a liquid heat transfer liquid at or near saturation temperature. In various embodiments fluid 15 can also be an electrolytic fluid used to conduct or deliver RF energy to or in tissue and/or reduce impedance of selected tissue. Suitable electrolytic solutions can include without limitation, saline solutions, phosphate buffered saline solution, 0.9% saline solution, hypertonic saline solution, hypotonic saline solution, saline carrier solutions carrying a medicament, lidocain solutions, conductive gels known in the art, saline containing gels and combinations thereof. In other embodiments, thermal damage to skin 9' and underlying tissue 9" can be reduced or prevented through the use of a reverse thermal gradient device 25. Reverse thermal gradient device 25 can be positioned at or thermally coupled to template 12, mechanical force application surface 14 or energy delivery device 18. Suitable reverse thermal gradient devices 25 include but are not limited to peltier effect devices known in the art. Gradient device 25 can be configured to be responsive to or controlled by various embodiments of patient feedback described herein. In an embodiment, gradient device 25 can be configured (via means of a processor with embedded programming or electronic algorithms) to delivery an amount of fluid or cooling proportional to patient indicated level of pain or thermal sensation or to biometric indications thereof.

The delivery of cooling fluid 15 by fluid delivery device 13, energy (e.g. heat) by energy delivery device 18 and force (e.g. pressure) by force applications surface 14 can be regulated separately or in combination by a feedback control system described herein. Inputs parameters to the feedback control system 54 can include, but are not limited to temperature, impedance, pain or thermal sensation and biometric indications thereof, skin conductivity, skin color, and pressure of the tissue interface 21, energy delivery device 18 (including surface 18') and underlying structure, separately or in combination. The sequence of cooling and heating delivered to tissue interface 21 is controllable to prevent or reduce burning and other thermal damage to tissue.

Different cooling and heating control algorithms can be employed in different combinations of continuous and discontinuous modes of heating and cooling application. These control algorithms can be configured to receive input from one or more embodiments of patient feedback described herein as well as a database described herein of energy delivery parameters or other treatment parameters correlated to pain or thermal sensation levels or biometric indications thereof. Specific control algorithms that can be employed methods of patient feedback and control systems described herein include proportional (P), proportional-integral (PI) and proportional-integral-derivative algorithms (PID) the like, all well known in the art. These algorithms can use one or more input variables described herein including patient feedback and have their proportional, integral and derivative gains tuned to the specific combination of input variables. The control algorithms can be run either in an analog or digital mode using hardware described herein and can be configured to be coupled to one or more databases described herein. Temporal modes of delivery of cooling and energy to tissue interface 21 include, but are not limited to fixed rate continuous, variable rate continuous, fixed rate pulsed, variable rate pulsed and variable amount pulsing. Example delivery modes include the continuous application of the cooling means in which the flow rate is varied and application of the power source is pulsed or continuous i.e., the application of power can be applied in a pulsed fashion with continuous cooling in which the flow rate of cooling solution and the rate of RF energy pulsing (at a set power level) is varied as a function of surface monitoring of tissue interface 21. Pulsing of the cooling medium 15 flow rate may be either a constant or variable rate. A pulsed or intermittent application of cooling in which the frequency of pulsing is determined by surface monitors or patient feedback can also be combined with the application of a continuous or pulsed energy source. For instance, cooling can be applied as an intermittent spraying of a cryogen solution with a continuous application of RF energy. Even the amount of a single pulse of the cooling medium can be varied. Any liquid, such as a cryogen (e.g. liquid nitrogen) that quickly evaporates with heat, can be applied in this fashion. Another example of variable pulsing is the application of a constant rate of RF pulsing at a variable power level that is feedback controlled. Cooling can also be varied by pulsing the flow rate of cooling medium. More complicated algorithms can include the use of variable sequences of both cooling and heating. Less complicated algorithms can include a variable component with a fixed component of heating or cooling. An example of a less complicated algorithm involves the use of a database in which the algorithm may not use feedback control and in which certain fixed or non-variable combinations of heating and cooling are allowed to initiate a treatment cycle. Other embodiments of procedure control algorithms can use a combination of input from a database as well as feedback control.

Template 12 can be configured to deliver both electromagnetic energy and mechanical force to the selected tissue or anatomical structure 9. Suitable anatomical structures 9 include, but are not limited to, hips, buttocks, thighs, calves, knees, angles, feet, perineum, the abdomen, chest, back flanks, waistline, legs, arms, legs, arms, wrists, upper arms, axilla, elbows, eyelids, face, neck, ears, nose, lips, checks, forehead, hands, breasts and the like. In various embodiments, tissue structure 9 includes any collagen containing tissue structure.

Mechanical force application surface 14 can be configured to apply pressure, suction, adhesive forces and the like in order to create an extension or compression of the soft tissue structure and/or the skin surface. In an embodiment, the resting skin tension of the treatment site can be altered to direct a force vector of skin tightening through physical manipulation of the skin. Manually accentuating a skin redundancy along the longitudinal axis of the treatment grid will reduce the resting skin tension of the treatment site in the preferred direction and thereby further assist skin tightening in the preferred direction. Force application surface can interAlso, template 12 can include one or more energy delivery devices 18 configured to form an energy delivery surface 20 in the template 12. In various embodiments, energy delivery surface 20 can be the same size as force application surface 14, or it can be a smaller area.

A variety of mechanical forces can be applied to tissue using apparatus 8 and force application surface 14, including but not limited to, the following: (i) pressure, (ii) expansion, (iii) stretching, (iv) extension, (v) prolongation, or (vi) lengthening. The amount, direction and type of force can be controlled or titrated responsive to a number of factors including but not limited to an energy delivery parameter, tissue property, tissue feature or patient feedback. For example, in one embodiment the amount of force can be decreased in response to threshold pain indication by the patient.

Also the amount and direction of the force can be controlled simultaneously by changing the force vector (e.g., the direction and/or magnitude of the force) responsive to, for example, an energy delivery parameter, tissue property, tissue feature or patient feedback. In an embodiment, the force vector can be controlled responsive to one or more tissue properties such as temperature or elongation. For example, the magnitude of the force can be decreased as tissue temperature increases and/or the direction of the force can be changed as the tissue begins to elongate. In various embodiments the applied force can thus be vectored (i.e. changed in direction and/or magnitude) responsive to a number of factors to produce a desired tissue effect, e.g., smoothing, remodeling, contouring, etc.

The force can be applied by means of positive pressure or negative pressure. Positive pressure provides a compression of collagen containing tissue, with converging and diverging force vectors, while negative pressure creates an extension of collagen containing tissue with converging and diverging vectors. In various embodiments, the force 17 applied by force application surface 14 to tissue interface 21 is monitored and used as an input parameter (by sensors 23 described herein) as well as feedback controlled (by feedback means described herein) so as to perform or facilitate one or more of the following functions: (i) minimize and/or prevent burning and other thermal tissue damage; (ii) serve as a therapeutic modality to increase or decrease the delivery of thermal energy and mechanical force to the intended treatment site. In a preferred embodiment, the applied force 17 measured and monitored as described, is a pressure (e.g. force per unit tissue surface area) or otherwise expressed as such. In bipolar electrode applications describe herein, the force 17 applied by force application surface 14 can be limited to that amount necessary to achieve contact with skin.

Suitable sensors 23 that can that can be used to measure applied force or pressure to tissue include, but are not limited to strain gauges which can be made out of silicon and micro machined using techniques well known in the art. Suitable pressure sensors include the NPH series TO-8 Packaged Silicon Pressure Sensor manufactured by Lucas NovaSensor®.

Suitable energy sources 22 that may be employed in one or more embodiments of the invention include, but are not limited to, the following: (i) a radio-frequency (RF) source coupled to an RF electrode, (ii) a coherent source of light coupled to an optical fiber, (iii) an incoherent light source coupled to an optical fiber, (iv) a heated fluid coupled to a catheter with a closed channel configured to receive the heated fluid, (v) a heated fluid coupled to a catheter with an open channel configured to receive the heated fluid, (vi) a cooled fluid coupled to a catheter with a closed channel configured to receive the cooled fluid, (vii) a cooled fluid coupled to a catheter with an open channel configured to receive the cooled fluid, (viii) a cryogenic fluid, (ix) a resistive heating source, (x) a microwave source providing energy from 915 MHz to 2.45 GHz and coupled to a microwave antenna, (xi) an ultrasound power source coupled to an ultrasound emitter, wherein the ultrasound power source produces energy in the range of 300 KHZ to 3 GHz, (xii) a microwave source or (xiii) a fluid jet.

Energy delivery 18 can be configured to be controlled by or responsive to various embodiments of patient feedback described herein. In an embodiment, the energy delivery device can be configured (via a control system 54 described herein) to deliver an amount of energy responsive to a patient indicated level of pain or thermal sensation, a biometric signal correlated to or otherwise indicative of pain or thermal sensation. In various embodiments using patient feedback, energy delivery device 18 can be configured to operate within one or more of the following parameters: (i) provide a controlled delivery of electromagnetic energy to the skin surface that does not exceed, 1,000 joules/cm2, or 10 joules/sec/cm2; (ii) provide a controlled delivery of electromagnetic energy to the skin surface not exceeding 600 joules/cm2 during a single treatment session (during a twenty-four hour period); (iii) provide a controlled delivery of electromagnetic energy to the skin surface not exceeding 200 joules/cm2 during a single treatment session, or not exceeding 10 joules/sec/cm2; (iv) operate in an impedance range at the skin surface of, 70 ohms cm2 (measured at a frequency of 88 Hz) to 40 Kohms cm2 (measured at a frequency of 10 KHz); (v) provides a controlled delivery of electromagnetic energy to operate in a range of skin thermal conductivities (at or near the skin surface) of 0.20 to 1.2 k (where k=1*[W/(m. C.°)]); and (vi) operate in a range of compression forces applied to the skin surface and/or the underlying soft tissue anatomical structure not exceeding 400 mmHg, not exceeding 300 mm, not exceeding 200 mmHg or not exceeding 100 mmHg. In an embodiment a database, described herein, can be developed that correlates one or more of these parameters to an associated level of pain or thermal sensation or a biometric indication thereof. The database can subsequently be configured to be utilized to control or regulate one of these parameters during an energy delivery procedure through the use of patient feedback which is indicative of pain or thermal sensation.

For ease of discussion, the power source utilized is an RF source and energy delivery device 18 is one or more RF electrodes 18. However, all of the other power sources and energy delivery devices mentioned herein are equally applicable to both apparatus 8 and tissue treatment methods using apparatus 8 including various embodiments using patient feedback described herein.

Template 12 can apply both a mechanical force and deliver energy to do one or more of the following: (i) tighten the skin, (ii) smooth the surface of the skin, (iii) improve a compliance of the skin surface, (iv) improve a flexibility of the skin surface; and (v) provides cellular remodeling of collagen in soft tissue anatomical structures. Mechanical force application surface 14, (i) is at least partially conforming to the skin surface, (ii) may apply a substantially even pressure to the soft tissue anatomical structures and (iii) can apply a variable pressure to the skin surface and underlying soft tissue structures. The combined delivery of electromagnetic energy and a mechanical force is used to create a three-dimensional contouring of the soft tissue structure. The amount of mechanical force applied by mechanical force application surface 14 can be selectable to meet one or more of the following criteria: (i) sufficient to achieve a smoothing effect of the skin surface, (ii) can be less than the tensile strength of collagen in tissue and (iii) sufficient to create force vectors that cleave collagen cross-links to remodel collagen containing structures.

A sensor 23 is positioned at or adjacent energy delivery surface 20 and/or electrode 18 to monitor temperature, impedance (electrical), cooling media fluid flow and the like of tissue 9 of one or more of the following: tissue interface 21, tissue 11, or electrode 18. Suitable sensors 23 include impedance, thermal and flow measurement devices. Sensor 23 is used to control the delivery of energy and reduce the risk of cell necrosis at the surface of the skin as well and/or damage to underlying soft tissue structures. Sensor 23 is of conventional design, including but not limited to thermistors, thermocouples, resistive wires, and the like. A suitable thermal sensor 23 includes a T type thermocouple with copper constantene, J type, E type, K type, fiber optics, resistive wires, thermocouple IR detectors, and the like. Suitable flow sensors include ultrasonic, electromagnetic and aneometric (including thin and hot film varieties) as is well known in the art. In various embodiments, two or more temperature and/or impedance sensors 23 are placed on opposite sides or otherwise opposing geometric positions of electrode 18 or energy delivery surface 20. Such embodiments can be configured to measure temperature or impedance gradients across a selected area of tissue Apparatus 8 can be configured to deliver sufficient energy and/or force to meet the energy levels for disrupting and/or cleaving each type of molecular bond within the collagen matrix. Patient feedback can be utilized to regulate delivered energy level for disrupting/cleaving each type of molecular bond. Collagen crosslinks may be either intramolecular (hydrogen bond) or intermolecular (covalent and ionic bonds). Hydrogen bonds are disrupted by heat. Covalent bonds may be cleaved with the stress created from the hydrogen bond disruption and the application of an external mechanical force. Cleavage of ionic bonds may be achieved with an alternating electromagnetic force (as would be induced by an electromagnetic field such as an RF field) in addition to the application of an external mechanical force that is applied by template 12. The strength of a hydrogen bond is relatively weak and can be thermally disrupted without ablation of tissue. The in vitro thermal cleavage of the hydrogen bond crosslinks of tropocollagen can result in the molecular contraction of the triple helix up to one third of its original length. However, in vivo collagen exists in fibrils that have extensive intermolecular crosslinks that are covalent or ionic in nature. These covalent and ionic crosslinks are stronger and cannot be easily disrupted with heat alone. These intermolecular bonds are the main structural determinants of the collagen matrix strength and morphology. In vivo thermal disruption of intramolecular hydrogen bonds will not by itself result in a significant change in matrix morphology. As the intermolecular crosslinks are heat stable, cleavage may occur by a secondary process which can be the result of thermal disruption of intramolecular hydrogen bonds. In the non-polar region of the collagen fibril, intermolecular covalent bonds predominate (intramolecular covalent bonds are also present but are fewer in number).

Figure 3:
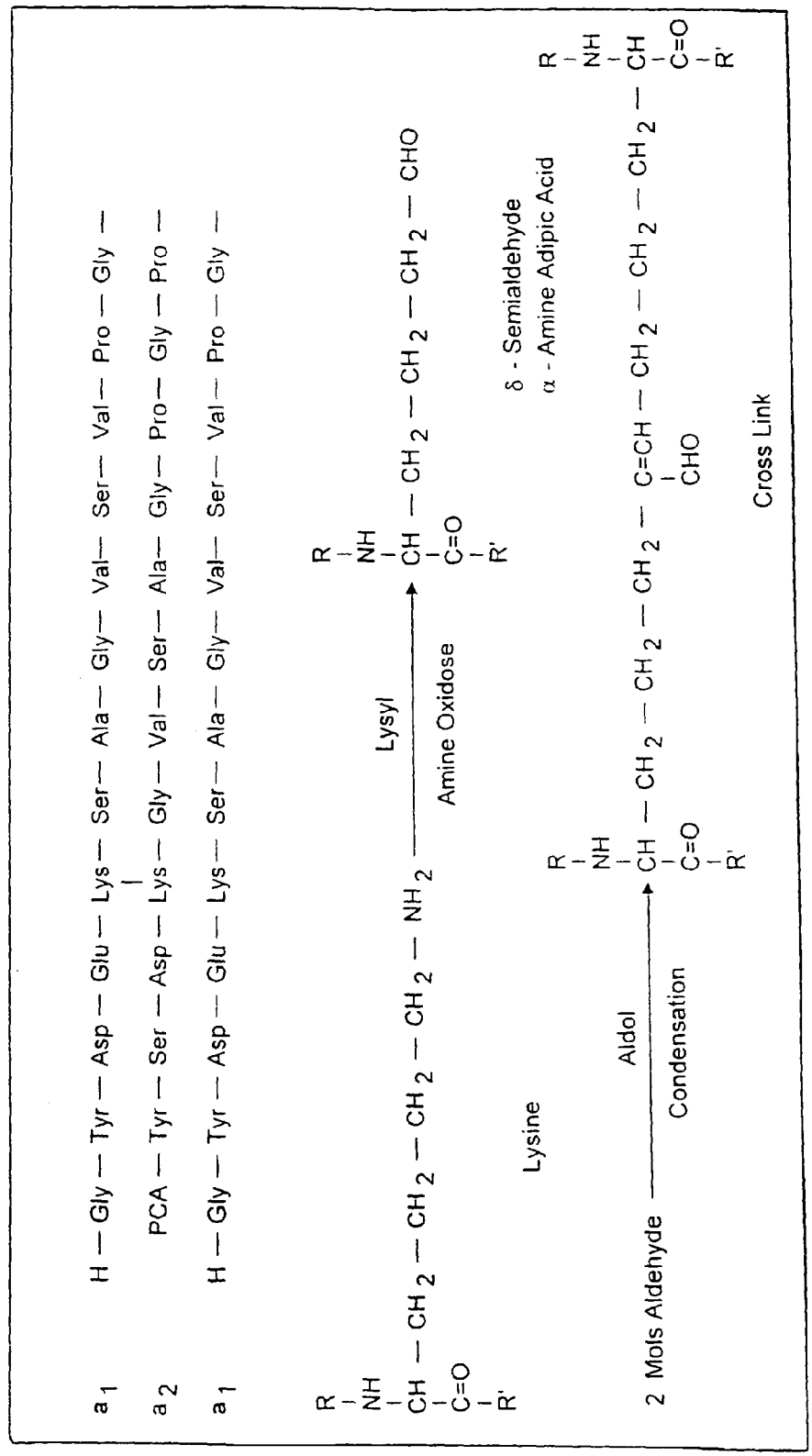
FIG. 3 illustrates intramolecular cross-linking of collagen.
Figure 4:
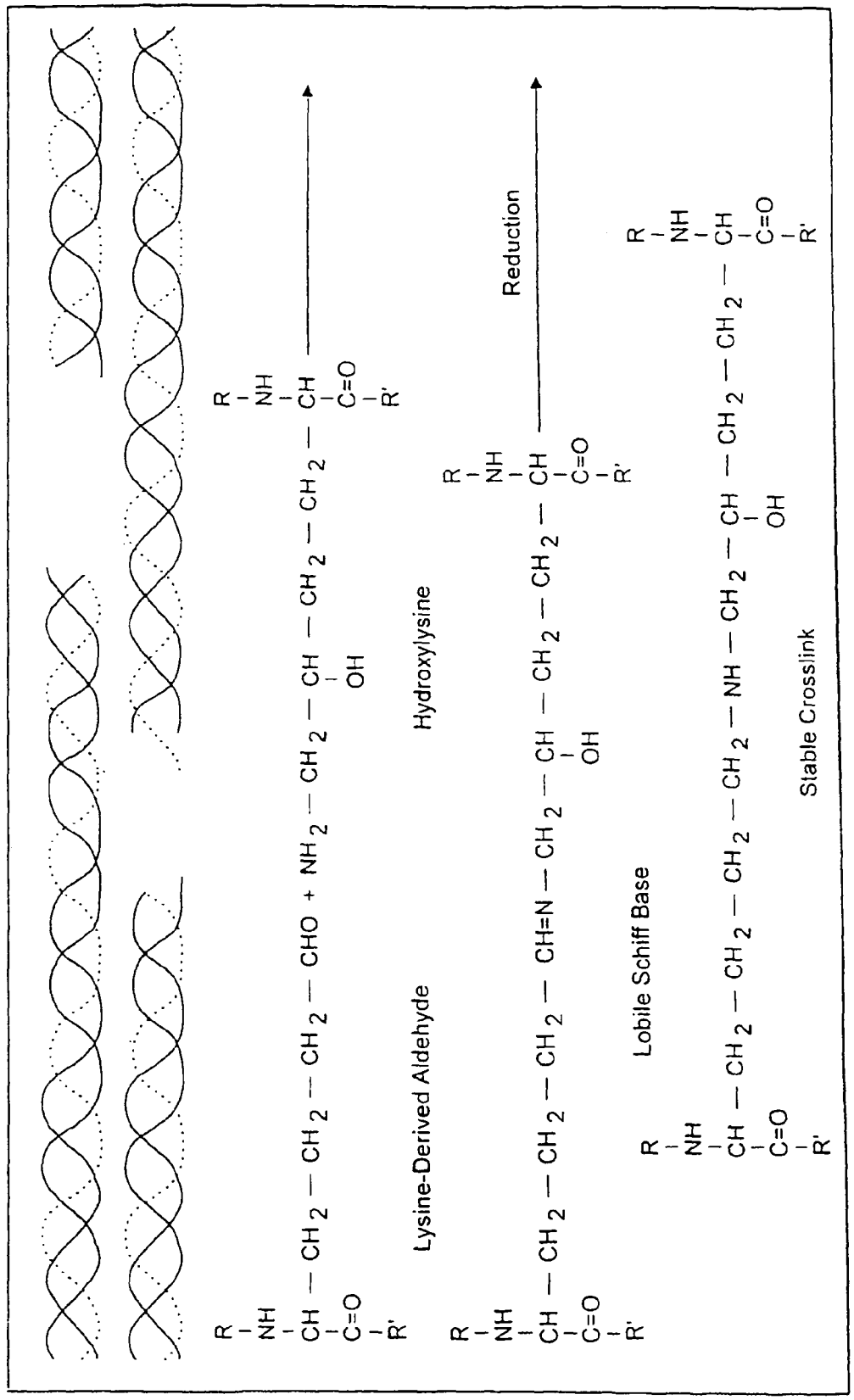
FIG. 4 illustrates intermolecular cross-linking of collagen.

These intermolecular covalent crosslinks increase with age, (refer to FIGS. 3 and 4). As a result, the solubility of the collagen matrix in a soft tissue structure is reduced with this maturation process. Although tensile strength is increased, the collagen containing tissue becomes less compliant. Cleavage of an intermolecular bond can require approximately one EV (electron volt) of energy and cannot be accomplished by heat without thermal ablation of tissue. In addition, covalent bonds are not strongly polar and will not be significantly affected by an RF current at this reduced power level. Cleavage of intermolecular covalent bonds that result in matrix remodeling without ablation is achieved by the stress created from the thermal disruption of intramolecular hydrogen bonds. Additional remodeling stress can be provided with the application of an external force that has the appropriate orientation to the fibrils of the matrix. Suitable orientations include approximately parallel to the lateral axis of the collagen fibrils. Ionic bonds are essentially intermolecular and are present in the polar regions of the fibril. Although slightly weaker than covalent bonds, thermal disruption of ionic bonds cannot occur without ablation of tissue. An RF field is an effective means to cleave these bonds and can be created by the in phase alternating ionic motion of the extracellular fluid. Frequency modulation of the RF current may allow coupling to the ionic bonds in the polar regions of the fibril. Remodeling of a target site may be optimized by the selection of a band of the spectrum that is target site specific in order to reduce collateral damage. If an optimized intrinsic absorption is insufficient then a selective medium may be provided to alter the absorption in order to discriminate various soft tissue structures. This may be achieved by altering the absorption. By altering the extra-cellular fluid content of a soft tissue in specific ways, the delivery of energy to a target tissue site is achieved with minimal damage to collateral structures such as skin and adjacent soft tissue structures.

The reforming of bonds at the same bond site can diminish the remodeling process. Relaxation phenomena may be inhibited with the application of an external mechanical force that separates bond sites but allows the reforming of these covalent and ionic bonds in a lengthened or contracted morphology. This can be the underlying biophysical process that occurs with the controlled remodeling of the collagen matrix. Ground substance may also function to diminish relaxation of crosslinks through competitive inhibition. Chondroitin sulfate is a highly charged molecule that is attached to a protein in a "bottle brush" configuration. This configuration promotes attachment at polar regions of the fibril and reduces the relaxation of ionic bonds in this region. As a consequence, immature soluble collagen, which has fewer intermolecular crosslinks and contains a higher concentration of ground substance, may be more easily remodeled. The induction of scar collagen through the wound healing sequence may also facilitate the remodeling process within a treatment area.

Collagen cleavage in tissue is a probability event dependant on temperature. There is a greater probability that a collagen bond will be cleaved with higher temperatures. Cleavage of collagen bonds will occur at lower temperatures but at a lower frequency. Low level thermal cleavage is frequently associated with relaxation phenomena in which there is not a net change in molecular length. An external force that mechanically cleaves the fibril may reduce the probability of relaxation phenomena. The application of an external force will also provide a means to lengthen or contract the collagen matrix at lower temperatures while reducing the potential of surface ablation. The cleavage of crosslinks with collagen remodeling may be occurring at a basal metabolic temperature that is expressed morphologically as the process of aging. Although the probability for significant cleavage in a short period of time is small, aging may be expressed as a low level steady state of collagen remodeling with the external force of gravity that becomes very significant over a period of decades. Hydrogen bonds that are relatively weak (e.g. bond strength of 0.2 to 0.4 ev) are formed within the tertiary structure of the tropocollagen molecule.

Figure 5:
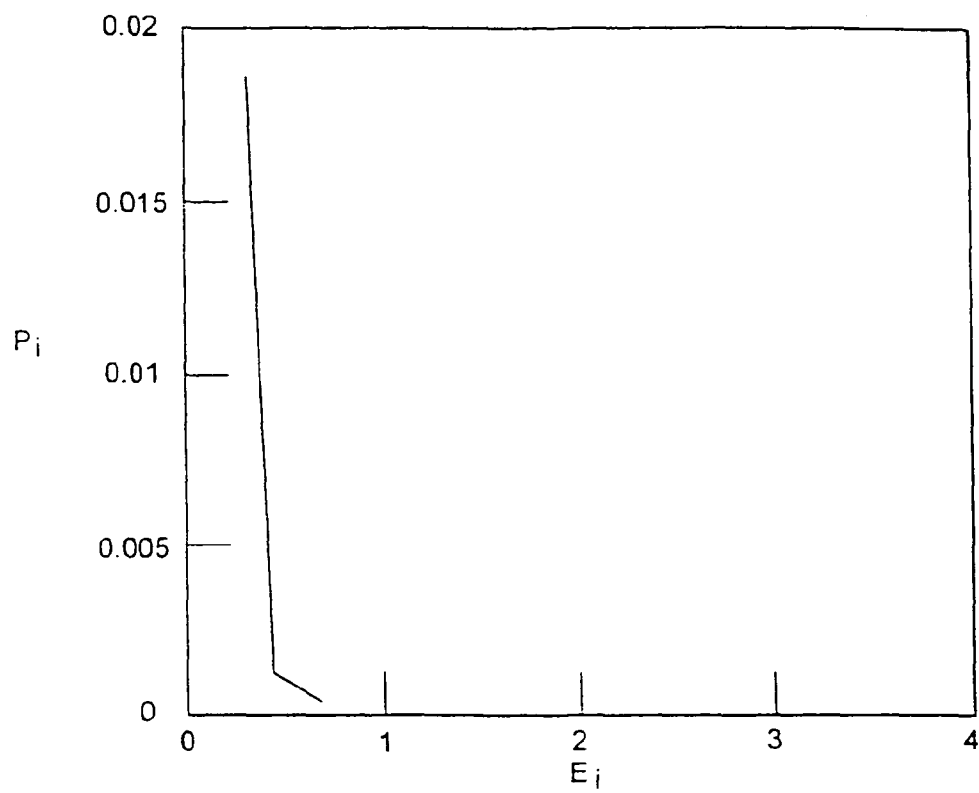
FIGS. 5 and 6 are two graphs illustrating the probability of collagen cleavage as a function of molecular bond strength at 37° C.
Figure 6:
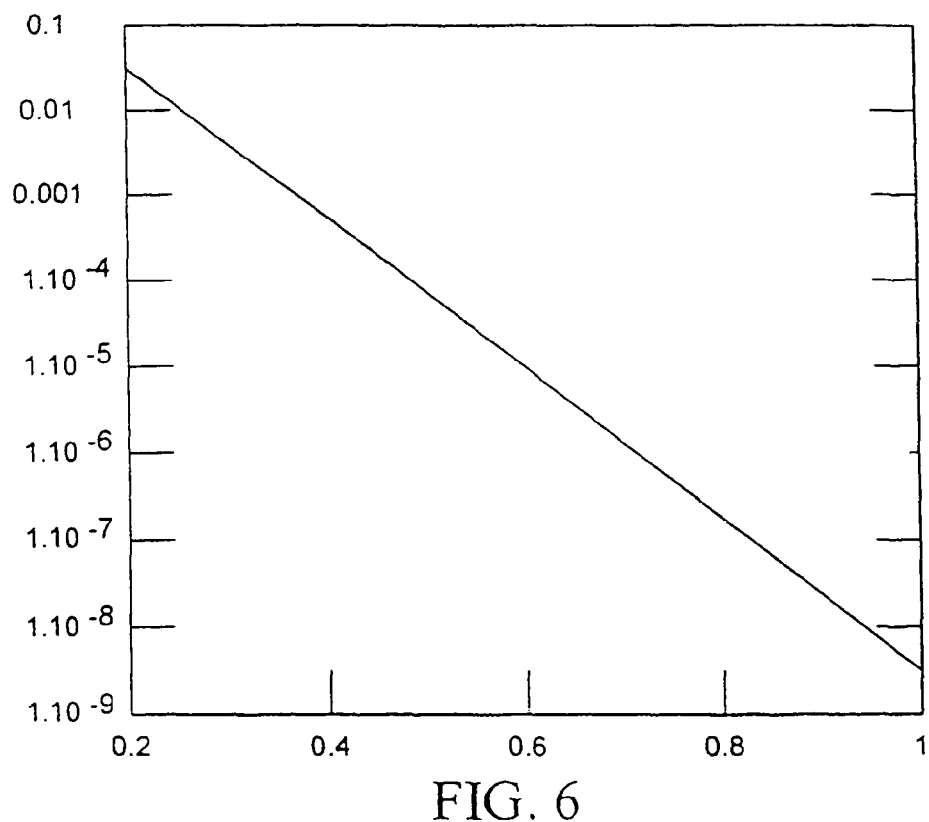

Thermal disruption of these bonds can be achieved without ablation of tissue or cell necrosis. The probability of hydrogen bond disruption at a certain temperature can be predicted by statistical thermodynamics. If a Boltzmann distribution is used to calculate the probability of bond disruption then a graph illustrating the relationship between bond strength and the probability of bond disruption at a certain temperature can be produced. Graphs of the probability of cleavage (at 37° C.) versus bond strengths are shown in FIGS. 5 and 6.

Different morphological expressions of aging may be due to the effect of gravity upon the matrix of a particular area. In areas of the skin envelope in which gravity lengthens the matrix, elastosis of skin will occur. In contrast to skin aging certain anatomical structures, such as joint ligaments, will appear to tighten with the aging process. The reduced range of motion may be due in part to the vertical vector of gravity contracting the matrix of a vertically aligned ligament. However, most of the "tightening" or reduced range of motion of joints may not be secondary to a contracted matrix but is due to reduced flexibility of the matrix caused by increased intramolecular cross-linking that occurs with aging. Essentially, the controlled remodeling of collagen is the reversal of the aging process and involves the reduction in the number of intermolecular crosslinks. As a result the remodeled matrix becomes less brittle. Greater flexibility of the soft tissue has several functional advantages including an increased range of motion of component joints.

When the rate of thermal cleavage of intramolecular crosslinks exceeds the rate of relaxation (reforming of hydrogen bonds) then the contraction of the tertiary structure of the molecule can be achieved. No external force is required for this process to occur. Essentially, the contraction of the tertiary structure of the molecule creates the initial intermolecular vector of contraction. The application of an external mechanical force during thermal cleavage will also affect the length of the collagen fibril and is determined by the overall sum of intrinsic and extrinsic vectors that is applied during a cleavage event. Collagen fibrils in a matrix exhibit a variety of spatial orientations. The matrix is lengthened if the sum of all vectors acts to distract the fibril. Contraction of the matrix is facilitated if the sum of all extrinsic vectors acts to shorten the fibril. Thermal disruption of intramolecular bonds and mechanical cleavage of intermolecular crosslinks is also affected by relaxation events that restore preexisting configurations. However, a permanent change of molecular length will occur if crosslinks are reformed after lengthening or contraction of the collagen fibril. The continuous application of an external mechanical force will increase the probability of crosslinks forming, alter lengthening or contraction of the fibril.

The amount of (intramolecular) hydrogen bond cleavage required for remodeling can be determined by the combined ionic and covalent intermolecular bond strengths within the collagen fibril. Until this threshold is reached little or no change in the quaternary structure of the collagen fibril will occur. When the intermolecular stress is adequate, cleavage of the ionic and covalent bonds will occur. Typically, the intermolecular cleavage of ionic and covalent bonds will occur with a ratcheting effect from the realignment of polar and non-polar regions in the lengthened or contracted fibril. The birefringence (as seen with the electron microscope) of the collagen fibril may be altered but not lost with this remodeling process. The quarter staggered configuration of the tropocollagen molecules in the native fiber exhibits a 680 D banding which either lengthens or contracts depending on the clinical application. The application of the mechanical force with template 12 during the remodeling process determines if a lengthened or contracted morphology of the collagen fibril is created. An external force of contraction will result in the contraction of the tertiary and quaternary structure of the matrix. With the application of an external distraction force, intramolecular contraction may still occur from the intrinsic vector that is inherent within its tertiary structure. However, overall lengthening of the quaternary structure of the fibril will occur due to the mechanical cleavage of the intermolecular bonds. Contraction of the tertiary structure with overall lengthening of the collagen fibril can alter the birefringence of the matrix. The altered periodicity will be exhibited in the remodeled matrix that will correlate to the amount of lengthening achieved.

Delivery of both electromagnetic energy and mechanical energy to the selected body structure involves both molecular and cellular remodeling of collagen containing tissues. In an embodiment, low-level thermal treatments can be delivered over several days to provide an alternative way to contract skin with minimal blistering and cell necrosis. Patient feedback can be utilized using the pain/thermal scale to maintain thermal treatment at low levels. For example, a series of treatments can be delivered where the energy level is titrated to maintain pain perception at or below a level 1.

Cellular contraction involves the initiation of an inflammatory/wound healing sequence that is perpetuated over several weeks with sequential and lengthy low level thermal treatments. Contraction of skin is achieved through fibroblastic multiplication and contraction with the deposition of a static supporting matrix of nascent scar collagen. This cellular contraction process is a biological threshold event initiated by the degranulation of the mast cell that releases histamine. This histamine release initiates the inflammatory wound healing sequence.

Molecular contraction of collagen is a more immediate biophysical process that occurs most efficiently with electromagnetic energy delivery devices, including but not limited to RF electrodes. The clinical setting is physician controlled and can involve more precise temperature, inpedance, cooling media flow and energy delivery monitoring to avoid blistering of the skin. Measured impedance will vary with the frequency of the electromagnetic energy applied to the skin surface and/or underlying soft tissue structure.

Figure 7:
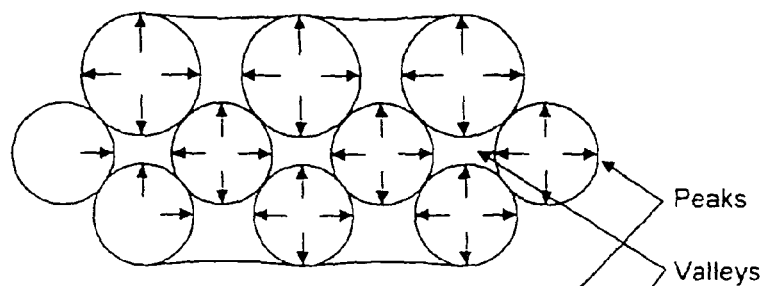
FIG. 7 is a top view of a skin surface, illustrating the peaks and valleys of the surface and the force components applied to the surface resulting from the application of a mechanical force.
Figure 8:
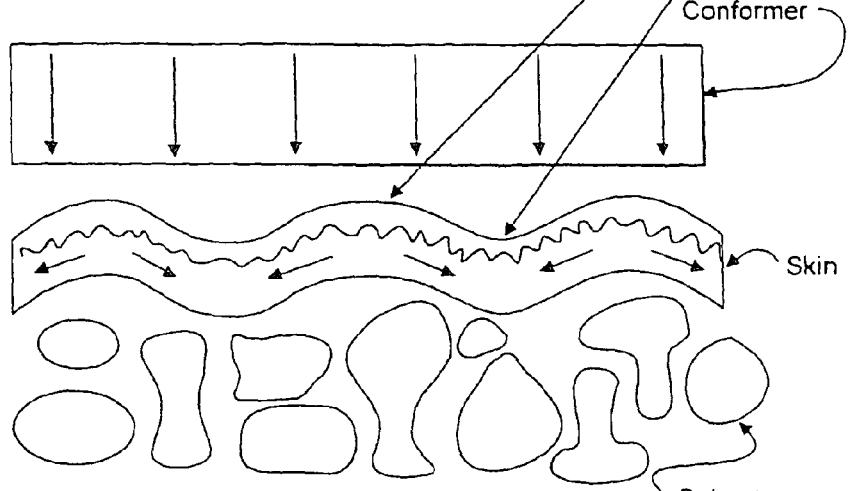
FIG. 8 is a cross-sectional view of the skin surface illustrated in FIG. 7.

Patients may be treated with one or more modalities described herein to achieve a selectable esthetic result. Refinements to the treatment area may be performed using apparatus 8 in the physician's office. However, tightening of a skin surface may accentuate any preexisting contour irregularities. For this reason, conforming esthetic template 12 can also be configured to be used to smooth surface contour irregularities. The application of a mechanical force upon the collagen matrix can involve both contraction or distraction of the selected soft tissue structure to achieve a smoother contour. Thermal (or electromagnetic) cleavage of collagen crosslinks when combined with a mechanical force creates force vectors that contract, distract or shear the longitudinal axis of the fibril. A vector space is created with the combination of a scalar component (heat) and a force vector (an externally applied mechanical force). The force vectors within this vector space may vary depending upon the specific morphology of the tissue. For example, the peaks and valleys of cellulite will have different force vectors when uniform external compression is applied. As illustrated in FIGS. 7 and 8, template 12 produces converging and diverging force vectors that act to smooth surface morphology by contracting (valleys) and distracting (peaks) the collagen matrix in a soft tissue structure. Diverging vectors on the peaks lengthen the collagen matrix while converging vectors in the valleys contract and compact the collagen matrix. The overall result is the smoothing of an irregular skin surface.

Figure 9:
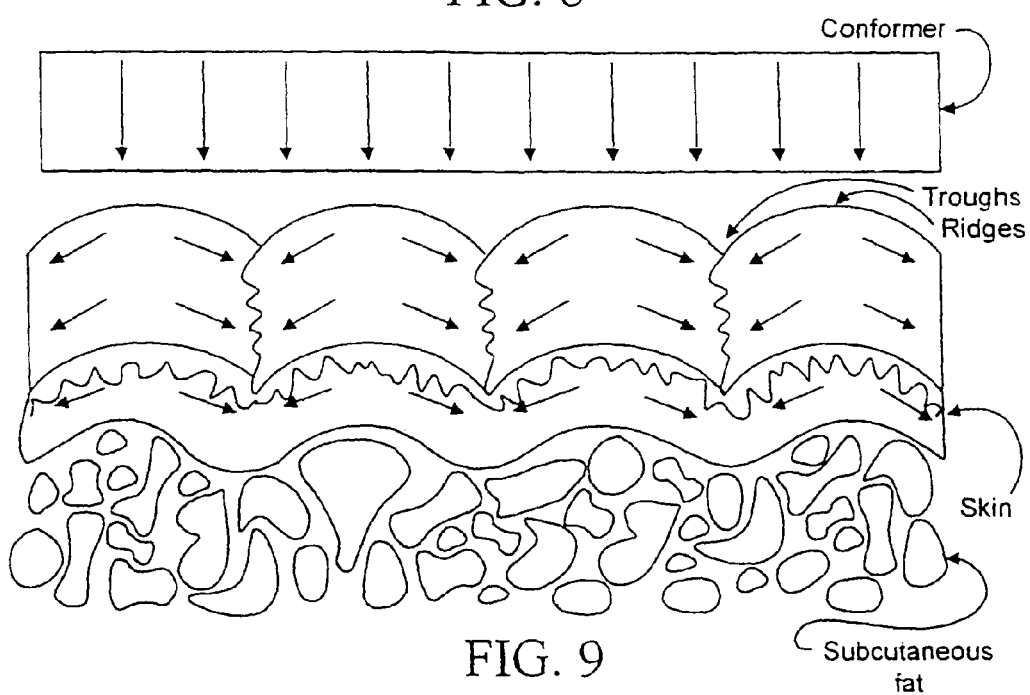
FIG. 9 is a cut-away view of the skin surface, with troughs and ridges, and underlying subcutaneous soft tissue.

Apparatus 8 may also be used to treat wrinkling of the skin. The treatment of skin wrinkles is shown in FIG. 9. In a skin wrinkle the vectors of applied force can be directed perpendicular to the troughs and ridges of this contour deformity. Diverging vectors at the ridges of the skin converge in the trough of the wrinkle to smooth the surface morphology. The collagen matrix can be distracted or extended at the ridges and contracted in the valleys. One or embodiments of patient feedback can be utilized to optimize this process by controlling energy to minimize blistering or burning. The overall result is the smoothing of the wrinkled skin surface.

Linear scars exhibit a similar morphology and can be remodeled with apparatus 8. Any surface irregularity with depressions and elevations will have vectors directed to the lowest point of the deformity. Prominent "pores" or acne scarring of the skin have a similar pattern to cellulite but on a smaller scale and can also be treated with apparatus 8. Clinically, the application of the mechanical force reduces the power required to remodel the matrix and diminishes cell necrosis of the skin surface as well as underlying soft tissue structures. Compression alters the extracellular fluid of the soft tissue structure (collagen) and exerts electrical impedance and thermal conductivity effects that allow delineation of a conduit-treatment interface of the collagen containing tissues. A deeper dermal interface will contract skin and exert three dimensional contour effects while a more superficial interface will smooth surface morphology.

Figure 10B:
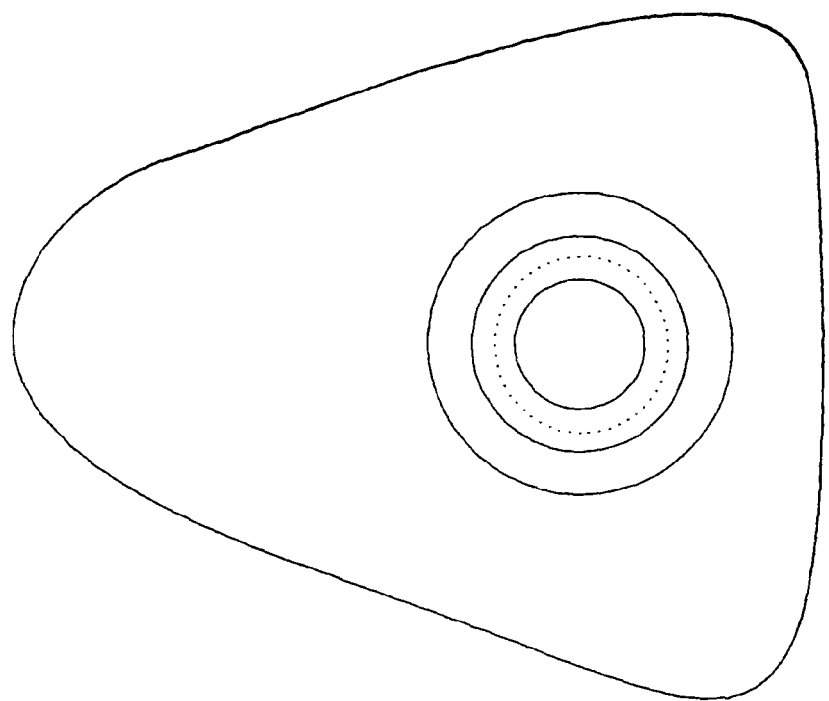
FIG. 10(b) is a front perspective view of the breast expander of FIG. 10(a).
Figure 10A:
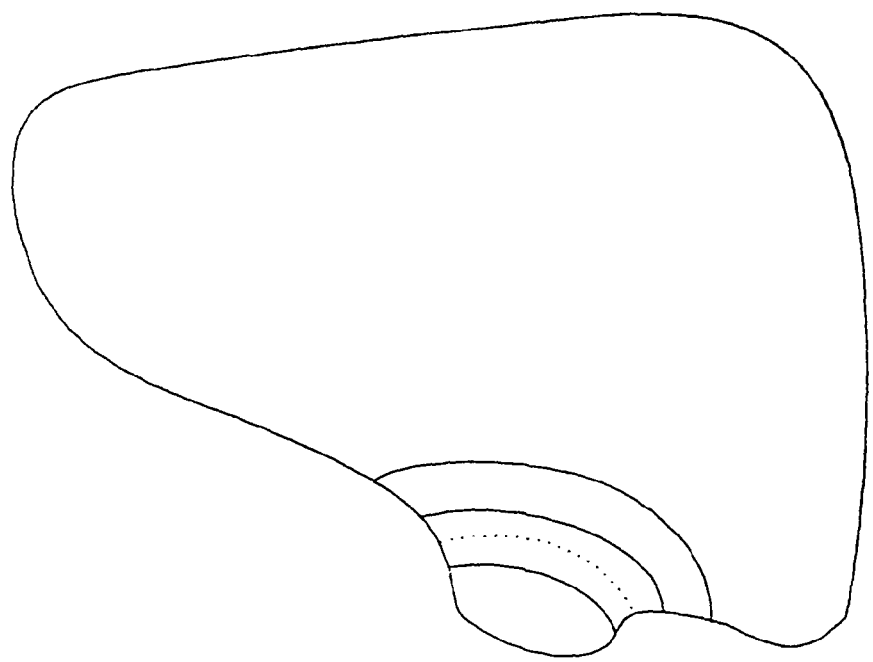
FIG. 10(a) is a lateral perspective view of a telescoping segment of a breast expander useful with the apparatus of FIG. 1.
Figure 10C:
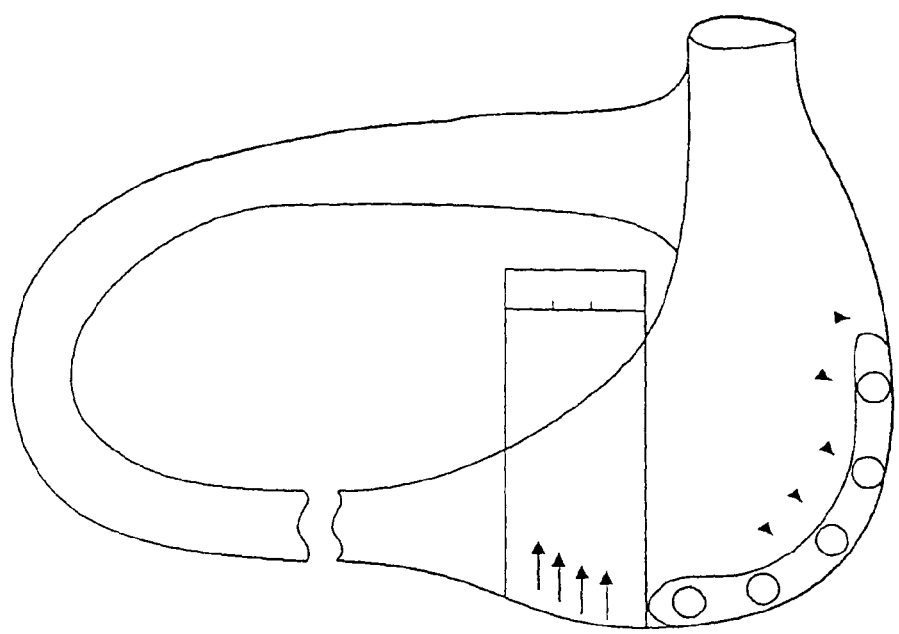
FIG. 10(c) illustrates a bra which functions as the template of FIG. 1.
Figure 10E:
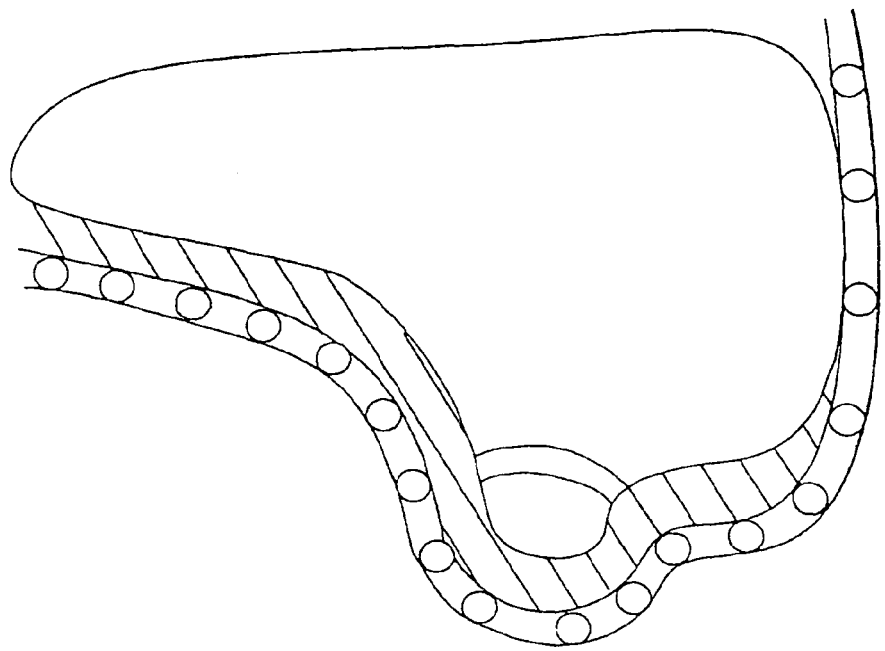
FIG. 10(e) is a lateral cross-sectional perspective view of a fully expanded breast expander within a breast.
Figure 10D:
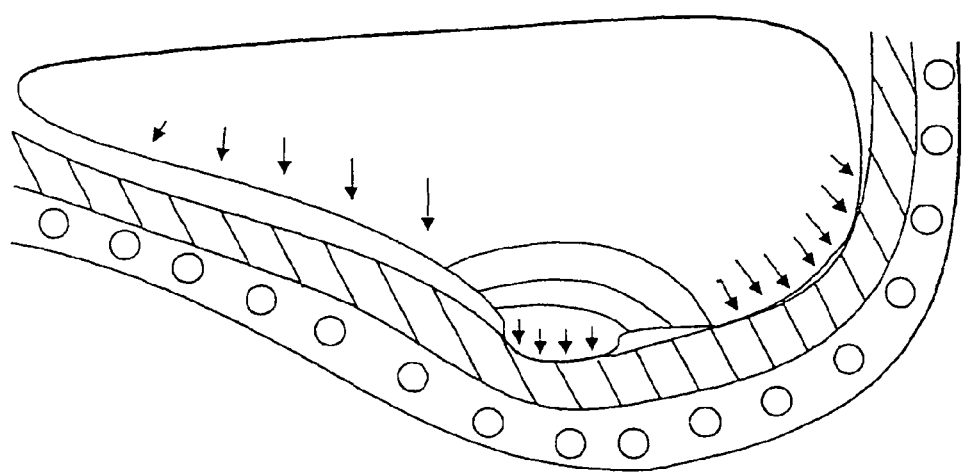
FIG. 10(d) is a lateral cross-sectional perspective view of a partially expanded breast expander within a breast.

In circumstances in which expansion of the skin envelope is needed, the combined application of heat and pressure can also be utilized with various embodiments of patient feedback to control one or both parameters. For breast reconstruction, expansion of the skin envelope can be achieved with each inflation of a subpectoral breast expander. FIGS. 10(a) and 10(b) illustrate an expander with an RF receiver electrode. A telescoping segment with an RF energy source is incorporated with access valve and is used to expand a nipple areolar donor site for Pectoralis "Peg" Procedure. The segmental expander can also be used to prepare the recipient site for delayed autologous "Peg" Flap. The pressure that is exerted on the skin and the periprosthetic scar capsule is from the inside. In this application, vectors are directed outward. As an adjunct to this expansion process, a controlled thermal pad may be incorporated into a bra, as illustrated in FIG. 10(c), which can be applied to the inferior pole of the breast skin to promote lengthening of collagen fibril within the skin and underlying scar capsule around the expander. The bra may also function as an external conforming template 12 to achieve a specific breast shape. The net result is the creation of a more esthetic breast reconstruction with three-dimensional characteristics of the opposite breast. In a like manner, other garments can be utilized as external conforming templates for other anatomical body structures. In FIG. 10(d) a breast expander is partially expanded within the breast. In FIG. 10(e), the expander is fully expanded within the breast.

Template 12 can be configured to apply a mechanical force in combination with the delivery of energy to the skin surface and underlying soft tissue structure, to remodel collagen both esthetically and functionally with minimal thermal damage including cell necrosis. Additionally, template 12 can be configured (as described herein) to deliver both mechanical force and energy while minimizing or reducing edge effects. These effects comprise both electrical and pressure edge effects describe herein.

Figure 11:
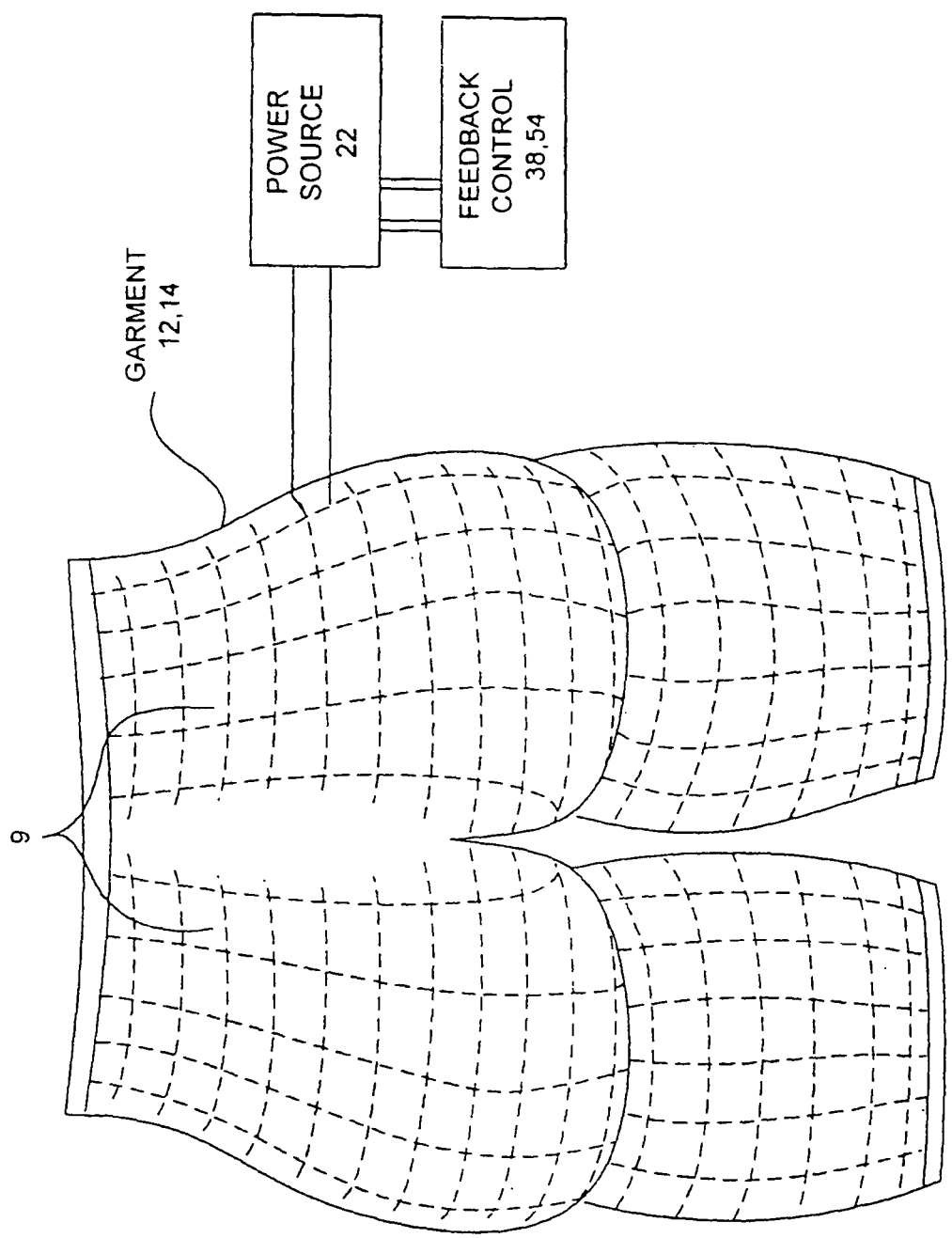
FIG. 11 illustrates a template in the form of a garment.

In various embodiments, template 12 can be configured to treat a variety of human anatomical structures (both internal and external) and accordingly, can have a variety of different forms and shapes. One embodiment of such a form is a garment that is illustrated in FIG. 11. An energy source 22 can be directly incorporated into the fabric of a tight fitting garment or inserted as a heating or RF electrode pad into a pocket of the garment. Another example of a garment is a tight fitting bra that extends over the arm and waistline with zone control that provides contraction of the skin of the breast, arms, and waistline to a variable amount to create a desired three-dimensional figure. Functional remodeling of collagen containing structures includes a variety of different applications for aesthetic remodeling.

Figure 12A:
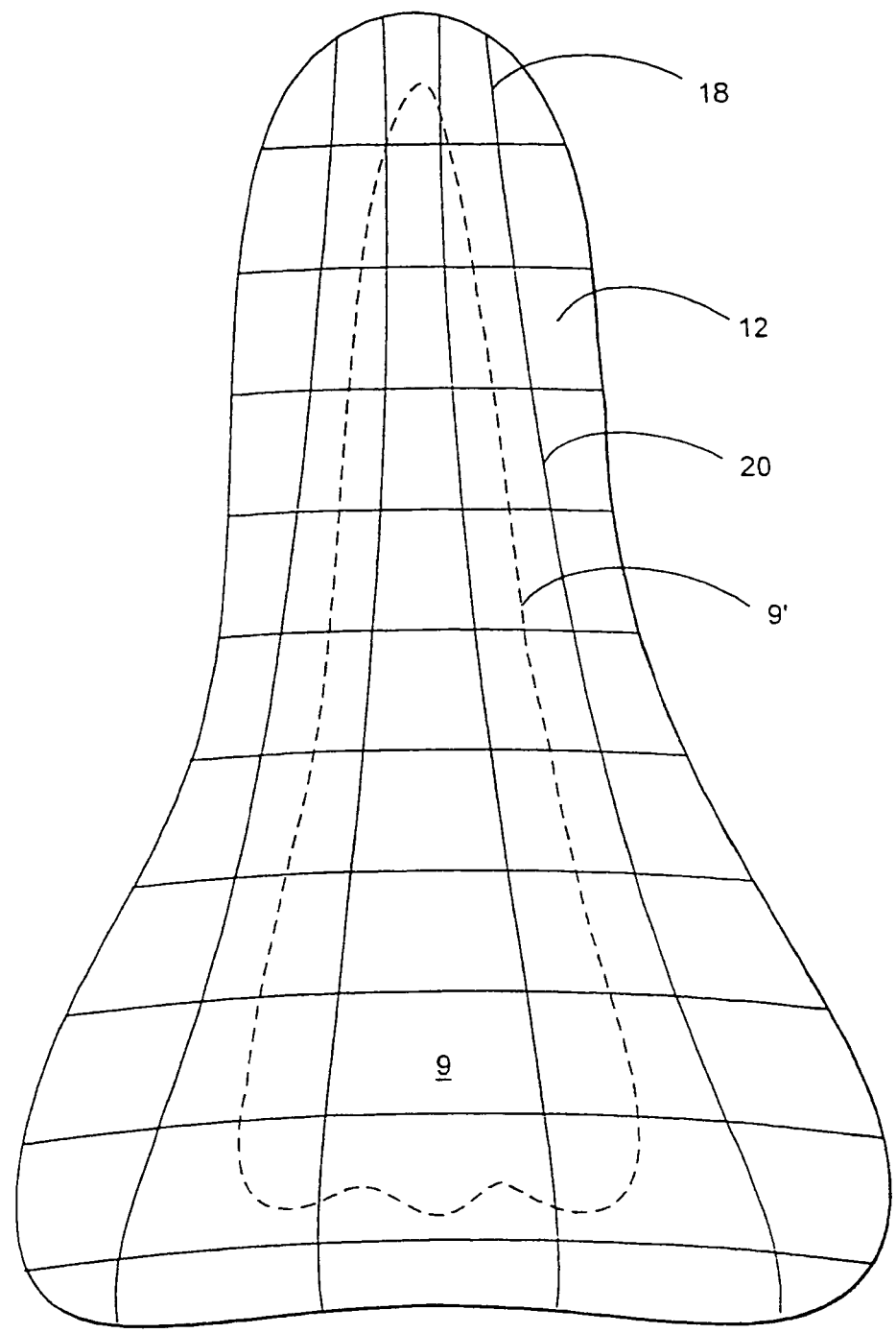
FIG. 12(a) illustrates a template that is positioned over a nose.
Figure 12B:
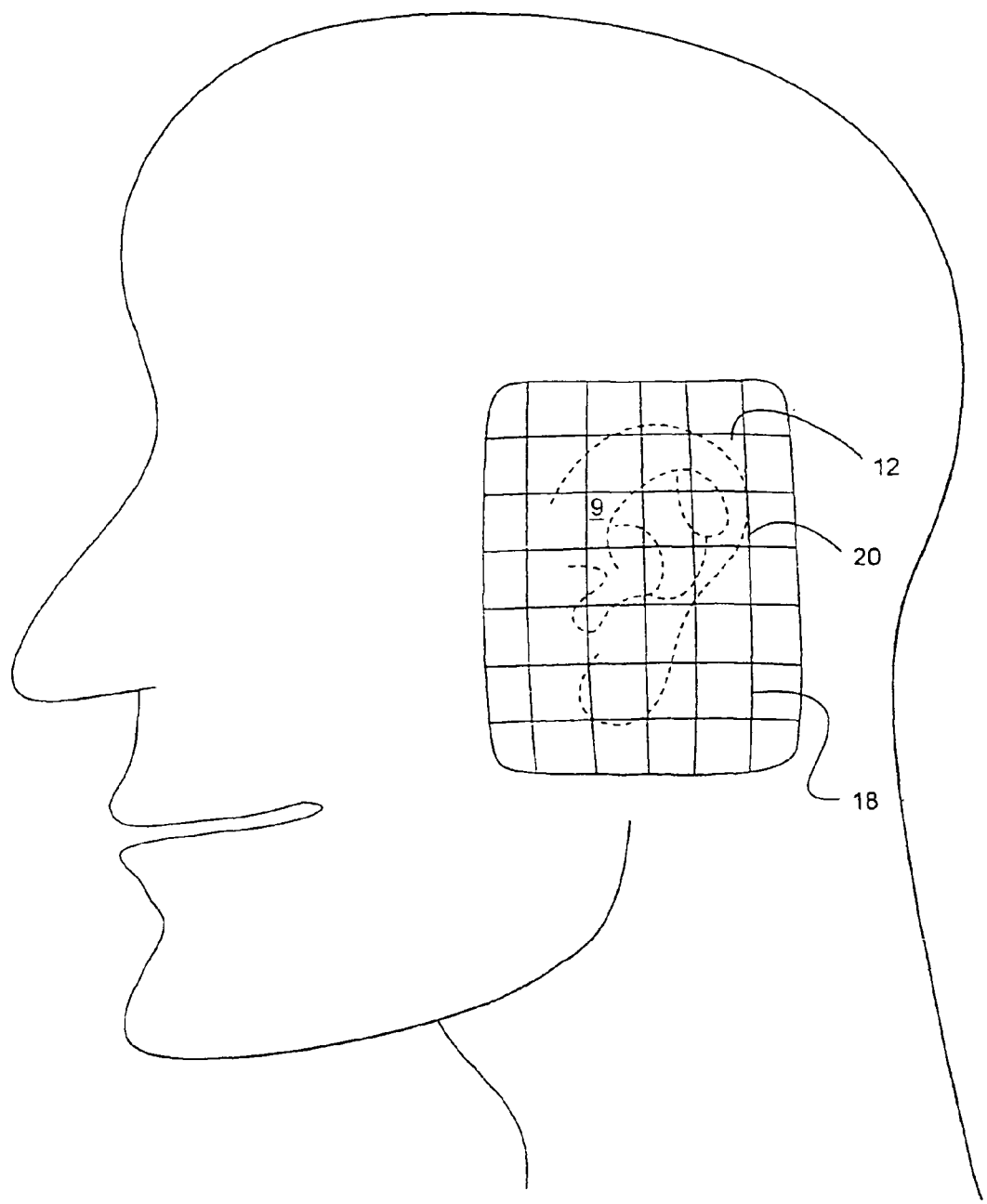
FIG. 12(b) illustrates a template that is positioned over an ear.
Figure 13:
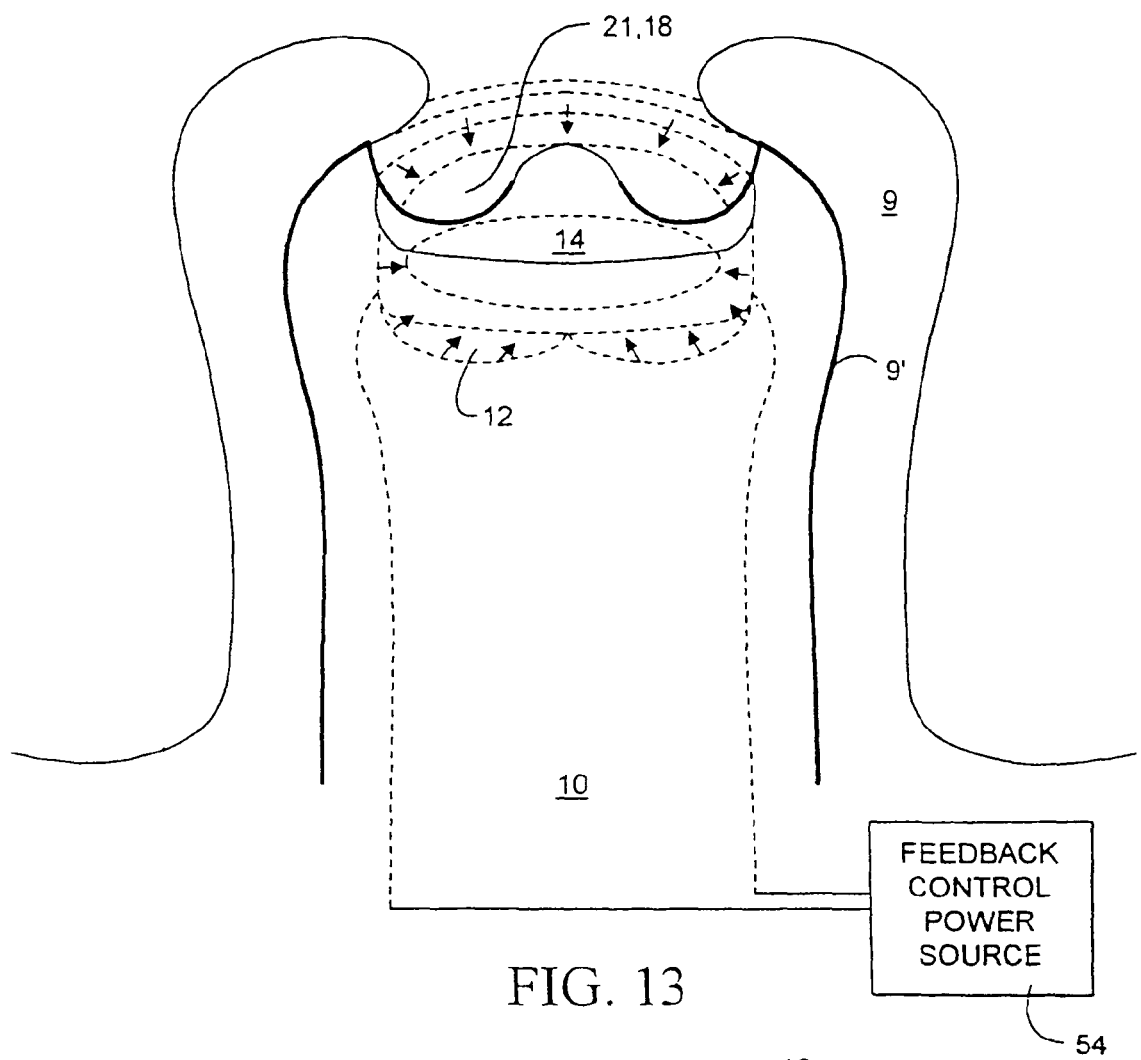
FIG. 13 is a perspective view of a template that is useful in treating the cervix.
Figure 14:
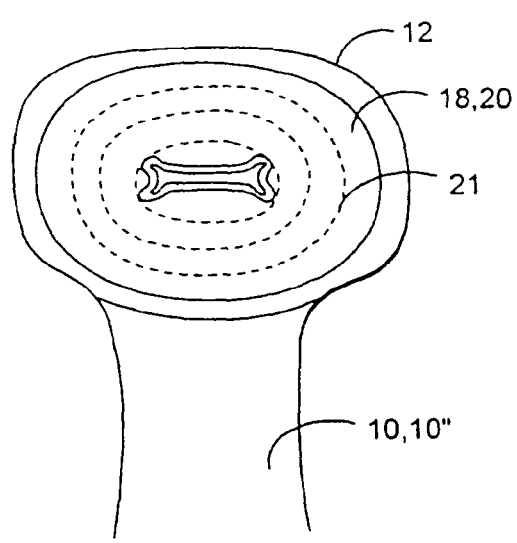
FIG. 14 is a cross-sectional view of the template of FIG. 13.

As shown in FIGS. 12(a) and 12(b), in various embodiments template 12 can be a garment positioned over the nose, around the ear, or other facial structure. Template 12 can also be applied for functional purposes. Referring now to FIGS. 13 and 14, pre-term cervical dilation can be treated with a template 12 that is configured to have the impression or form of a "competent" cervix. The cervical template 12 creates vectors that contract the circumference of the cervix. The incorporated energy delivery device 18 contracts the native matrix and induces scar collagen. The dilated cervical OS is tightened and the entire cervix is strengthened. Energy delivery device 18 can be incorporated into template 12 which can be the cervical conformer and inserted as a vaginal obturator. It will be appreciated that template 12 can be utilized for other functional treatments.

Figure 15A:
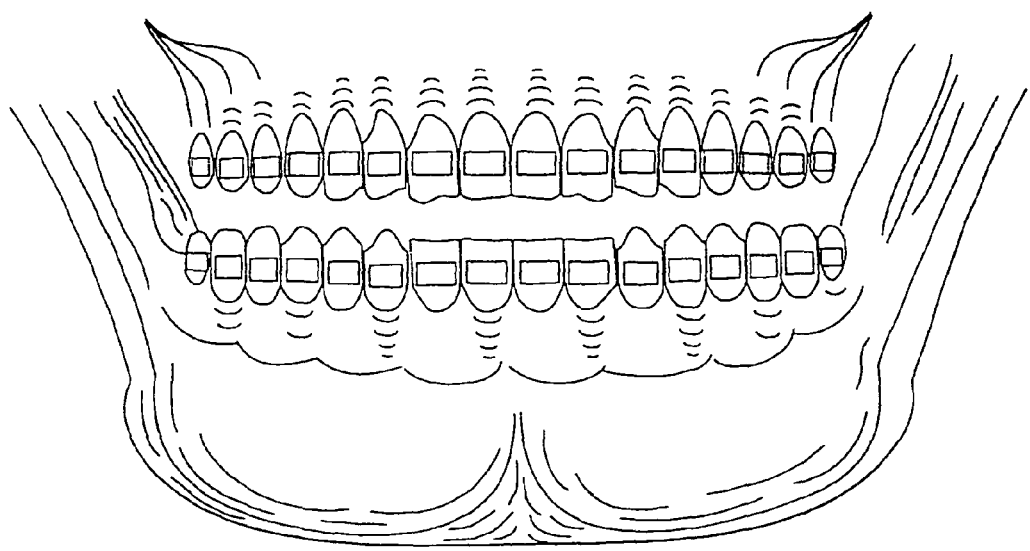
FIG. 15(a) is a front view of an orthodontic appliance that includes RF electrodes.
Figure 15B:
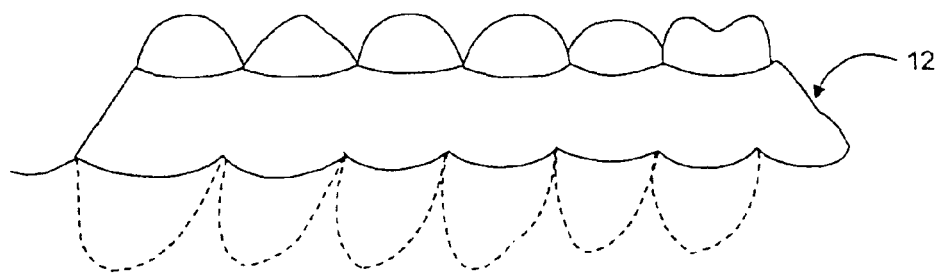
FIG. 15(b) is perspective view of an orthodontic appliance template of the device of FIG. 1.
Figure 15C:
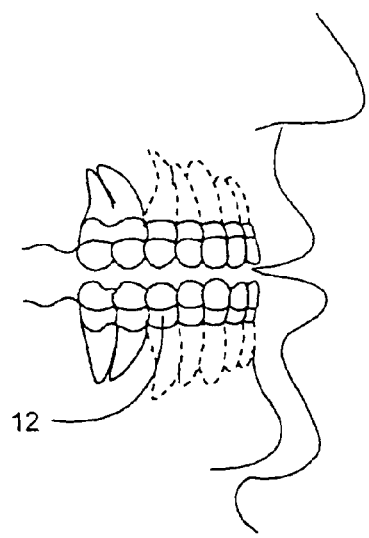
FIG. 15(c) is cross-sectional view of the template of FIG. 15(b).

In another embodiment, template 12 is a functional appliance that may be non-conforming and can be separate or incorporated with the energy delivery device 18. Orthodontic braces that are designed in conjunction with energy delivery device 18 are used to remodel dental collagen and apply rotation and inclination vectors on the neck of the tooth which is devoid of enamel. In FIG. 15(a) orthodontic braces are coupled to RF electrodes and associated power source. The orthodontic braces function as a non-conforming force application surface that is coupled to incorporated RF electrodes. FIGS. 15(b) and 15(c) illustrates a orthodontic appliance that is a conforming template 12 coupled to RF electrodes. As a consequence, orthodontic correction is more rapidly achieved than current modalities that employ only mechanical forces.

Orthodontic correction can also be achieved with a conforming template 12 that is the corrected impression of the patient's dentition.

For orthopedic applications, an external fixation device is used as a non-conforming functional appliance. This appliance is used in tandem with an energy source device, including but not limited to RF electrodes, that remodels the collagen of the callus tissue. More accurate alignment of osteotomy and fracture sites are possible with either a conforming or nonconforming brace that is used in tandem or is directly incorporated into energy delivery device 18. Improved range of motion of contracted joints and correction of postural (spinal) deformities can be achieved with this combined approach.

The ability to remodel soft tissue in anatomical structures other than skin can be dependent upon the presence of preexisting native collagen. In tissue devoid or deficient of native collagen, energy and/or force and can be delivered to cause an induction or formation of scar collagen. Template 12 can be used to remodel the subcutaneous fat of hips and thighs in addition to the tightening of the skin envelope. The convolutions of the ear cartilage can be altered to correct a congenital prominence. The nasal tip can be conformed to a more esthetically pleasing contour without surgery.

Template 12 can be used with any modality that remodels collagen including but not limited to the applications of heat, electromagnetic energy, force and chemical treatment, singularly or in combination. In addition to RF (e.g. molecular) remodeling of collagen, cellular modalities that invoke the wound healing sequence can be combined with a conforming esthetic template. Thermal and chemical treatments (e.g. glycolic acid) induce a low-level inflammatory reaction of the skin. Scar collagen induction and fibroblastic (cellular) contraction are directed into converging and diverging vectors by a conformer that produces a smoother and tighter skin envelope. In addition to achieving a smoother and tighter integument, the texture of the skin is also improved with this remodeling process. Older or less compliant skin has a greater number of intermolecular crosslinks in the dermal collagen than younger skin. Scar collagen induction with cleavage of crosslinks will produce a softer and more compliant skin envelope.

Cutaneous applications for apparatus 8 and/or embodiments of patient feedback methods can include one or more of the following: (i) Non invasive skin rejuvenation with the replacement of elastoic sun damaged collagen in the dermis with nascent scar collagen, (ii) on invasive hair removal, without epidermal burning, (iii) Hair growth with intracellular induction of the hair follicle, (iv) Non invasive reduction of sweating and body odor, (v) Non invasive reduction of sebaceous gland production of oil as a treatment of an excessively oily complexion, and (vi) Non invasive treatment of dilated dermal capillaries (spider veins). Non-cutaneous applications for apparatus 8 can include the following: (i) Non invasive treatment of preterm delivery due to an incompetent cervix, (ii) Non invasive treatment of pelvic prolapse and stress incontinence, (iii) Non invasive treatment of anal incontinence, (iv) Non invasive creation of a continent ileostomy or colostomy, and (v) Non invasive (or minimally invasive through an endoscope) correction of a hernia or diastasis.

Figure 16:
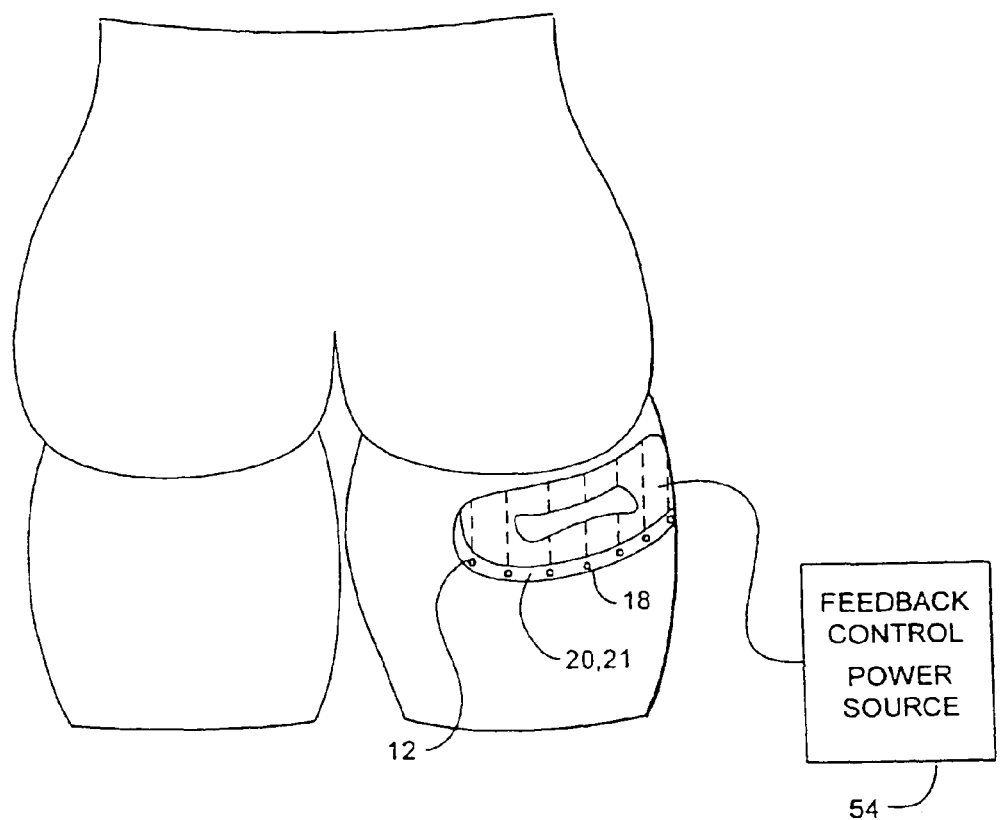
FIG. 16 is a perspective view illustrating a template made of a semisolid material that becomes more conforming to underlying soft tissue upon the application of a mechanical force.
Figure 17:
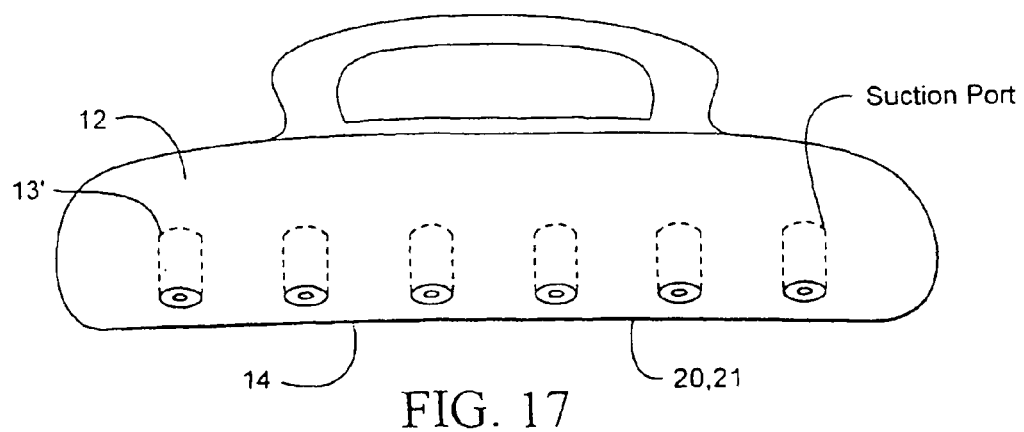
FIG. 17 illustrates a template with an adherent or suction mechanical force delivery surface that permits manual manipulation of skin and soft tissue structures.

Referring now to FIGS. 16 and 17, template 12 can be stationary or mobile. A hand held conforming template 12 that is mobile provides the practitioner with greater flexibility to remodel the collagen matrix and surrounding tissue. Pressure (e.g. force) and impedance changes can serve as a guide for the manual application of template 12. A hand held template 12 with an incorporated energy source 22 and energy delivery devices 18 may be applied over a conductive garment that provides three dimensional conformance to the treatment area. Less accessible areas can be remodeled with this particular device. In one embodiment shown in FIG. 16, template 12 is made of a semi-solid material that conforms a lax skin envelope to an underlying soft tissue structure. The semi-solid material allows for the customized shaping of force application surface 14 and reduces the need for precise fabrication of an esthetic template. Suitable semi-solid materials include compliant plastics that are thermally and electrically conductive. Such plastics include but are not limited to silicone, polyurethane and polytetrafluoroethylene coated or otherwise embedded with an electrically or thermally conductive metal such as copper, silver, silver chloride, gold, platinum or other conductive metal known in the art.

Controlled remodeling of collagen containing tissue can be accomplished using an electromagnetic device that lengthens or contracts the matrix with a minimum of cell necrosis. Energy delivery devices suited to this purpose include one or more RF electrodes. Accordingly, energy delivery device 18 can include a plurality of RF electrodes with or without insulation. The non-insulated sections of the RF electrodes collectively form template energy delivery surface 20. In a similar manner, in various other embodiments microwave antennas, optical waveguides, ultrasound transducers and energy delivery or energy remove fluids can be used to form template energy delivery surface 20. Individual electrodes 18 and the like can be multiplexed and to provide selectable delivery of energy.

Figure 18A:
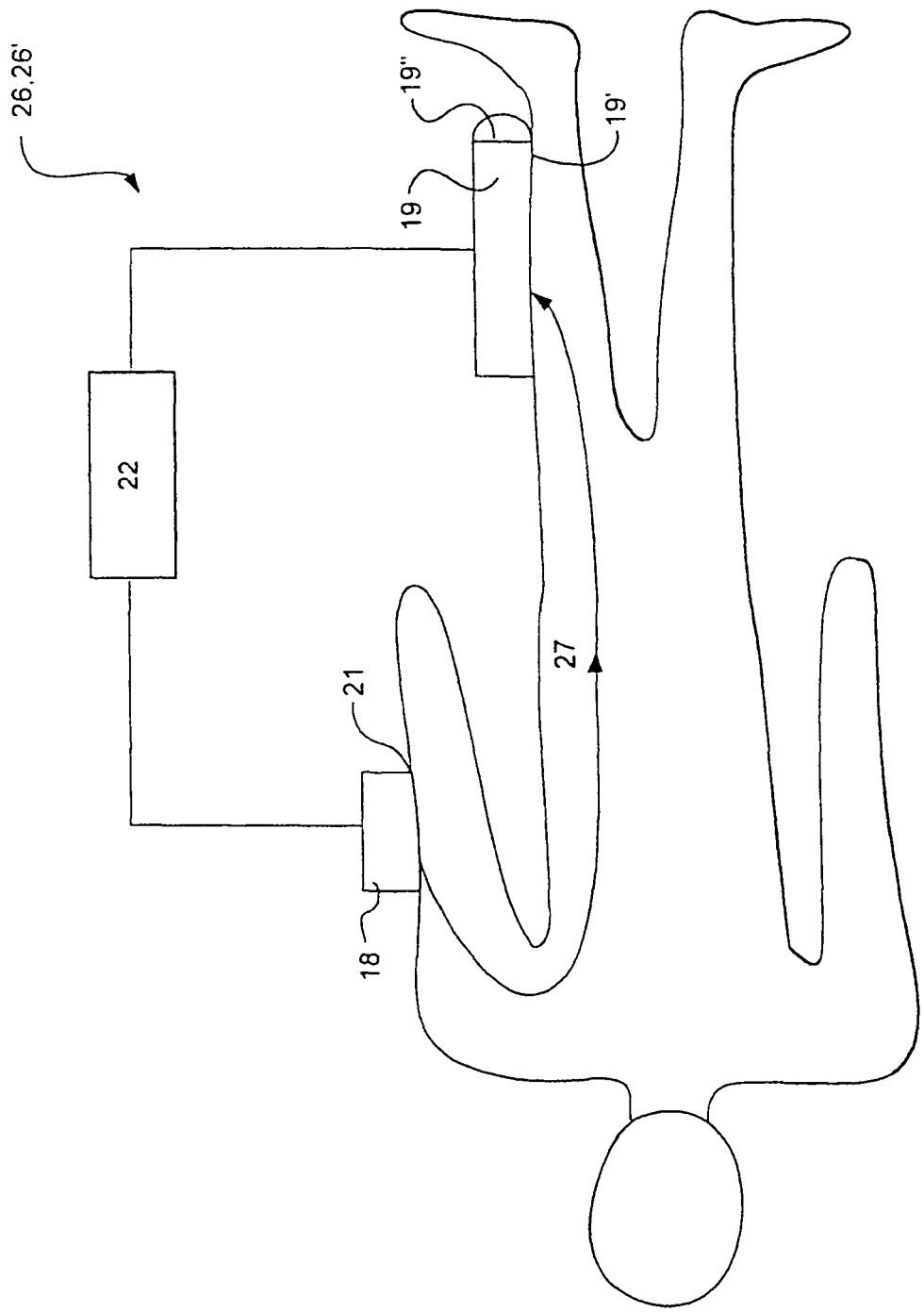
FIG. 18a is a schematic diagram illustrating a monopolar RF energy system including the use of a ground pad electrode.
Figure 18B:
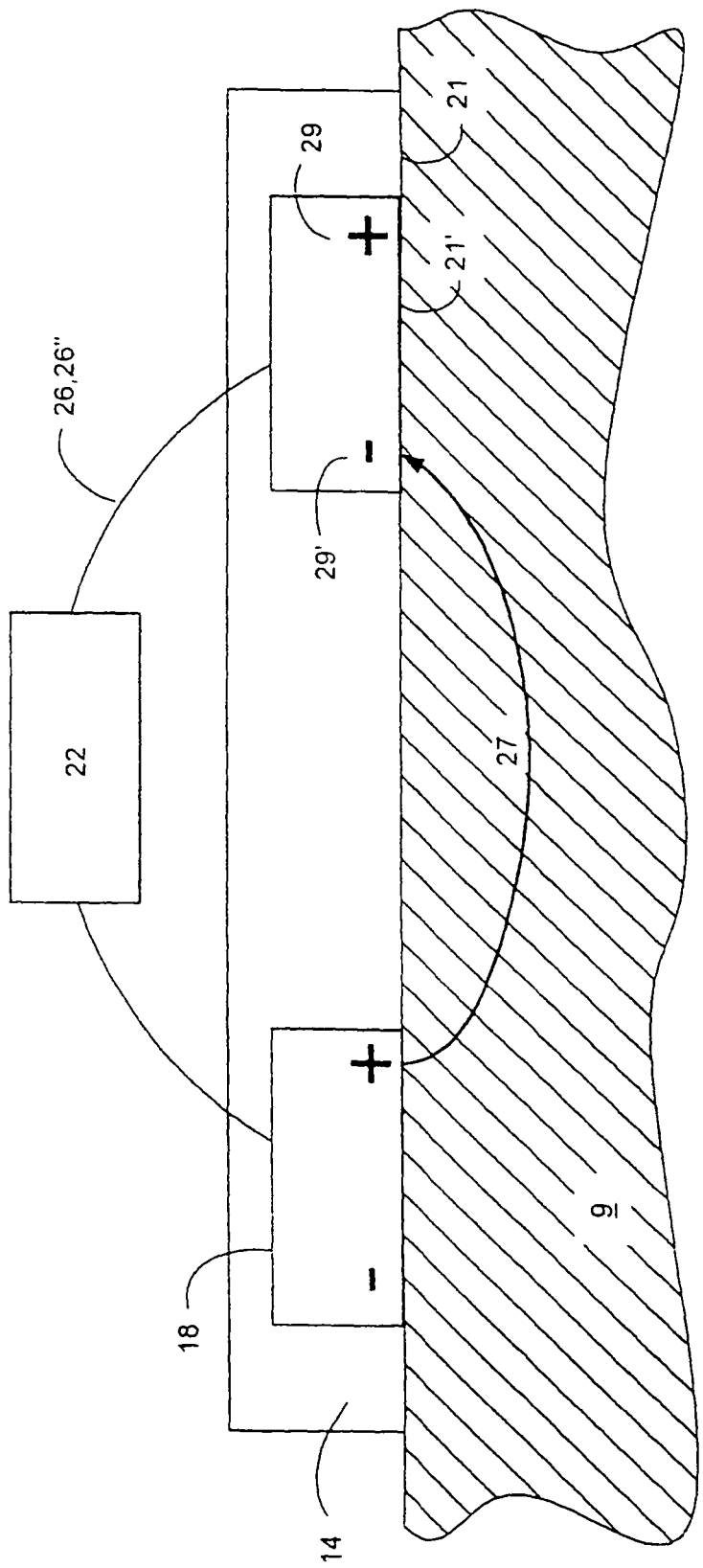
FIG. 18b is a schematic diagram illustrating a bipolar RF energy system and bipolar RF energy electrode.

Referring now to FIGS. 18a and 18b, when energy delivery device 18 is an RF electrode, energy source 22 is a RF generator well known in the art, together they can comprise an RF energy delivery system 26. RF energy system 26 can be operated in either a bipolar or a monopolar configuration as is well known in the art of electro-surgery. Also RF energy delivery system 26 can be configured to be used in one or more embodiments of tissue treatment with patient feedback described herein. For example, the delivery system can include power setting that can be calibrated to particular levels of patient thermal/pain sensation.

A monopolar RF energy system 26' tends to behave as a series circuit if tissue surface impedance is uniform. In various monopolar embodiments, tissue surface impedance can both be reduced and made more uniform by hydration of the skin surface and/or underlying tissue. This in turn can reduce resistive heating of the skin surface. Such a monopolar system configuration will be less likely to produce high current density shorts than a bipolar system. The resulting electrical field will also have greater depth if heating of subjacent tissues is desired. It is predicted that the application of uniform compressive forces to the skin with monopolar RF systems can be used to actively remodel the dermis instead of being a factor that causes a combined edge effect at the skin surface. In addition, a monopolar system 26' can be configured to provide a choice of two treatment surfaces. Another embodiment of a monopolar system 26' involves the combination of RF lipolysis at the active electrode with skin contraction at the passive electrode tissue interface 19' and surrounding tissue.

As shown in FIG. 18a, in a monopolar RF energy system 26', current flows from RF energy source 22 to the RF electrode 18 also known as the active electrode 18, into the patient and then returns back to RF generator 22 via a second electrode 19 known as a passive electrode 19, return electrode 19, or ground pad 19 which is in electrical contact with the skin of the patient (e.g. the thigh or back). In various embodiments, RF electrode 18 can be constructed from a variety of materials including but not limited to stainless steel, silver, gold, platinum or other conductor known in the art. Combinations or alloys of the aforementioned materials may also be used.

Ground pad 19 can be configured to serve to both provide a return path for electrical current 27 from electrode 18 to electrical ground and disperse the current density at ground pad tissue interface 19' to a sufficiently low level so as to prevent a significant temperature rise and or thermal injury at interface 19'. Ground pad 19 can be either a pad or a plate as is well known in the art. Plates are usually rigid and made of metal or foil-covered cardboard requiring use of a conductive gel; pads are usually flexible. Suitable geometries for ground pad 19 include circular, oval or rectangular (with curved corners) shapes. Heating at tissue interface 19 can be reduced in various embodiments in which ground pad 19 has a radial taper 19". Ground pad 19 may also contain a heat transfer fluid or be coated with a thermally conductive material to facilitate even distributions of heat over the pad, reduce hot spots and reduce the likelihood of thermal injury at tissue interface 19'. Also ground pad 19 and the interface 19' between ground pad 19 and the patient is of sufficiently low impedance to prevent the phenomena of current division, or electrical current flowing to ground by an alternate path of least resistance and potentially burning of the patients skin at an alternate grounded site on the patient. Furthermore, ground pad 19 is of sufficient surface area with respect to both the patient and with RF electrode 18 such that the return current is dispersed to a level that the current density at interface 19' is significantly below a level that would cause damage or any appreciable heating of tissue at interface 19' or any other part of the body except in the area 21 in immediate proximity to RF electrode 18. In various embodiments, the surface area of ground pad 19 can range from 0.25 to 5 square feet, with specific embodiments of 1, 2, 3 and 4 square feet.

In alternative embodiments, grounding pad 19 can be used as the surface treatment electrode. That is, it functions to produce a heating effect at tissue interface 19' in contact with ground pad 19. In these embodiments, the surface area of ground pad 19 is small enough relative to both the patient and/or RF electrode 18, such that ground pad 19 acts as the active electrode. Also, RF electrode 18 has a large enough surface area/volume (relative to the patient) not to produce a heating effect at energy delivery surface 20. Also, ground pad 19 is positioned at the desired treatment site, while RF electrode 18 is electrically coupled to the patients skin 9' a sufficient distance away from return electrode 19 to allow sufficient dispersion of RF current 27 flowing through the patient to decrease the current density and prevent any heating effect beside that occurring at pad interface 19'. In this embodiment, fluid delivery device 13 can be incorporated into the ground pad 19. The subjacent skin can be hydrated to reduce resistive heating and provide a more uniform impedance that can avoid parallel shorts through localized areas of low impedance. At a distant tissue site, active electrode 18 is applied either topically cooled or inserted percutaneously with a sheathed electrode that avoids burning of the skin. The active electrode 18 will be typically positioned in the subcutaneous fat layer. The fat is injected with a saline solution to lower current density which will in turn diminish burning of the subcutaneous tissue. If significant burning of the subcutaneous tissue occurs, this site can be positioned on the lower abdomen for an aesthetic excision.

Referring now to FIG. 18b, in a bipolar RF energy system 26", individual RF electrodes 18 have positive and negative poles 29 and 29'. Current flows from the positive pole 29 of one electrode to its negative pole 29', or in a multiple electrode embodiment, from the positive pole 29 of one electrode to the negative pole 29' of an adjacent electrode. Also in a bipolar embodiment, the surface of a soft or conformable electrode 18 is covered by a semiconductive material describe herein. Also in a bipolar system it is important that the force applied by force applications surface 14 to tissue interface 21 be limited to that amount necessary only to achieve and maintain contact with the skin. This can be achieved through the use of a feedback control system described herein.

In various embodiments, RF electrode 18 can be configured to minimize electromagnetic edge effects that cause high concentrations of current density on the edges of the electrode. By increasing current density, edge effects can cause hot spots in tissue interface 21 or on the edges of the electrode resulting in thermal damage to the skin and underlying tissue at or near tissue interface 21. In an embodiment, edge effects can be minimized by moving the electrode 18 in response to patient feedback to reduce overheating at the electrode edges. In one embodiment the positioning of electrode 18 can be mediated by inputs from one or more temperature measurement sensors (e.g., sensors 23) at the target tissue site.

Figure 19A:
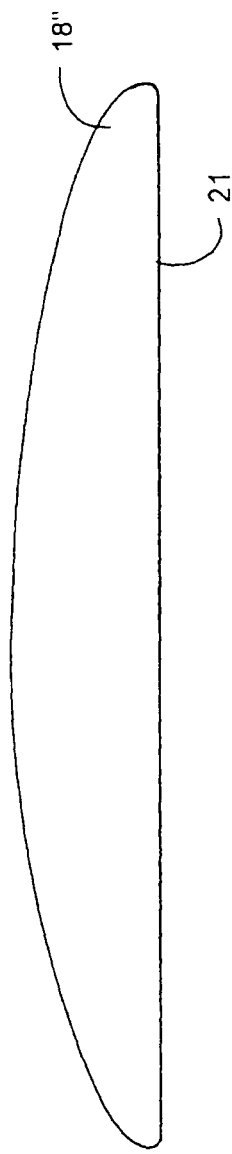
FIGS. 19a and 19b are later views illustrating geometric embodiments of an RF electrode configured to reduce edge effects.
Figure 19B:

Referring now to FIGS. 19a and 19b, in other embodiments the reduction of edge effects can be accomplished by optimizing one or more of the geometry, design and construction of RF electrode 18. Electrode geometries suited for reducing edge effects and hot spots in RF electrode 18 and tissue interface 21 include substantially circular and oval discs with a radiused edge 18". For the cylindrical configuration edge effects are minimized by maximizing the aspect ratios of the electrode (e.g. diameter/thickness). In a specific embodiment, edge effects can be also reduced through the use of a radial taper 43 in a circular or oval shaped electrode 18. In related embodiments, the edges 18" of electrode 18 are sufficiently curved (e.g. have a sufficient radius of curvature) or otherwise lacking in sharp corners so as to minimize electrical edge effects.

Figure 20A:
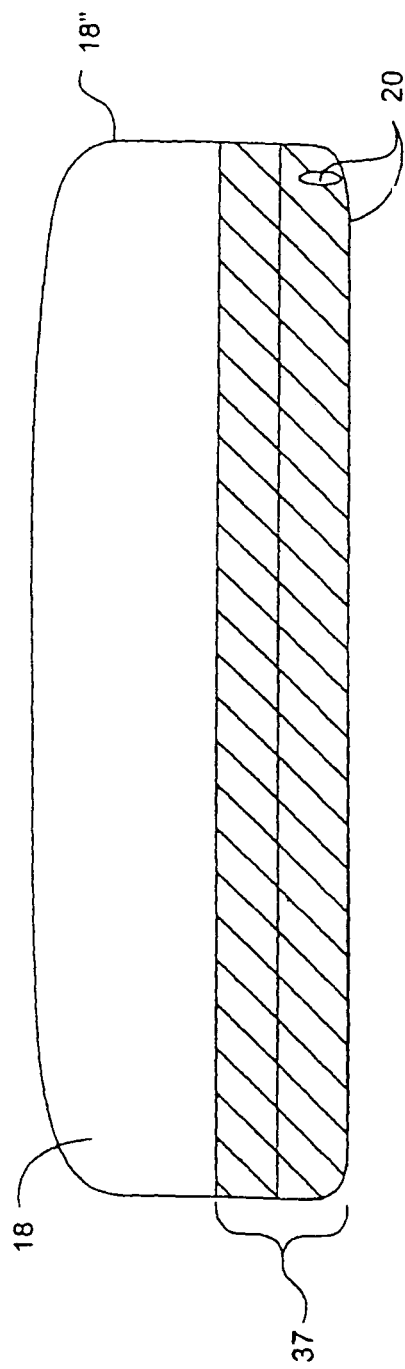
FIG. 20a is a lateral view illustrating the use of conforming layers with an RF electrode configured to reduce edge effects.
Figure 20B:
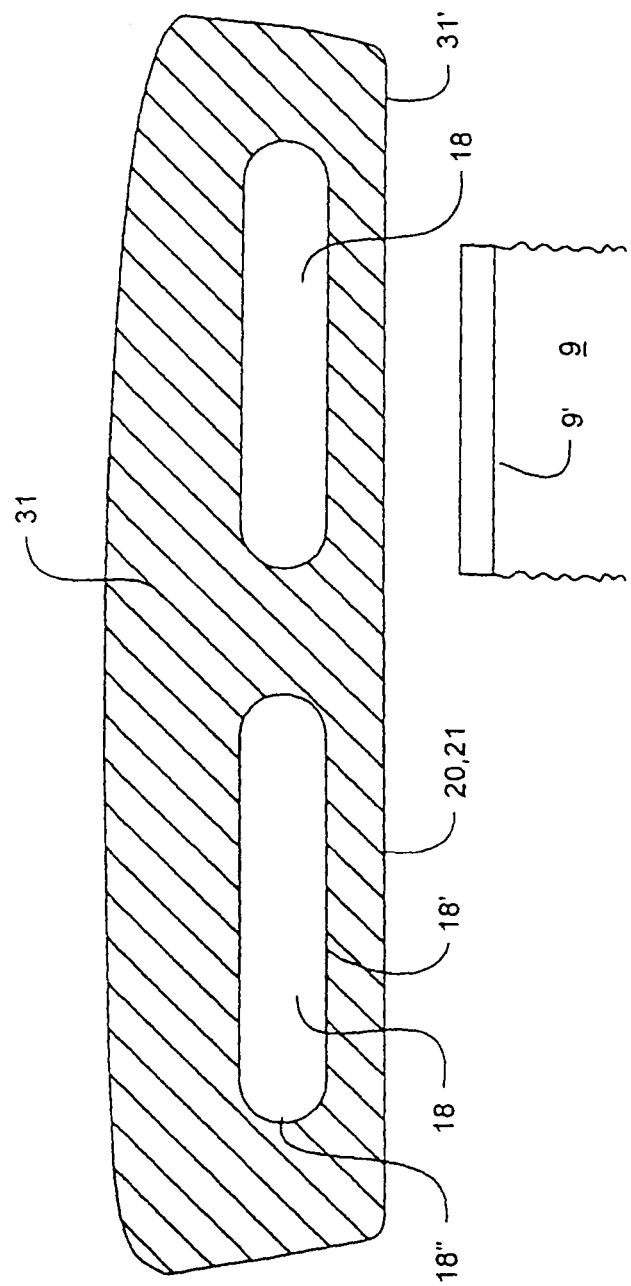
FIG. 20b is a lateral view illustrating the use of semiconductive material template with an RF electrode configured to reduce edge effects.

Referring now to FIGS. 20a and 20b, there are several other embodiments of RF electrode 18 that can reduce edge effects. One embodiment illustrated in FIG. 20a, involves the use of a soft or conforming electrode 18 that has a soft or conforming layer 37 over all or a portion of its energy delivery surface 20. Conforming layer 37 can be fabricated from compliant polymers that are embedded or coated with one or more conducting materials (in the case of monopolar embodiments described herein) including, but not limited to silver, silver chloride, gold or platinum.

In bipolar embodiments, conforming layer 37 is coated or otherwise fabricated from semiconductive materials described herein. The polymers used are engineered to be sufficiently compliant and flexible to conform to the surface of the skin while not protruding into the skin, particularly along an edge of the electrode. The conductive coatings can be applied using electro-deposition or dip coating techniques well known in the art. Suitable polymers include elastomers such as silicone and polyurethanes (in membrane or foam form) and polytetrafluoroethylene. In one embodiment the conformable template surface 37 will overlap the perimeter 18" of electrode 18 and cover any internal supporting structure. In another embodiment, the entire surface 20 of electrode 18 is covered by conforming layer 37.

Referring now to FIG. 20b, in various embodiments, particularly those using an array of RF electrodes 18, edge effects at the electrode tissue interface 21 can be reduced by the use of a semiconductive material template 31 or substrate 31 located between or otherwise surrounding electrodes 18. In various embodiments, the conductivity (or impedance) of semiconductive substrate 31 can range from $10^{-4}$ to $10^{-3}$ (ohm-cm).$^{-1}$, with specific embodiments of $10^{-4}$ and 1 (ohm-cm)$^{-1}$. The conductivity (or impedance) of substrate 31 can also vary in a radial 31' or longitudinal direction 31" resulting in an impedance gradient.

In various embodiments, surrounding means that substrate 31 is in contact with and/or provides an electrical impedance at all or a portion of electrode 18, including but not limited to, only one or more surfaces 18', and one or more edges 18". In this and related embodiments substrate 31 is an insulating material with a conductivity of 10$^{-6}$ (ohm-cm)$^{-1}$ or lower.

In an embodiment, the impedance of the semi-conductive template 31 can be variable in relation to electrode position within template. The template impedance has a specific pattern that reduces hot spots on the tissue surface 9' by reducing current density at locations more likely to have higher current densities such as edges of individual electrodes and the array itself. In one embodiment, the impedance of template 31 is larger at the electrode perimeter or edges 18". Also in various embodiments, electrode shape and topographical geometry are incorporated into the variable impedance topography of semiconductive template 31 between the electrodes. As a result, a more uniform current density is achieved that prevents or reduces thermal damage of tissue at or nearby tissue interface 21. The specific electrode shape, geometry and distribution pattern on the variable impedance template 31 as well as the pattern of impedance variation over the template surface 31' can be modeled and designed using a software simulation (such as a finite element analysis program) that is adapted for the overall three-dimensional contour of a specific device.

In addition to electromagnetic edge effects described herein, pressure edge effects may also result with the use of a rigid materials in force application surface 14 that tend to concentrate force on the edges of force application surface 14 and/or electrode 18. Such force concentrations can damage skin and underlying tissue and also cause hot spots due to increased RF energy delivery and/or increased heat transfer at the areas of force concentration.

Figure 21:
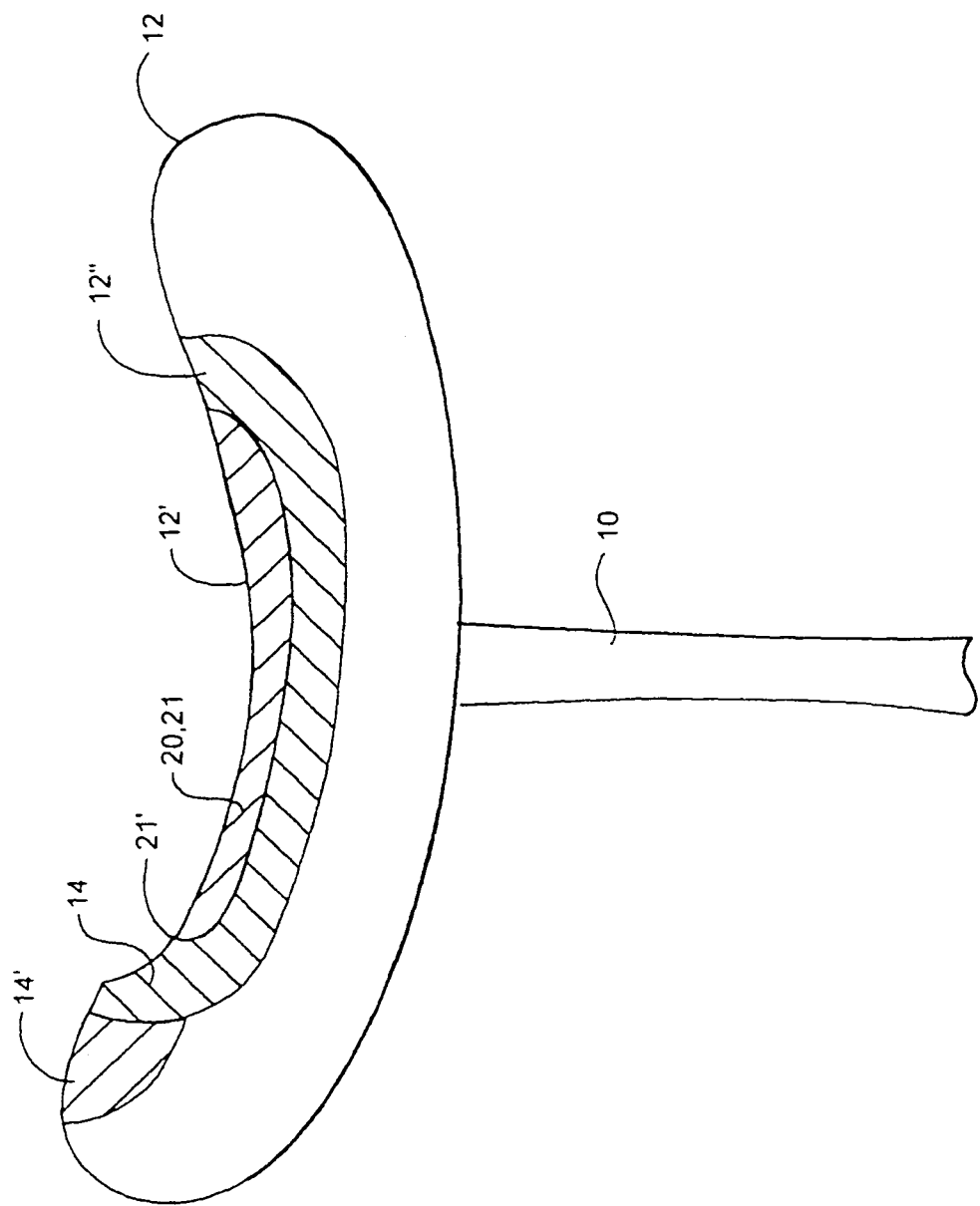
FIG. 21 is a lateral view illustrating the use of template with a conformable surface.

Referring now to FIG. 21, to eliminate these force concentrations and their effects, the shape and material selection, of template 12 can be configured to provide a cushioned or conformable template surface or layer 12' that is incorporated into the framework of template 12 and force application surface 14 (i.e., the conformable template surface will overlap the perimeter and encompass any internal supporting member). In a specific embodiment, the entire surface of template 12 and/or force application surface 14 is covered by a conformable layer 12' (similar to conformable layer 37) that is made of a semiconductive (for bipolar applications) or conductive (for monopolar applications) material that avoid enhanced pressure or electrical edge effects described herein. In another embodiment template 12 can have a laminated or layered construction whereby conformable layer 12' is joined or otherwise coupled to an inner rigid layer 12" (via adhesive bonding, ultrasonic welding or other joining method known in the art). Rigid layer 12 facilitated the in the transmission/application of force 17 to tissue but does not contact tissue itself.

In various embodiments, conformable layer 12' can be constructed of conformable materials with similar properties as conformable layer 37. Materials with suitable conformable properties include various conformable polymers known in the art including, but not limited to polyurethanes, silicones and polytetrafluoroethylene. The polymer materials can be coated with conductive materials such as silver, silver chloride, and gold; or semiconductive coatings such as vapor-deposited germanium (described in U.S. Pat. No. 5,373,305 which is incorporated by reference herein) using electro/vapor deposition or dip coating techniques, or constructed with semiconductive polymers such as metallophthalocyanines using polymer processing techniques known in the art. In various embodiments, the thickness and durometer of polymers used for force application surface 14 and/or RF electrode 18 can be further configured to: i) produce a uniform distribution of applied force across the electrode tissue interface 21 or ii) produce a gradient in stiffness and resulting applied force 17 across energy delivery surface 20. In an embodiment, force applications surface 14 and/or energy delivery surface 20 are configured to have maximum applied force 17 at their respective centers and decreasing applied force moving outward in the radial direction. In other embodiments, force application surface 14 can be engineered to produce varying force profiles or gradients at tissue interface 21 with respect to radial direction of template 12, force applications surface 14, or energy delivery surface 20. Possible force profiles include substantially linear, stepped, curved, logarithmic with a minimum force at tissue interface edge 21' or force application edge 14' and increasing force moving in an inward radial direction. In a related embodiment, gradients in bending and compressive stiffness can be produced solely by varying the thickness of force application surface 14, electrode 18 or energy delivery surface 20 in their respective radial directions. In an embodiment, force application surface 14 and/or electrode 18 have a maximum thickness and bending stiffness at their respective centers with a tapered decreasing thickness (and corresponding stiffness) moving out in their respective radial directions.

In various embodiments, monitoring of both active electrode 18 and passive electrode 19 may be employed to prevent or minimize unwanted currents due to insulation breakdown, excessive capacitive coupling or current division. An active electrode monitoring system 38 shown in FIG. 22, uses a monitoring unit 38' to continuously monitor the level of stray current 27' flowing out of electrode 18 and interrupts the power should a dangerous level of leakage occur. Stray currents 27' include currents due to capacitive coupling and/or insulation failure of electrode 18. In various embodiments monitoring unit 38' can be integrated into or otherwise electronically coupled with a control system 54 and current monitoring circuitry described herein. Monitoring system 38 may also be configured to conduct stray current from the active electrode back to the RF generator and away from patient tissue. Monitoring system 38 can also be configured to be used with one or more forms of patient feedback described herein including biometric feedback.

Monitoring unit 38' can comprise electronic control and measurement circuitry for monitoring impedance, voltage, current and temperature well known in the art. Unit 38' may also include a digital computer/microprocessors such as an application specific integrated circuit (ASIC) or a commercial microprocessor (such as the Intel® Pentium® series) with embedded monitoring and control software and input/output ports for electrical connections to sensors 23 and other measurement circuitry, to active electrode 18, passive electrode 19, RF generator 22 and other electrical connections including connections to the patient and ground. Monitoring unit 38' may also be incorporated into RF generator 22.

In another embodiment monitoring system 38 is configured as a passive electrode monitoring system 39' that is used to monitor the passive electrode 19 and shut down current flow from RF generator 22 should the impedance of passive electrode 19 or interface 19' becomes too high or temperature at the interface 19' rise above a set threshold. In these embodiments, passive electrode 19 is a split conductive surface electrode (known in the art) which can measure impedance at the interface 19' between patient tissue and the patient return electrode itself and avoid tissue burns. Prevention of pad burns is also facilitated by the coupling of temperature monitoring, impedance and/or contact sensors 23 (such as thermocouples or thermistors) to pad 19 and a monitoring unit 39' (which can be the same as monitoring unit 38' and likewise coupled to control system 54). Contact or impedance sensors 23 allows unit 39' to monitor the amount of electrical contact area 19''' of pad 19 that is in electrical contact with the skin and shut down or otherwise alarm should the amount of contact area fall below a minimum amount. Suitable contact sensors include pressure sensors, capacitance sensors, or resistors in suitable ranges and values known in the art for detecting electrical contact with the skin.

Figure 22:
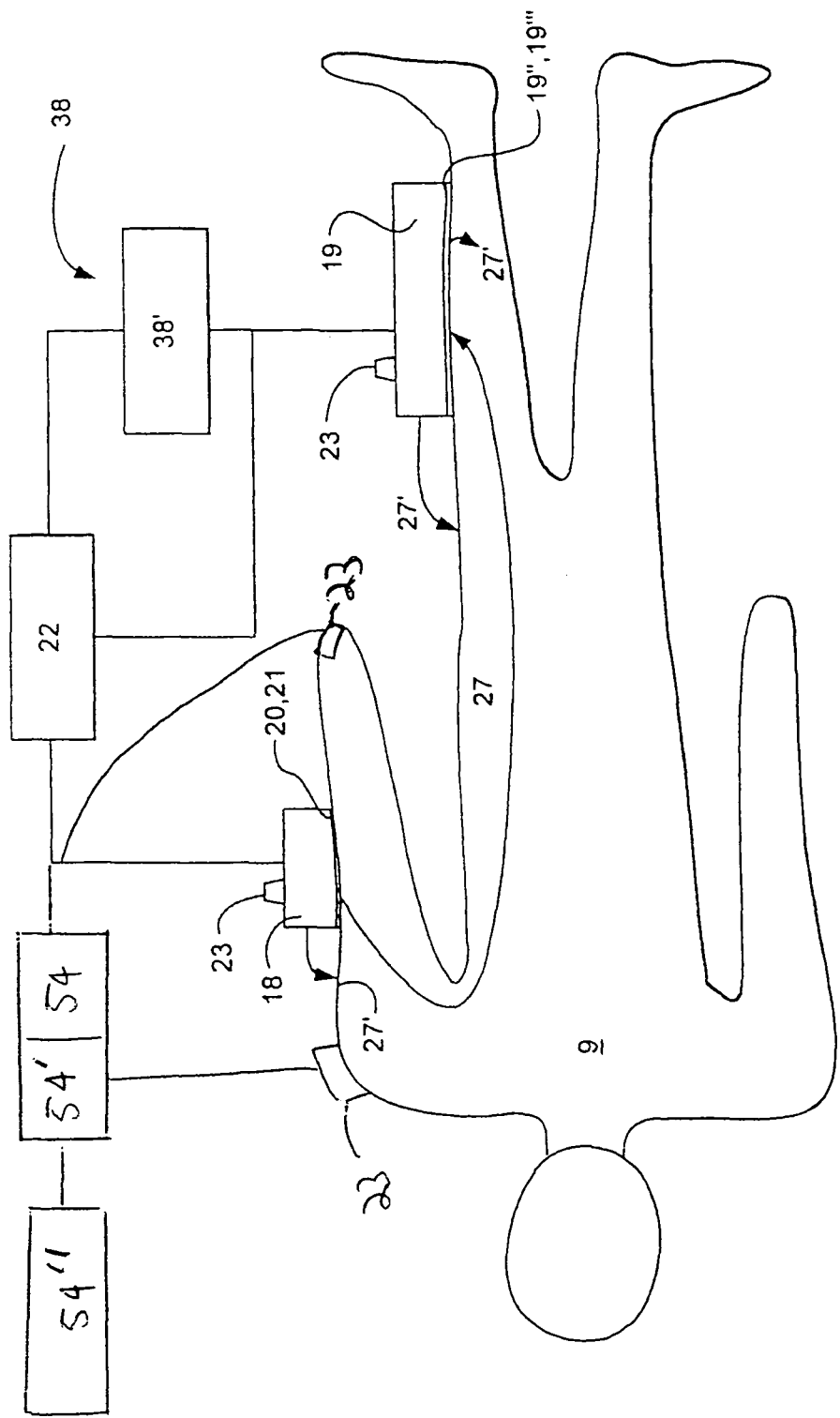
FIG. 22 is a schematic diagram illustrating the use of a monitoring system to monitor stray current from the active or the passive electrode.
Figure 23:
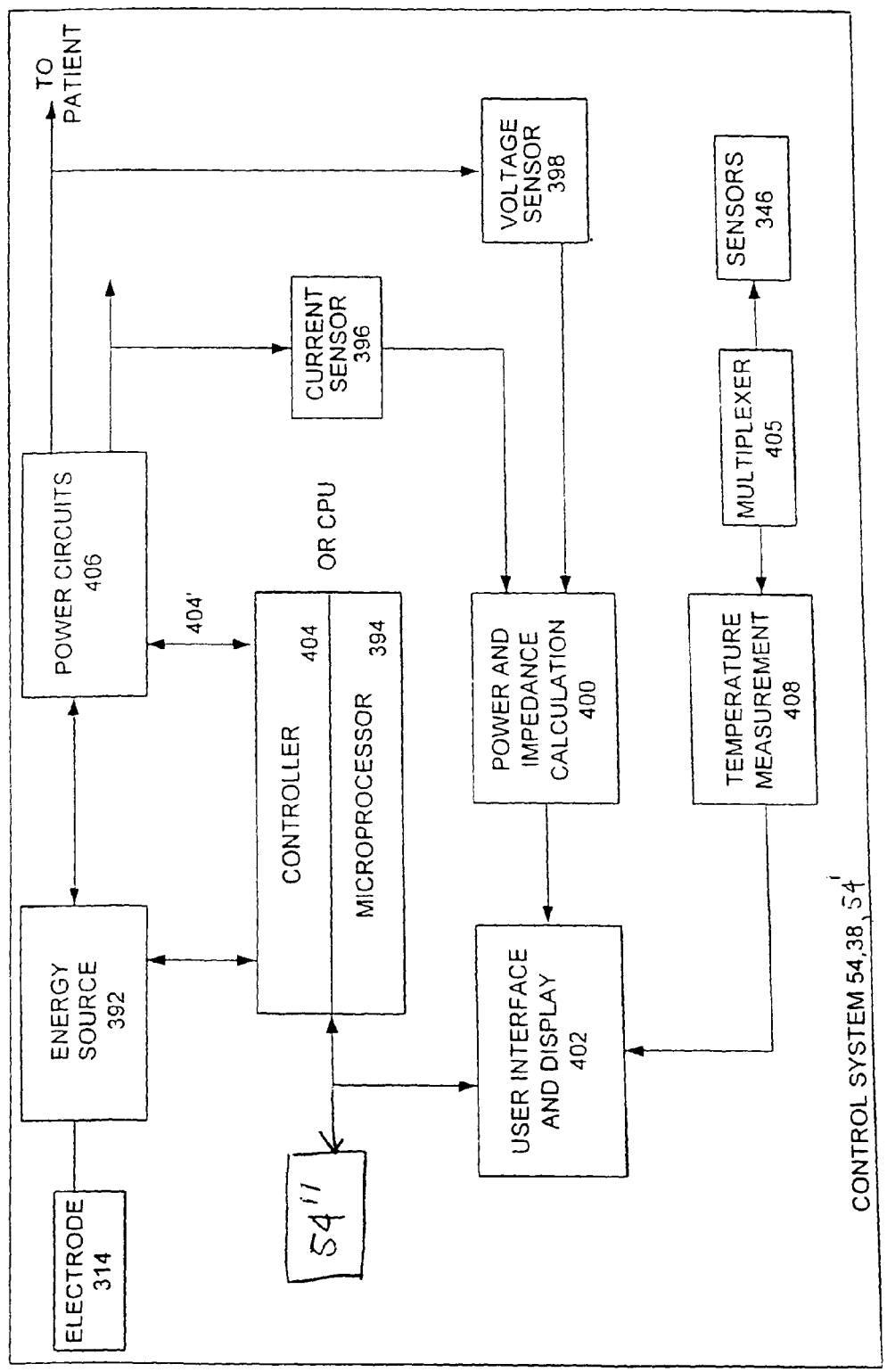
FIG. 23 depicts a block diagram of the feed back control system that can be used with the pelvic treatment apparatus.

Referring now to FIGS. 1, 22 and 23, in various embodiments, elements of apparatus 8 can be coupled to an open or closed loop feedback control system 54 (also called control system 54, control resources 54 and resources 54). Control system 54 can be configured used to control the delivery of electromagnetic and mechanical energy to the skin surface and underlying soft tissue structure to minimize, and even eliminate, thermal damage to the skin and underlying tissue cell necrosis as well as blistering of the skin surface. Control system 54 can be configured to be used with one or more embodiments of patient feedback described herein, including verbal and biometric feedback. Also control system 54 can be configured to be used with one or more embodiments of patient feedback methods described herein including verbal and biometric feedback and combinations thereof.

Control system 54 can be configured to monitor other parameters including but not limited to, the presence of an open circuit, short circuit or if voltage and current are supplied to the tissue for more than a predetermined maximum amount of time. Such conditions may indicate a problem with various components of apparatus 8 including RF generator 22, and monitoring unit 38' or 39'. Control system 54 can also be configured to control the delivery of energy to selected tissue including epidermal, dermal, and subdermal over a range of skin thermal conductivities including, but not limited to, the range of about 0.2 to about 1.2 W/(m$^2$ C). In various embodiments, control system 54 can include a digital computer or microprocessors such as an application specific integrated circuit (ASIC) or a commercial microprocessor (such as the Intel.® Pentium® series) with embedded monitoring and control software and input/output ports for electrical connections to sensors 23 and other measurement circuitry. In a related embodiment, control system 54 can comprise an energy control signal generator that generates an energy control signal.

In an alternative embodiment control system 54 can be integral to a separate device or instrument 54' that is coupled to one or more of fluid delivery devices 13, energy delivery devices 18, power source 22, sensors 23 or a patient feedback input device 54". Device 54' can comprise a microcomputer, processor or PDA device known in the art. Patient feedback input device 54" can be configured to allow the patient or physician to input patient feedback in a variety of forms including, but not limited to, a patient pain/thermal sensitivity scale describe herein which can be manually or verbally entered. Other feedback can include one or more biometric parameters described herein. In an embodiment patient feedback input device 54" can comprise a handheld computer, PDA device, keyboard, touch screen, mouse, control knob, electronic sip-straw, joystick, microphone, speech recognition device, CCD, electronic camera or other input/output device known in the art.

Referring now to FIG. 23, an open or closed loop feedback control system 54 couples sensor 346 to energy source 392 (also called power source 392). In this embodiment, electrode 314 is one or more RF electrodes 314; however, other energy delivery devices described herein are equally suitable. The temperature of the tissue, or of RF electrode 314, is monitored, and the output power of energy source 392 adjusted accordingly. The physician can, if desired, override the closed or open loop control system 54. A microprocessor 394 can be included and incorporated in the closed or open loop system to switch power on and off, as well as modulate the power. Closed loop feedback control system 54 utilizes microprocessor 394 to serve as a controller, monitor the temperature, adjust the RF power, analyze the result, refeed the result, and then modulate the power.

With the use of sensor 346 and feedback control system 54, tissue adjacent to RF electrode 314 can be maintained at a desired temperature for a selected period of time without causing a shut down of the power circuit to electrode 314 due to the development of excessive electrical impedance at electrode 314 or adjacent tissue as is discussed herein. Each RF electrode 314 can connected to logic resources that generate an independent output. The output maintains a selected energy at RF electrode 314 for a selected length of time.

Current delivered through RF electrode 314 is measured by current sensor 396. Voltage is measured by voltage sensor 398. Impedance and power are then calculated at power and impedance calculation device 400. These values can then be displayed at user interface and display 402. Signals representative of power and impedance values are received by a controller 404. A control signal 404' (also called energy control signal 404') is generated by controller 404 that is proportional to the difference between an actual measured value, and a desired value. The control signal is used by power circuits 406 to adjust the power output an appropriate amount in order to maintain the desired power delivered at respective RF electrodes 314.

In a similar manner, temperatures detected at sensor 346 provide feedback for maintaining a selected power. Temperature at sensor 346 is used as a safety means to interrupt the delivery of power when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output an appropriate amount in order to maintain the desired temperature delivered at the sensor 346. A multiplexer can be included to measure current, voltage and temperature, at the sensor 346, and energy can be delivered to RF electrode 314 in monopolar or bipolar fashion.

Controller 404 can be a digital or analog controller, or a computer with software. When controller 404 is a computer it can include a CPU coupled through a system bus. This system can include a keyboard, a disk drive or other non-volatile memory device or computer readable storage medium, a display, and other peripherals, as are known in the art. A program memory and a data memory are also coupled to the bus. User interface and display 402 includes operator controls and a display. Controller 404 can be coupled to imaging systems including, but not limited to, ultrasound, CT scanners, X-ray, MRI, mammographic X-ray and the like. Further, direct visualization and tactile imaging can be utilized.

The output of current sensor 396 and voltage sensor 398 are used by controller 404 to maintain a selected power level at each RF electrode 314 and also to monitor stray currents 427'

(dues to insulation failure or capacitive coupling) flowing from electrode 314. The amount of RF energy delivered controls the amount of power. A profile of the power delivered to electrode 314 can be incorporated in controller 404 and a preset amount of energy to be delivered may also be profiled. Also, should stray current 427' rise to an undesired level, controller 404 shuts down power source 392.

Circuitry, software and feedback to controller 404 result in process control, the maintenance of the selected power setting which is independent of changes in voltage or current, and is used to change the following process variables: (i) the selected power setting, (ii) the duty cycle (e.g., on-off time), (iii) bipolar or monopolar energy delivery; and, (iv) fluid delivery, including flow rate and pressure. These process variables are controlled and varied, while maintaining the desired delivery of power independent of changes in voltage or current, based on temperatures monitored at sensor 346.

Figure 24:
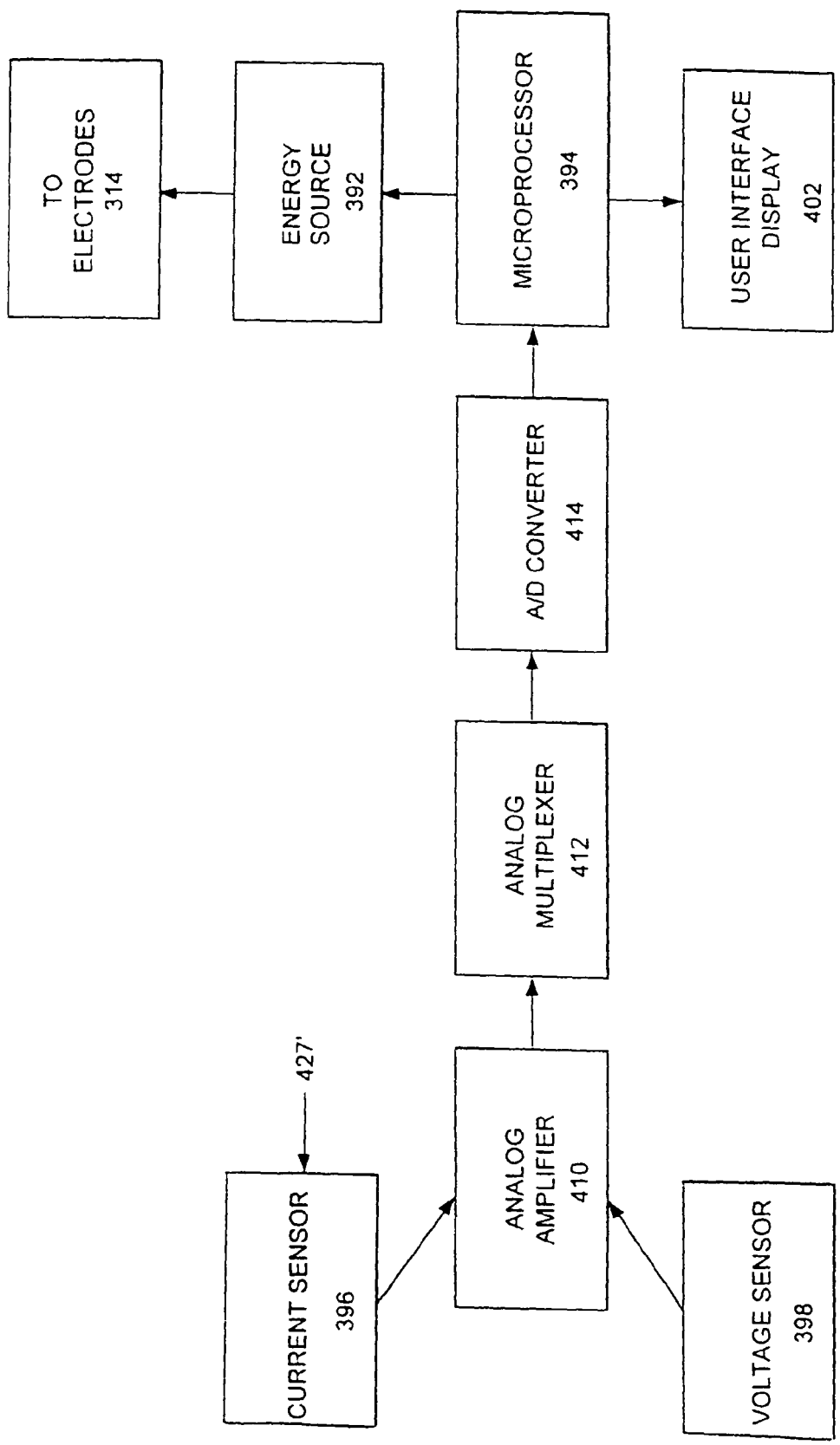
FIG. 24 depicts a block diagram of an analog amplifier, analog multiplexer and microprocessor used with the feedback control system of FIG. 23.

Referring now to FIG. 24, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage, which represents the respective sensed temperatures. Digitized amplifier output voltages are supplied by A/D converter 414 to microprocessor 394. Microprocessor 394 may be a MPC601 (PowerPC®) available from Motorola or a Pentium® series microprocessor available from Intel®. In specific embodiments microprocessor 394 has a clock speed of 100 Mhz or faster and includes an on-board math-coprocessor. However, it will be appreciated that any suitable microprocessor or general purpose digital or analog computer can be used to calculate impedance or temperature.

Microprocessor 394 sequentially receives and stores digital representations of impedance and temperature. Each digital value received by microprocessor 394 corresponds to different temperatures and impedances. Calculated power and impedance values can be indicated on user interface and display 402. Alternatively, or in addition to the numerical indication of power or impedance, calculated impedance and power values can be compared by microprocessor 394 to power and impedance limits. When the values exceed or fall below predetermined power or impedance values, a warning can be given on user interface and display 402, and additionally, the delivery of RF energy can be reduced, modified or interrupted. A control signal from microprocessor 394 can modify the power level supplied by energy source 392.

Figure 25:
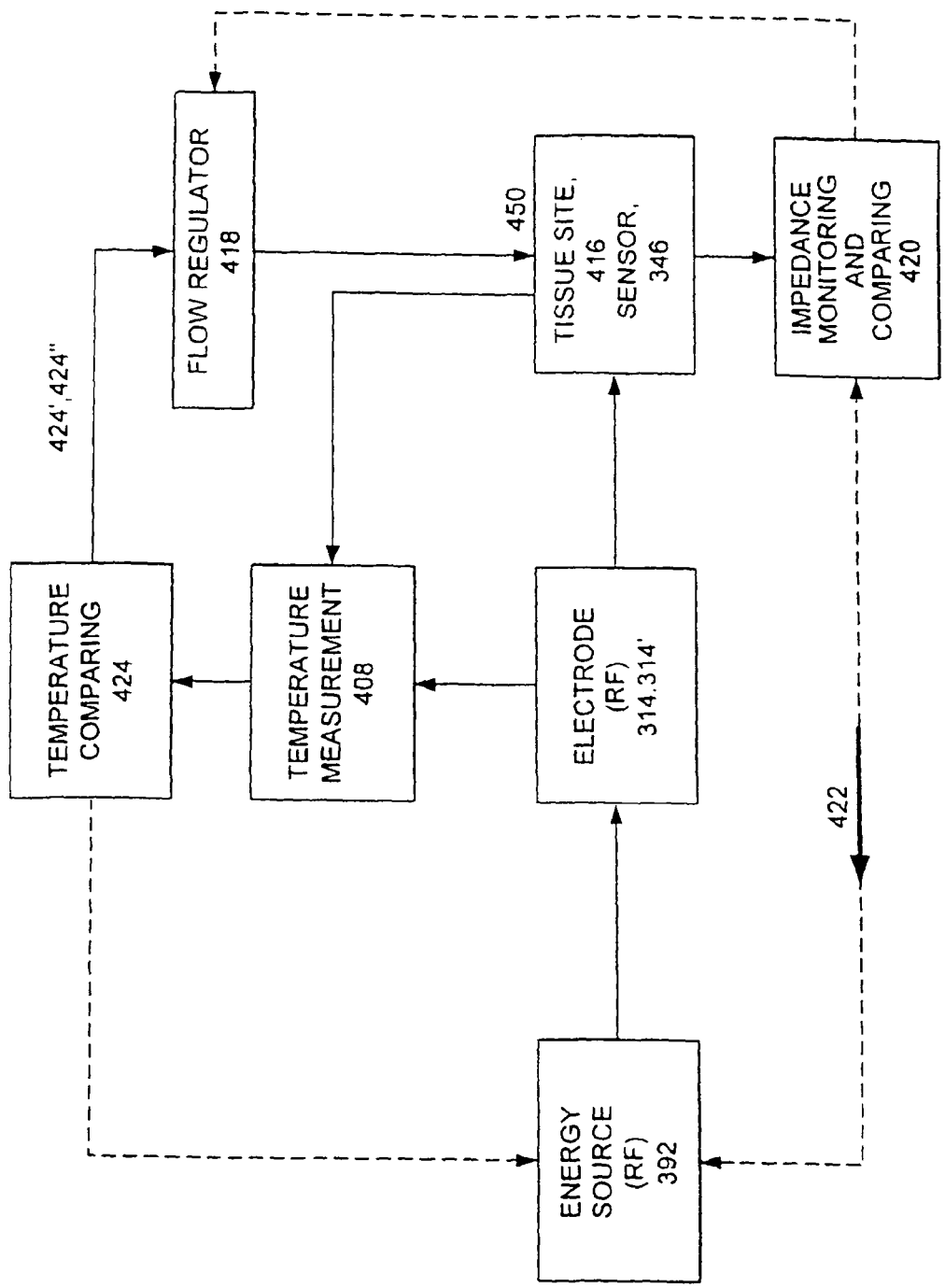
FIG. 25 depicts a block diagram of the operations performed in the feedback control system depicted in FIG. 23.

FIG. 25 illustrates a block diagram of a temperature and impedance feedback system that can be used to control the delivery of energy to tissue site 416 by energy source 392 and the delivery of cooling medium 450 to electrode 314 and/or tissue site 416 by flow regulator 418. Energy is delivered to RF electrode 314 by energy source 392, and applied to tissue site 416. A monitor 420 (also called impedance monitoring device 420) ascertains tissue impedance (at electrode 314, tissue site 416 or a passive electrode 314'), based on the energy delivered to tissue, and compares the measured impedance value to a set value. If measured impedance is within acceptable limits, energy continues to be applied to the tissue. However if the measured impedance exceeds the set value, a disabling signal 422 is transmitted to energy source 392, ceasing further delivery of energy to RF electrode 314. The use of impedance monitoring with control system 54 provides a controlled delivery of energy to tissue site 416 (also called mucosal layer 416) and underlying cervical soft tissue structure which reduces, and even eliminates, cell necrosis and other thermal damage to mucosal layer 416.

Impedance monitoring device 420 is also used to monitor other conditions and parameters including, but not limited to, presence of an open circuit, short circuit; or if the current/energy delivery to the tissue has exceeded a predetermined time threshold. Such conditions may indicate a problem with apparatus 24. Open circuits are detected when impedance falls below a set value, while short circuits and exceeded power delivery times are detected when impedance exceeds a set value In an embodiment, the control of cooling medium 450 to electrode 314 and/or tissue site 416 is done in the following manner. During the application of energy, temperature measurement device 408 measures the temperature of tissue site 416 and/or RF electrode 314. A comparator 424 receives a signal representative of the measured temperature and compares this value to a pre-set signal representative of the desired temperature. If the measured temperature has not exceeded the desired temperature, comparator 424 sends a signal 424' to flow regulator 418 to maintain the cooling solution flow rate at its existing level. However if the tissue temperature is too high, comparator 424 sends a signal 424" to a flow regulator 418 (connected to an electronically controlled micropump, not shown) representing a need for an increased cooling medium 450 flow rate.

In various embodiments, feedback can be incorporated into a tissue treatment procedure or skin tightening procedure in a variety of different manners. These varied approaches can be adapted for use with exemplary apparatus 8 or other energy delivery apparatus known in the art. Referring to FIG. 26 in various embodiments, patient feedback can be used to control the delivery of energy or cooling, or both to a target tissue site 9 by communicating signaling or otherwise coupling patient feedback or feedback signals 54s to one or more of the energy delivery device 18, energy source 22, cooling device 13, a feedback control system 54 or a manual control device 54" actuated by the physician or the patient or both. The feedback control system 54 can be coupled to one or both of the energy source 22, fluid delivery or cooling device 13.

Referring now to FIG. 27, in related embodiments correlations can be established between measured physiological or biometric signals 54bs indicative of thermal/pain sensations (e.g. vasodilation, skin conductivity, temperature etc) and a patient determined scale 54ps of thermal/pain sensation such as the three level scale described herein. The use of such a correlation allows control system 54 to provide a faster or more sensitive indicator of pain or thermal injury than could be communicated by the patient. The correlation can be done before the procedure and can be repeated over the course of a procedure as needed to account for variations in tissue properties and changes in patient perceptions. In alternative embodiments, the correlation can be continuously updated over the course of the treatment as the patient provides ongoing verbal indications of their level of pain/thermal sensation. Also the correlation procedure can be repeated for different tissue sites as needed. In various embodiments, the correlation(s) can be computed and stored in control system device 54', feedback entry device 54" and/or a database 60db using biomedical data acquisition, signal analysis or feedback algorithms known in the art. Device 54' or 54" can be configured to allow the physician to select between use of biometric or patient verbal feedback or a combination of both. In use, this approach can allow for a more sensitive and accurate indication of patient pain/thermal sensation during a procedure and in turn provide more precise or fine tuned control of energy delivery to achieve a selectable tissue effect.

In various embodiments, biometric feedback can include a plurality of signals 54s. In an embodiment shown in FIG. 28, this plurality can include a first 54s1 and a second signal 54s2, wherein the combination of the first and the second signal is used to determine or provide an indication of a patient perceived sensation of tissue heating or pain. In an embodiment the signals can be the same parameter 54p but from different locations on the body, for example, the target tissue site 9 and a non-target tissue site 9n, which can be a contralateral site (e.g. the opposite cheek face) to target site 9. In use, these and related embodiments can provide increased sensitivities to changes in tissue properties indicative of thermal effect or injury by utilizing real-time comparisons between a control and target tissue site. Also sites indicative of various physiological responses of pain or heat (such as vasodialation, vasoconstriction, sweating, etc) can also be chosen. Examples of such sites include without limitation, the hand, fingers, fingertips, forehead, mouth, lips and the like.

In an alternative embodiment, the feedback signals can be different biometric parameters 54p', for example temperature and skin conductivity/impedance, or temperature and skin absorbance/reflectance. In use multiple biometric parameters can provide for increased sensitivity to one or more physiologic responses indicative of pain, heat or thermal damage.

Referring back to FIG. 26, in an embodiment the feedback control system can include a software feedback control module 54m electronically stored in device 54' or 54" or other logic resources 54lr known in the art. The feedback module 54m can include stored software programs or electronic instructions sets 54m' as well as database 60db configured for performing one or more of the following functions: (i) controlling or facilitating the pain or thermal sensation calibration procedures described herein; (ii) controlling the delivery of energy (including power levels, power profiles (e.g. ramps and curves), duty cycles); (iii) controlling the delivery of cooling media; (iv) receiving biometric data from the patient and controlling energy delivery or cooling media delivery responsive to that input; (v) receiving patient verbal feedback (using speech recognition software known in the art and controlling the delivery of energy or cooling responsive to that verbal feedback; (vi) providing the physician with auditory or visual prompts in performing the procedure; (vii) convert or modify the pain or thermal sensation calibration scale for different tissue sites and procedures; (viii) monitor various patient data and provide the physician alarms for various patient conditions (e.g. heart rate, degree of tissue damage, etc.); (ix) capture images of the tissue site such as video, ultrasound, thermo-graphic and infrared images before during or after the procedure; (x) display images of the tissue site before, during and/or after a treatment; and (xi) display a template overlay, visual cues or pointers superimposed on an a tissue site image to assist the physician with the procedure.

The manual control device 54" can be configured to allow either the medical practioner or patient to control the delivery of energy, heat or cooling to the tissue site. Such control of energy can include attenuation, complete cessation, cessation for a fixed period or increased delivery for selectable periods. Other embodiments can be configured to allow for simultaneous or near simultaneous control of both the delivery of energy and cooling. For example, energy delivery can be decreased while cooling delivery is increased.

In use, patient feedback can allow the physician to use a single and simple indicator to regulate or titrate the delivery of energy to a selected tissue site to achieve a selectable tissue effect such as skin tightening, remodeling or rejuvenation. Specifically, by quantifying patient sensation, the delivery of net energy to the target tissue can be linked to the variation of a single modality where the energy output of the device is titrated to the patient's perception of heat or pain. Even though pain tolerances can vary from patient to patient, the perceived heat or pain by the patient can have a consistent relationship to the net energy delivered by the source of energy. In alternative embodiments, erythema (or another skin optical or thermal property indicative to tissue injury) can be used as an indicator for titrating energy delivery and/or cooling. For example, a particular site can be retreated if it does not exhibit erythema, or energy delivery reduced or ceased once erythema begins to appear. The level of erythema can be determined visually, or via an imaging device or thermo-graphic imaging device such as in infrared camera or a spectrophotometric measurement device known in the art. In various embodiments, use of one or more of these imaging devices can be coupled to logic resources such as 54lr that include a module (e.g., module 54m) or algorithm for determination of erythema based on comparison of real-time measurements to baseline measurement for a given patient or a eryrthema measurement database for skin types, skin location or combination of both or other physiological parameters (e.g. age, sex, etc).

Referring now to FIG. 29a, embodiments of a treatment algorithm using feedback control can include a patient determined/calibrated numeric pain/thermal scale 54ps for particular levels of energy delivery or levels of energy delivery combined with the delivery of a cooling medium. Numeric values can be assigned by the patients for levels of pain corresponding to particular amounts (e.g. joules) 54ae or rates (e.g. watts) 54re of energy delivery or amounts of energy delivery combined with a rate of delivery of a cooling medium 54cr (e.g. cc fluid/sec) having a selected temperature. Numeric values can be determined for sub-threshold pain tolerance levels, threshold pain tolerance levels, and over threshold pain tolerance levels. In an embodiment, a sub-threshold pain/thermal level can be assigned a value of one, a threshold pain/thermal level can be assigned a value of two and over-threshold level a value of three. An alternative embodiment can use a ten point scale (1, 5 and 10 for sub, at and post threshold levels, and/or any value in between) or any numeric range selected by the patient. In other alternative embodiments, the patient can select a color scale (for example white, green, red) to represent the levels of pain. In still other alternative embodiment the patient can select descriptive words (e.g. nothing, tingling, hurting, burning, excruciating, etc) to represent or indicate one or more levels of pain/thermal sensation. The patient can choose whichever means they find easiest to communicate their sensation of pain. The physician can have the patient try several methods (e.g. numeric, color, descriptive, etc) and then choose the method that has the greatest reproducibility for a given patient. Also in any of these embodiments, speech recognition and/or voice stress analysis software can be used to provide supplement information and analysis regarding the patient indicated level of pain. In such embodiments one or more components from such supplemental information can be coupled to the patients verbal description to enable a more reproducible indication of the patient's pain level.

In various embodiments, the pain and/or thermal calibration procedure can be done prior to initiation of the tissue treatment procedure and can be repeated at any time during the procedure to account for variations or treatment variables including without limitation, procedural, tissue site and patient variations. Also the calibration procedure can be performed utilizing energy delivery at a selectable tissue site 9 and can be repeated when a new site is selected to account for any site variation. Alternatively, the calibration procedure can be on a site that is physiological representative of the target tissue site and has equivalent pain sensitivity or at a selected site that has a greater or lesser pain sensitivity. Sights having greater sensitivity could include the fingertips, while reduced sensitivity sites could include skin on the back of the arms or the back itself.

In a various embodiments, a database 60*db* or mathematical model 60*m* can be utilized to calibrate or adjust the scale for pain/thermal sensitivities of different tissue sites or other treatment parameters. The mathematical model 60*m* or database 60*db* can be stored within device 54' or 54" or other logic resources 54*lr*, memory resources 54*mr* or computer readable storage medium 54*sm*. Examples of computer readable storage mediums include without limitation, floppy disks, magnetic tape, hard drives, ZIP drives, CD ROMs, ROMs, PROMs, EPROMs, ASICs and the like and other storage medium known in the art.

In various embodiments the model or database can be developed from a patient population database, a parametric database or data collected from each patient from a single treatment or multiple treatments or combinations thereof. The data can be collected during one or more calibration procedures described herein, over the course of an actual treatment or a combination of both. The model 60*m* can employ various numerical methods known in the art including linear interpolation, least squares, curve fitting, cubic spline and Newton Raphson fitting methods and the like and combinations thereof. As described below, database 60*db* can accessed or manipulated using database applications or programming language known in the art such as those available from the Oracle® Corporation (Redwood Shores, Calif.).

Referring now to FIGS. 29*a*-29*c* In various embodiments database 60*db* can be a relational database, an object oriented database, a programmable database, a network database, an Internet database, an analytical database, a hierarchal database, a meta-database or other database known in the art. Database 60*db* can also be configured to be coupled to other databases 60*db'* including databases store on or coupled to the Internet or other distributed network 60*dn*.

In an embodiment, database 60*db* can be a relational database configured to be programmed, queried, or updated using structured query language (SQL) known in the art. Accordingly in these and related embodiments, database 60*db* can include or otherwise be coupled to a database program module 60*dbm* which contains programs, or database applications known in art for performing one or more queries or other database operations known in the art. Module 60*dbm* be contained within the database or can be stored or embedded in logic resources 54*lr*, memory resources 54*mr*, device 54' or device 54".

In various embodiments database module 60*dbm* can also be configured to allow the user to enter, delete, or order, pool or otherwise manipulate data in the database. For example, the module can be configured to allow the user to select and utilize data for a single patient over a single treatment, data for a single patient over multiple treatments, data for multiple patients or data for an entire patient population. In this way, the user can adjust or fine tune the database for a given patient or procedure to obtain a more accurate and/or precise control of an energy delivery parameter or treatment controlled by the database. This fine tuning process can also be during the treatment process to dynamically modify the database during treatment. The database module can also be configured to allow the user to establish or change associations between one or more data elements, attributes or fields in the database such as pain/thermal sensation, delivered energy, an anesthesia dose, etc. Thus, the user can choose which particular treatment parameters to associate with a corresponding pain/thermal sensation level. In this way, the user can also fine tune or adjust the database to a particular treatment or patient to obtain more accurate and/or precise control of an energy delivery parameter or treatment.

In various embodiments database 60*db* can have different storage organizations or data structures known in the database arts. In an embodiment shown in FIG. 29*b*, database 60*db* can have one or more records 60*dbr* which can include one or more data fields 60*dbf* which can include a first field 60*dbf'* and a second field 60*dbf'* used to store one or more data elements 60*de*. First field 60*dbf* can be used to store a treatment parameter 60*tp* and second field 60*dbf'* used to store a pain or thermal sensation level 60*ptl* correlated or otherwise associated with the treatment parameters 60*tp*. In an embodiment, the database can configured to have multiple treatment parameter fields 60*dbf* associated with a single pain/thermal sensation level field 60*dbf'* to allow for multi-variant or otherwise complex associations between treatment parameters and associated pain/thermal sensation or sensitivity.

In an embodiment shown in FIG. 29*c*, database 60*db* can be a relational database known in the art having a table data structure where data elements 60*de* are stored in tables 60*t* having rows 60*r* and columns 60*c* which correspond to records 60*dbr* and fields 60*dbf* Table 60*t* can include multiple columns for storing pain or thermal sensation levels and one or more associated treatment parameters. In a related embodiment, database 60*db* can be an object oriented database having object tables 60*ot* consisting of objects 60*o* and attributes 60*a* which correspond to records 60*dbr* and fields 60*dbf*. Attributes 60*a* can be used to store pain/thermal sensation levels and associated treatment parameters. In these embodiments database module 60*dbm* can be configured to support various relational and object oriented database methodologies known in the art.

In an embodiment, a calibration procedure can be done to generate a database or model that correlates a pain or thermal sensation level to a particular energy delivery treatment parameter such as a power level (e.g. an RF power level) or a total delivered energy to a tissue site. In use, such a database can be configured to allow the medical practioner to utilize the patient's perceived pain or thermal sensation during an energy delivery treatment to more rapidly and precisely control the delivery of energy to a selected tissue site then would be possible without such feedback. Once the pain or thermal sensation level exceeds a certain threshold, system 54 or device 54' can be configured to stop or decrease the delivery of energy to the tissue (or start increase the delivery of a cooling media) to preserve or otherwise protect non target tissue sites (e.g. an epidermal layer, sub-dermal plexuses) from unwanted thermal injury or damage. Other suitable energy delivery parameters that can be correlated with pain or thermal sensation levels can include without limitation, frequency of the energy source (e.g. RF, microwave, acoustical, etc.), wavelength of the energy source (e.g. optical wavelength), power waveform, duty cycle, current, heat transfer media flow rate, cooling media flow rate, fluid flow rate and the like. In an embodiment calibration procedures can be done to develop a database that correlates multiple energy delivery parameters to a pain or thermal sensation level or sensitivity.

In other embodiments, a calibration procedure can be performed to account for variations in pain/thermal sensation or sensitivity due to use of an anesthetic or other related medicaments. Again a database or mathematical model (using numerical methods described herein) can then be developed to calibrate or adjust a pain or thermal sensation scale for one or more anesthetic variables including without limitation, total dose, rates of delivery, delivery sites (e.g., topical, local, etc), delivery methods (e.g., bolus vs. continuous infusion), anesthetic types and combinations thereof. The model or database can also be configured to transform or convert a perceived pain or thermal sensation level for one dose of anesthetic, to that which would be experienced for another dose or when no anesthetic is used at all. The model could also employ the numerical methods described herein and/or pharmacokinetic models to account for one or more pharmacokinetic variations associated with the use of an anesthetic. For example, the model could be configured to account for variations in pain sensitivity due to changing levels of anesthetic at the tissue site or in the patient's body over the course of the treatment.

Embodiments of the invention can include one or more treatment algorithms that incorporate patient feedback into the treatment procedure. Example treatment algorithms are shown in FIGS. 30 and 31. The sequence of steps in these embodiments is exemplary and need not be sequence specific. Accordingly the order of steps can be varied, and one or more steps can deleted or repeated as needed by the physician. For example, microdermabrasion can be performed after administration of the anesthetic or the sedation step need not be done and the thermal/pain sensation scale developed without it. Other steps can also be added, for example re-treatment of a given site can be done based on other criteria such as degree of erythema, skin tension, or other physical characteristic or appearance.

Also while these algorithms use an RF energy delivery device and power sources, these approaches are exemplary and other energy delivery means and power sources are equally applicable to the algorithm including but not limited to the use of dermatological lasers, microwave, ultrasound, infrared lamps, heat transfer fluids and combinations thereof all well known in the plastic surgery and medical instrument arts. Further, such energy can be applied topically, cutaneously or sub-cutaneously using surgical or minimally invasive surgical methods known in the art.

For laser embodiments, patient feedback can be utilized to achieve skin rejuvenation while preserving, at least in part, the epidermal layer and/or prevent burning, photocoagulation, or other injury to the epidermal layer or other non-target tissue. In a specific embodiment, an RF energy delivery device can be combined with the use of topical laser treatment either concurrently or in a pulsed duty cycle fashion. Suitable lasers can include, but are not limited to, any medical laser known in the arts including CO2 lasers, YAG lasers, dermatological lasers, flash lamp, pumped pulsed dye laser (585 nm), argon-pumped tunable dye laser (577 nm, 585 nm), copper vapor or copper bromide laser (578 nm).

In various embodiments, patient feedback can be utilized for performing a number of treatments of the skin and underlying tissue including, without limitation, epidermal remodeling and tightening, wrinkle reduction, elastosis reduction, sebaceous gland removal/deactivation, hair follicle removal, adipose tissue remodeling/removal and spider vein removal and combinations thereof. The form and amount of patient feedback can be adapted for each of these particular applications. For example, the patient pain scale for sebaceous gland removal on the face can be set at lower level than for spider vein removal on an extremity. This can be done empirically or using a mathematical model 60$m$ or database 60$db$ described herein, to correlate feedback from one type of procedure to any number of procedures.

The use of one or more embodiments of patient feedback methods described herein can be adapted to be used with the tissue treatment procedures described herein as well as other dermatological and reconstructive or plastic surgical procedures known in the art. In various embodiments, feedback methods can be adapted for different procedures using site correlation or mathematical model approaches described herein as well as use of a patient population database or an individual patient database generated during the course of one or more procedures.

In various embodiments, treatment levels can be titrated by using heat or pain perception signaling by the patient. Further, the patient's perception of pain or heat or physiological or biometric indicators thereof can be utilized to reduce or stop treatment or energy delivery so as to maintain temperature of non target tissue below an injury threshold level. In various embodiments, such injury threshold temperature can be 45° C. or lower, 42.5° C. or lower, 40° C. or lower or 37° C. or lower, or 35° C. This can be done by verbal communication to the medical practioner (via one or more of the pain/thermal scales described herein) or alternatively via biometric feedback coupled to the energy source or a feedback control system described herein (which may be coupled to the power source) or a combination of both verbal signaling and biometric feedback.

Several other examples of treatment algorithms and/or methods of using patient feedback are included herein (see Examples I-III), including treatment of eyebrows, jowls and forehead. In these and related embodiments, treatment levels can be titrated by using heat or pain perception signaling by the patient or by use of biometric measurement indications thereof. Areas having sub-threshold pain levels can receive additional treatment energy which can be in the form of additional passes by a skin energy delivery device. Contrarily, treatment can be stopped to areas producing a threshold pain/heat level. Also different perception levels can be used to titrate treatment for areas having differences in skin thickness and/or greater or lesser sensitivity to heat or pain.

Referring now to FIGS. 32, 33$a$ and 33$b$, in various embodiments, photographic or visual documentation of the tissue treatment site and surrounding areas can be utilized in one or more embodiments of the invention for treating tissue. Various methods of photographic or visual documentation can be configured to perform one or more of the following: (i) identify the target tissue site; (ii) quantitatively assess tissue treatment; (iii) qualitatively assess tissue treatment (iv) determine a treatment endpoint; (v) document a treatment endpoint; (vi) determine an amount of skin tightening; (vii) determine an amount of tissue remodeling; (viii) determine the need for repeat treatment; (ix) establish a patient population database for treatment at one or more tissue sites; (x), establish an image database of treatments at one or more tissue site; (xi) document a clinical or aesthetic result of a procedure; (xii) perform computer assisted modeling of a desired tissue shape or aesthetic result; and (xiii) perform computer assisted modeling of the tissue treatment procedure (e.g. direction of energy delivery application or number of passes of the energy delivery device of the tissue site) to achieve a desire result. An embodiment of an algorithm for performing photographic documentation is shown in FIG. 32. Again, the sequence of steps is exemplary and is not sequence specific. One or more steps may done in a different sequence or repeated as needed by the physician, nurse or other medical practitioner.

FIGS. 33$a$-33$b$ show an embodiment of a method for image alignment for pre and post treatment images 80, 82 of target tissue site 9. The pretreatment photo 80 can be pasted as a partial transparency over the post treatment photo 82. This can be also done manually using a back illumination device (e.g., a tracing light or table) or electronically using an electronic photographic editor (an example being Photoshop®), to superimpose the post treatment image over the pretreatment image or vice versa. Anatomic landmarks 84 between the pre-treatment and the post-treatment photos/images 80, 82 can be aligned (with the exception of those of the treatment site). The treatment site 9 can then be visually assessed by the physician for degree of completion, skin tightening, remodeling, shape and the like. The assessment can also be done using optical projection or magnification devices as well as image analysis software known in the art to compare the two images to provide both quantitative (e.g. dimensional changes) and qualitative indications of the effects of a given treatment. In these and related embodiments the images can be displayed on a display device 402, which can be integral to device 54' or 54".

Referring now to FIG. 34, an alternative embodiment of a method of to treat tissue to correct an aesthetic deformity 9d or redundancy 9r can include the use of a grid pattern 86 and a method for evaluating the predominant axis 9a of the deformity or skin redundancy. The predominate axis of the deformity can be determined and utilized to orient the grid pattern to most effectively correct the aesthetic deformity. The predominant axis can be determined visually, through dimensional measurement, or through computer determination using video imaging and spatial analysis software.

In an embodiment shown in FIG. 34, an oblong grid pattern 86o can be aligned along the principle axis 9a of the redundancy 9r or deformity 9d. The grid pattern can consist of 1 cm$^2$ grid sites or other sizes larger or smaller depending on the tissue site. Specifically, the longitudinal axis of the grid pattern 86la can drawn on the skin treatment site 9 and the longitudinal axis of the grid pattern 86la is aligned with the principal axis 9a of the skin redundancy. An exemplary range of grids size include the range from about 0.1 to about 10 cm$^2$, with other sizes and units (e.g. inches) also being equally applicable.

The alignment of the drawn grid pattern may be vertical for vertical skin redundancies, for example redundancy of the submental neck or oblique for a skin redundancy of the nasolabial fold. In the case of a vertical skin redundancy, more grid rows are drawn than grid columns. For a horizontally aligned skin redundancy such as the cheek, more columns are drawn at the treatment site than rows. For an equal skin redundancy in the vertical and horizontal dimensions, a square pattern grid with the same number of rows and columns can be drawn. Depending on the type of the aesthetic deformity and the perspective of the observer, the medical practitioner may reverse the pattern of grid orientation such that fewer rows or columns are drawn along the principle axis of skin redundancy.

Figure 35:
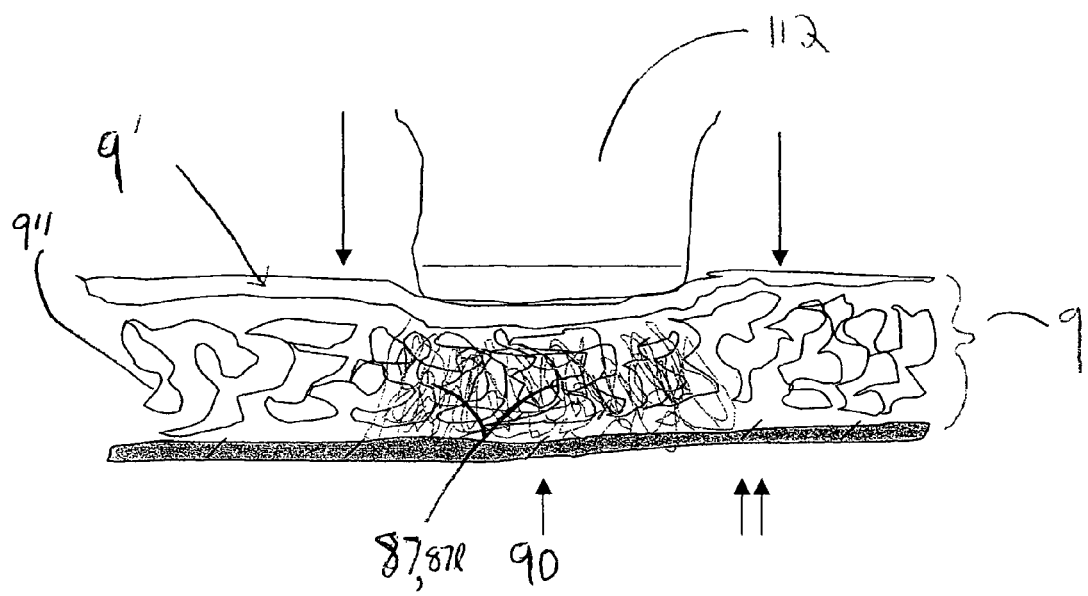
FIG. 35 is a lateral view illustrating an embodiment utilizing the application of energy without the application of vectored force.
Figure 36:
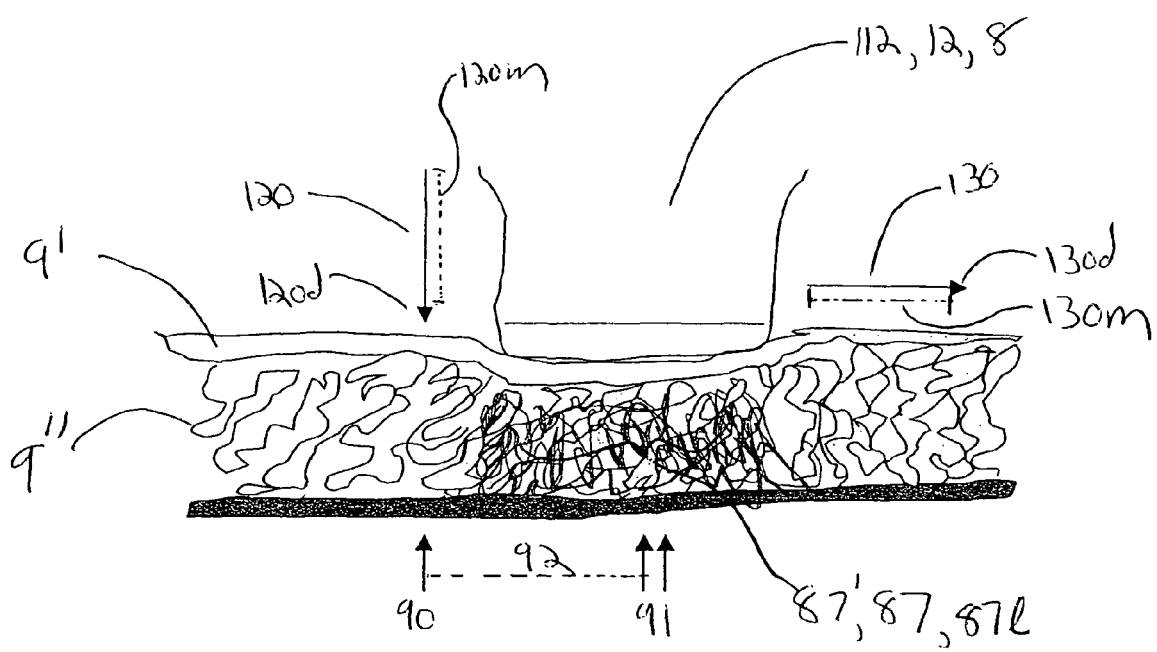
FIG. 36 is a lateral view illustrating an embodiment utilizing the application of energy and vectored force to produce thermal adhesions to produce a desired tissue configuration or aesthetic effect.
Figure 37:
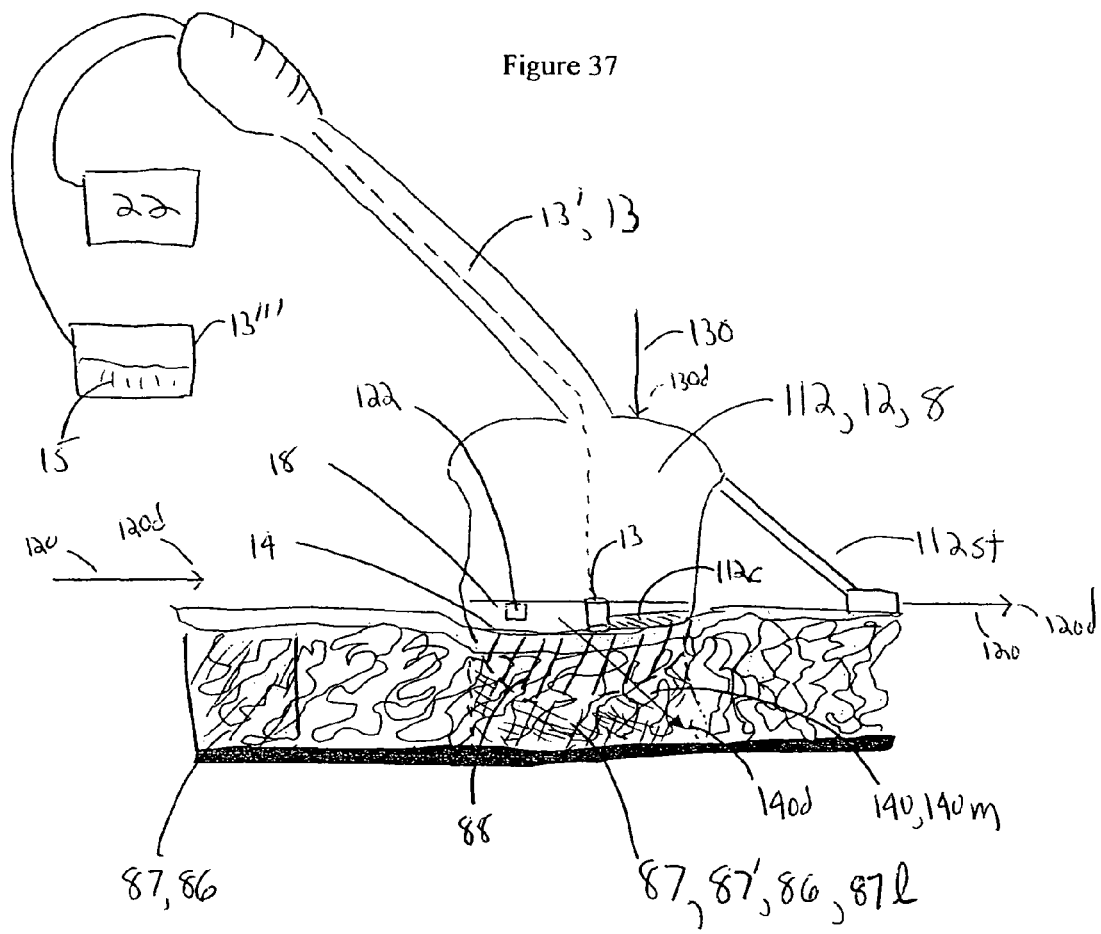
FIG. 37 is a lateral view illustrating an embodiment of an apparatus for delivery energy and vectored force, the embodiment including a skin tensioning device or a surface coating or texture to facilitate force application and/or skin repositioning.
Figure 36:
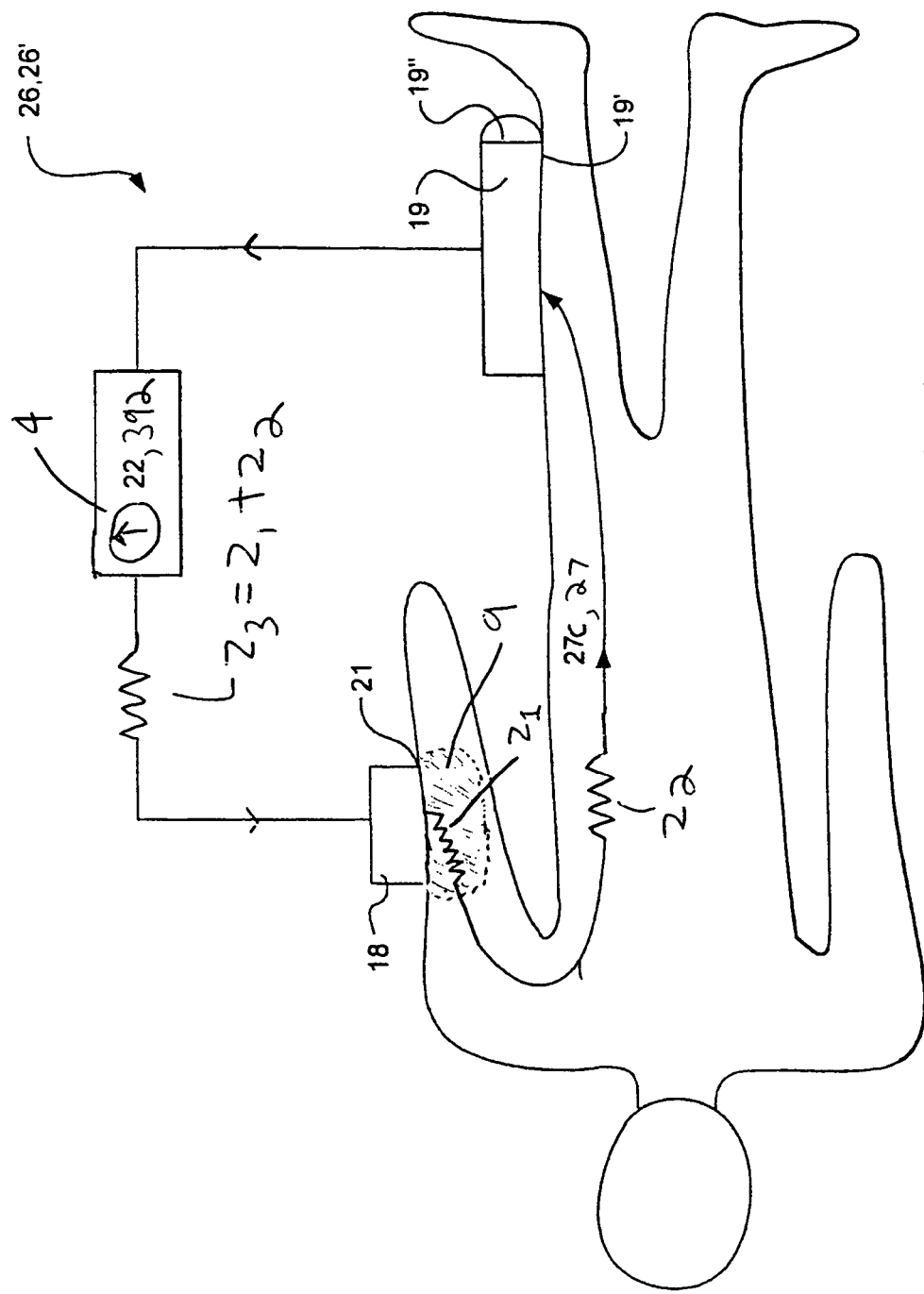

Referring now to FIGS. 35-37, other embodiments of methods and apparatus of the invention can include the use of both energy delivery and a vectored application of force to the tissue site to produce a desired tissue configuration, aesthetic effect or amount of tissue remodeling. The vectored application of force in a selected direction can be used to reposition (e.g. pull) the tissue into a selected location to produce the desired aesthetic effect, etc. Energy is then applied to secure the tissue in the new location via thermal adhesion as well as creating localized skin tightening and rejuvenation via immediate collagen contraction as well subsequent collagen deposition through a wound healing response described herein. This procedure is referred to herein as vectored thermoplasty, but other terms are equally applicable, and can be used as a means for producing tissue remodeling, rejuvenation, tightening, or a desired aesthetic contour. Also one or more of these effects can be achieved by delivering energy and/or force to produce contraction in deeper tissue including facia and muscle. In a related embodiments, sufficient energy can be delivered to a selected tissue site to not only cause initial contraction of a selected muscle tissue but also reduce the excursion or range of motion of the muscle. Further descriptions of energy delivery tissue treatment for reducing muscle excursion to achieve a desire aesthetic contour or shape may be found in U.S. Provisional Application Ser. No. 60/533, 340, which is fully incorporated by reference herein.

As shown in FIG. 35, without vectored thermoplasty where the skin is not repositioned prior to energy delivery (using probe 112 or other energy delivery device means), a thermal adhesion 87 is produced at a location 90. However in FIG. 36 with vectored thermoplasty, where the skin is selectively repositioned prior to energy delivery, a thermal adhesion 87' is produced at a location 91 which serves to secure the skin at this new location. Thus the skin has been repositioned/moved a selectable distance 92 and secured in this position so as to produce a desired aesthetic effect (e.g. wrinkle reduction) or amount of tissue remodeling (e.g. face lift, eyebrow lift, jowl lift, etc). In these and related embodiments vectored thermoplasty can be used to produce the desired aesthetic effect using a combination of tissue repositioning as well as thermally induced collagen contraction and deposition by a wound healing response.

In various embodiments, tissue energy delivery with vectored force application can be performed using a surface cooled electromagnetic energy delivery device or probe that cools the skin surface and heats the subjacent dermal-subcutaneous tissues. Thus in various embodiments, apparatus 8 can include a probe 112 configured for delivering a vectored application of one or more of energy, force or cooling to a selected target site. Probe 112 can include one or more of an energy delivery device 18, a force application surface 14 and a cooling device 13. Probe 112 can also be configured to be coupled to a hand piece 11 and an energy source 22. In an embodiment, probe 112 can be template 12 described herein or another energy delivery device or dermal energy delivery device known in the art.

As shown in FIG. 36, in one embodiment of a method of vectored thermoplasty, the skin is first pulled into the desired position (e.g., 91) and then energy is delivered from probe 112 to secure the skin in the new location with thermal adhesions 87 as well as produce localized skin tightening (via collagen contractions and a subsequent wound healing response). The sequence of these steps is exemplary only and other orders are equally applicable. For example, probe 112 can be positioned before, after or while the tissue is pulled into position and can itself be used to pull the tissue.

In various embodiments one or more mechanical forces can be applied to the skin or tissue surface or selected tissue locations, before during or after the delivery of energy or other treatment by probe 112. The mechanical forces can include without limitation, compressive, tension and friction forces. The forces can be applied with selected magnitude and direction to produce a force vector. In an embodiment the applied forces can include a first force 120, having a magnitude 120m, applied in a first direction 120d and a second force 130, having a magnitude 130m, applied in a second direction 130d. In an embodiment, forces 120 and 130 can applied to act on different tissue layers (such as layers 9' and 9") so as to be mechanically independent. Alternatively, forces 120 and 130 can applied to act substantially on the same tissue so as to be additive and produce a net force 140 having a direction 140d and magnitude 140m. In various embodiments, force 130 can be applied in a range directions with respect to the direction 120*d* of force 120 including from 0 to 360° with specific embodiments of 30, 45 60 and 90°.

In one embodiment utilizing probe 112 to deliver treatment, a compressive mechanical force 120 can be applied substantially perpendicular direction 120*d* to the skin or tissue surface 9' while a second mechanical force is 130 is applied parallel or substantially parallel direction 130*d* to the skin or tissue surface. The direction 130*d* of force 130 can be substantially perpendicular to the direction 120*d* of force 120 or can otherwise be applied in a substantially tangential direction to direction 120*d*. Also, forces 120 and 130 can be applied before, during or after the delivery of treatment.

In an embodiment force 120 or 130 can be controlled to so as not to cause tearing or injury of the skin. In other embodiments, sufficient forces 120 or 130 can applied to elastically or plastically deform the skin and can be applied to be above or below skin's elastic limit (known in the biomedical engineering arts). Also, one or both of forces 120 or 130 can be varied (e.g., increased or decreased) during the course of a treatment. In various embodiments either forces 120 or 130 can have magnitudes in the range of 0.01 to 10 lbs with specific embodiments of 0.1, 0.25, 0.5, 1.0, 2.5, 5 and 7.5 lbs.

In various embodiments, the combined compression and tangential forces 120 and 130 can be applied entirely by the movement or manipulation of the probe 112. In an embodiment probe 112 can be have frictional characteristics known in the art (e.g. coefficient of friction) to be able to pull the skin or other selected tissue via the application of a frictional force. The desired frictional characteristics can be produced through the use of one or more of textures (e.g. knurled patterns), surface treatments (e.g. plasma deposition), or coatings (e.g. polymer coatings) all well known in the art.

In other embodiments forces 120 and 130 can be applied separately by applying compressive forces by the probe and manually pulling the skin in a horizontal plane. Pulling can be done using the opposite hand of the practioner or alternatively, the pulling of the skin can be done with the assistance of another practioner or using a surgical instrument or retraction instrument or device known in the art. In an embodiment shown in FIG. 37, a skin tensioning or retraction device 112*st* can be mechanically coupled to probe 112 or another energy delivery device to allow the physician to apply a force in a parallel or other direction to the skin surface. The skin surface is then moved to a more aesthetically corrected configuration and when the subjacent tissue is heated, a thermal adhesion 87 is formed in a corrected configuration between the collagen containing components of the dermis, fibrous septae and muscle fascia.

In an embodiment, all or portions of probe 112 can have a surface coating or texture 112*c* having a sufficient coefficient of friction to pull the skin via the application of a compressive force 120 from probe 112 to the skin surface as is shown in FIG. 37. Also in an embodiment, probe 112 can include a force measuring device 122 known in the art configured to determine the amount of compressive or other force applied to the skin or tissue surface. In various embodiments, force measurement device 122 can be configured to allow the monitoring and control of one or both of forces 120 and 130. In specific embodiments, measuring device 122 can be utilized to prevent or minimize tearing of the skin or control the amount of elastic or plastic deformation of the skin. Suitable force measuring devices include without limitation, strain gauges, load cells, accelerometers, solid state devices, piezoelectric sensors and devices and mems sensors and devices.

In various embodiments of vectored thermoplasty methods, energy can be applied in a desired pattern at the tissue site for example in one or more grid patterns 86 described herein.

In one embodiment, during a treatment sequence involving the multiple applications of the probe in a grid pattern, the manual pulling of the skin can be maintained throughout the entire treatment sequence. In an embodiment, to further assist the movement of the skin and subcutaneous tissues into a desired aesthetic configuration, dependant positioning of the patient during treatment can also be employed. That is, the patient can be moved or his or her limbs/extremities can be moved, before, during or after the procedure to produce a desired amount of skin movement at the tissue site. This can be facilitated by the physician applying a compressive force either by hand, or using the probe or a surgical tool, while the patient's limbs or tissues are moved.

Instead of just a two dimensional horizontal tightening of the skin from dermal collagen contraction, methods of vectored thermoplasty can employ the three dimensional heating characteristics of a volumetric electrical field 88 to form deeper subcutaneous thermal lesions 87*l*. In various embodiment lesions 87*l* can be configured as thermal adhesions 87 configured to adhere or secure tissue. In an embodiment, adhesions 87 can be configured to secure the skin and soft tissue in an aesthetically corrected configuration. In any embodiment where a thermal adhesion 87 can be employed, a thermal lesion 87*l* can also be employed.

In various embodiments, patterns of thermal adhesions can be created, for example along one or more locations on grid pattern 86, to secure skin and soft tissue in a selected configuration. In various embodiments, thermal adhesions 87 can be placed in one or more of linear, circular, square or criss-cross pattern. Thermal adhesions 87 can also be placed substantially parallel or perpendicular to force direction 120*d*.

In various embodiments, the depth, size and material characteristics of adhesions 87 can be varied by controlling the amount of energy delivery and compressive or other force 130. For example, deeper or larger adhesions can be created by the application of increased compressive forces 130. In an embodiment, a database can be developed of power settings (e.g. power or total energy delivery) and compressive forces, correlated to adhesion parameters (e.g. depth, or size). The database can be utilized to titrate the delivery of energy and force to produce a selectable adhesion depth, size or shape depending upon the procedure. Larger or deeper thermal adhesions can be used where a greater amount of securing is desired. Smaller or shaped adhesions can be used where there is less underlying tissue or in areas requiring small or precise amounts of skin repositioning and/or where it is desirable to minimize thermal injury to adjacent or nearby structures (e.g. protecting the eyes during eye lid lifts).

In various embodiments, one or more methods of the invention can be combined with a thermal skin treatment in further combination with the use of various minimally invasive aesthetic surgical procedures that use small incisions. The thermal skin treatments can include those using the Thermalcool® probe and related devices manufactured by the Thermage® Corporation (Hayward Park, Calif.). The minimally invasive procedures can include, but are not limited to, liposuction and/or flap dissection through small portal incisions instead of the larger and more extensive surgical incisions of a facelift. The portal incisions can be in the range of about 0.2 to about 2 cms, with a specific embodiment of 1 cm. The use of smaller incisions allows for the creation of a similar aesthetic effect as procedures using larger incisions, but without the more extensive and/or more visible incisions typical of larger incisions.

For ease of discussion, thermal treatments using Thermage® devices will now be referred to as Thermage treatments; however, these treatments are but an example, and all other energy treatments described herein (e.g. lasers, microwave, ultrasound and combinations therefore) are readily applicable to the following descriptions of various embodiments. In one embodiment, liposuction of the jowls and submental neck areas can be combined with Thermage treatment of these and surrounding areas. The Thermage treatments can be performed before, during or after liposuction and can include repetitive treatments to the same or surrounding areas. In use, this combination can be configured to provide more inward contouring than a Thermage treatment by itself. Also, use of Thermage treatments with liposuction can be configured to tighten the iatrogenically loosened skin envelope to a greater degree than liposuction alone. The basis for this enhanced effect is the suction skeletonization of the fibrous septae and the reduction in the soft tissue tension of these structures. As a result in these embodiments, the fibrous septae receive higher thermal doses due to higher current densities produced in these skeletonized structures (vs. surrounding tissue) and at the same time become more mechanically and thermally susceptible to thermal tightening due to collagen contraction. The overall effect is enhanced aesthetic contouring to a greater degree than if each modality were used separately.

A discussion will now be presented of tissue impedance effects. In various embodiments the tissue impedance at the tissue site can be controlled by a variety of means including, but not limited to, control of the energy delivery rate or other energy parameter described herein, or by the introduction (by injection or infusion) or evacuation of conducting and/or medicinal solutions. In various embodiments, methods described herein can be combined with a Thermage treatment and a liposuction procedure known in the art. Such liposuction procedures can involve the injection of an anesthetic solution or tumescent anesthetic solution which can include a carrier fluid. In an embodiment, the local impedance effects of the injected anesthetic solution can be minimized by evacuation of the carrier fluid of the tumescent local anesthetic in the treatment area. In various embodiments, a Thermage treatment can be performed before, during or after a liposuction or related procedure. In one embodiment, a Thermage treatment can be performed immediately following a liposuction procedure after a desired amount carrier fluid has been substantially evacuated (e.g. by a suction device or natural circulation).

A discussion will now be presented of tissue impedance and its measurement and use in RF energy control. Referring now to FIG. 38, tissue impedance can be measured using an impedance measurement monitoring device 420 which can be integral to RF generator 22 or energy source 392. In order to determine tissue impedance, a current is applied across the tissue and the resulting voltage is measured. Tissue impedance measured during an RF medical procedure is known as system impedance ($Z3$) and includes both a local impedance ($Z1$) due to the tissue impedance in the target tissue site and a bulk impedance ($Z2$) due to the electrical impedance from the rest of the body on the conductive pathway 27c to the ground pad as well as the impedance of the ground pad 19 and the RF generator and cables. Typically, $Z2$ is fixed while $Z1$ is variable, though not always. This allows for an indirect determination of local impedance by taking a baseline impedance determination (either before or at the onset of RF power delivery) and then subtracting out the baseline determination.

Tissue impedance can change during the course of a Thermage or other RF energy delivery treatment due to changes in tissue hydration, perfusion and other changes in tissue properties (e.g. fluid content, salinity, osmolality, etc.) resulting in changes in tissue conductivity. In an embodiment, impedance adjustment software utilized by the Thermage Thermacool® instrument or other software or control methods known in the art (e.g. PID algorithms) can be configured to adjust grid energy (e.g. energy delivered to a grid site 86s) in a proportionate fashion by making changes in energy parameters (e.g. power) responsive to changes in the local impedance ($Z\,1$) and not bulk impedance $Z2$. In contrast, disproportionate software adjustments of grid energy occur when changes in the system impedance ($Z\,2$) are not due to changes in the local impedance ($Z\,1$). In other embodiments, power management software can be configured to account for changes in bulk impedance, for example, due to changes in impedance at the ground pad tissue interface 19' or other locations on the body. In use, embodiments using proportionate software allow for the control of grid energies to produce a desired aesthetic effect at the tissue site while minimizing the risk of grid energies becoming too high and burning the skin at target tissue site or energies becoming too low so as to deliver a clinically ineffective thermal dose.

Figure 39A:
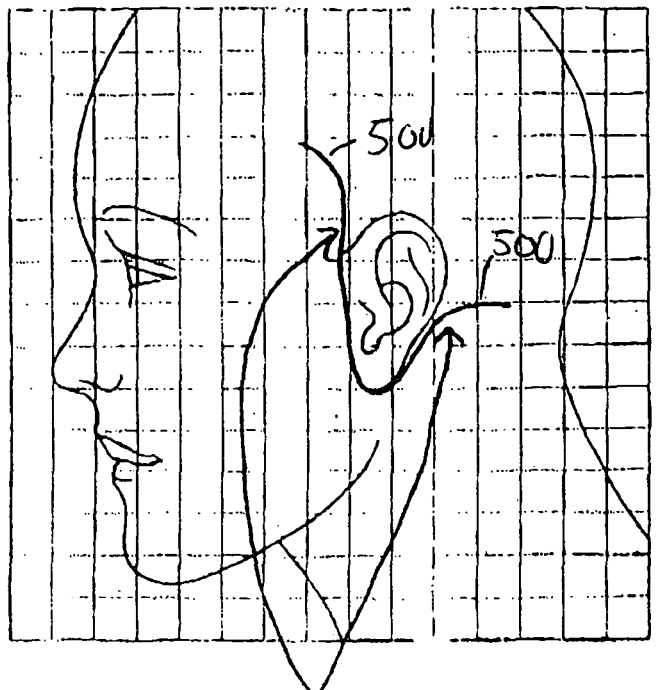
FIGS. 39a-39b are lateral views illustrating typical face lift incisions.
Figure 39B:
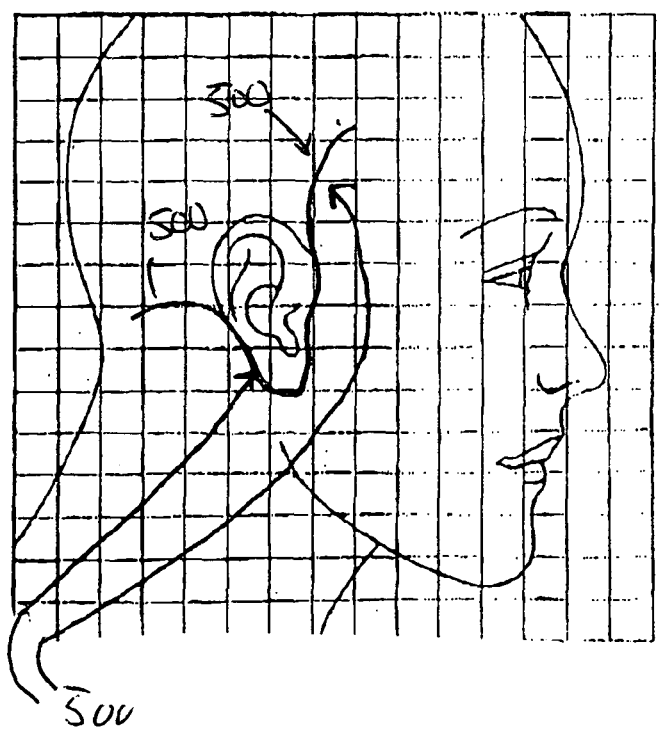
Figure 40B:
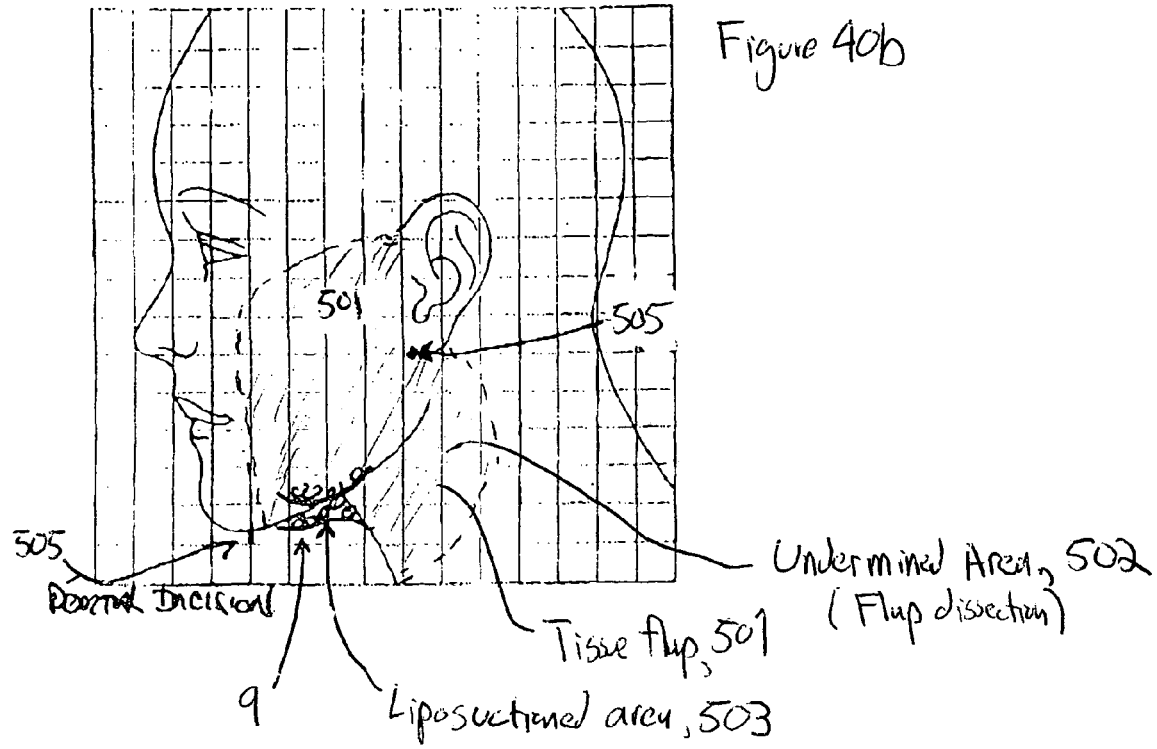
FIGS. 40a-40b are lateral views illustrating an embodiment using portal incisions to develop tissue flaps for face lifts, liposuction and related procedures.
Figure 40A:
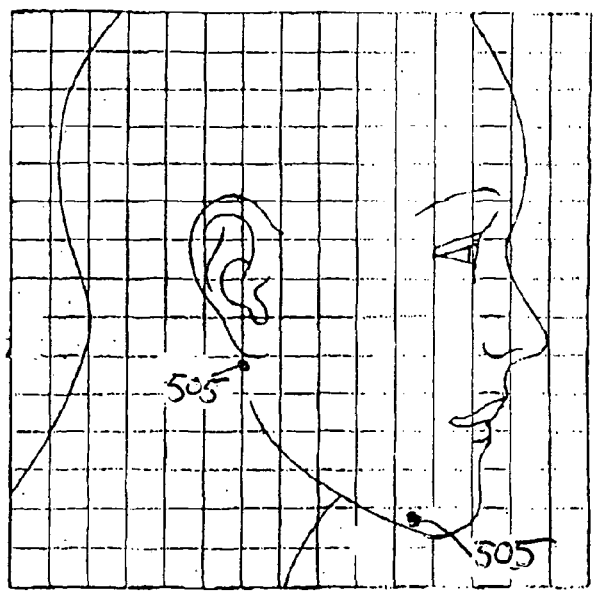

A discussion will now be presented of embodiments for performing a Thermage or other energy treatment on a dissected skin flap for face lifts and related procedures. FIGS. 39a-39b illustrate the size and shape of typical incisions 500 used for facelift and/or liposuction procedures. Referring now to FIGS. 40a-40b, these larger incisions can be substantially avoided by developing a tissue flap 501 through one or more small portal incisions 505. The flap is developed by surgically dissecting and/or undermining an area of tissue 502 through incisions 505. After development of flap 501, a selected area of tissue 503 can be liposuctioned via access through incisions 505 or other surgical incisions or access.

These and related embodiments using portal incisions, can be configured to allow for the combined use of liposuction and Thermage treatments on the face and neck to enhance the aesthetic effect of these procedures while reducing incision size. Flap dissection with transection of the fibrous septae reduces the mechanical tethering of the skin envelope in the treatment area. Consequently, energy delivery using a Thermage treatment (or other energy delivery means) on the surgically dissected skin envelope of the face, jowls and neck can be configured to produce greater amounts of thermal contraction than on un-dissected tissue. This can be achieved by applying energy directly or proximate to the dissected tissue without having intermediary layers dissipate the heat and/or mechanically constrain the target tissue. In various embodiments, minimally invasive flap dissection can be combined with Thermage treatment and/or liposuction on any number of areas of the body including but not limited to, the stomach, buttocks and thighs. In use, this combination of procedures allows for improved aesthetic outcomes (e.g. degree of skin tightening, smoothing, etc.) than could be obtained by performing the procedures individually.

In various embodiments, small incisions such as port incisions, can also be utilized to minimize the devascularization of a developed tissue flap that typically occurs during a larger face lift incision. Use of these smaller incisions, combined with the excellent circulation of the head and neck, serve to mitigate the risk of ischemic necrosis which can occur during the use of larger standard face lift incisions. In such embodiments, the incision size can be about 1 cm or less. Also the physician can utilize Doppler ultrasound or other blood flow sensing means to locate, avoid and thus, substantially preserve vasculature during one or more of a tissue dissection procedure, concomitant Thermage procedure or other energy delivery treatment.

In various embodiments, methods of the invention incorporating a Thermage treatment can be employed to treat iatrogenic laxity of skin caused by liposuction in the hips, thighs and abdomen. Treatment algorithms combining the use of Thermage treatments with liposuction can be used to counter this complication by configuring energy and/or force delivery to tighten the overlying skin envelope of the liposuction area. Such embodiments can also be used to reduce cellulite indentations of the overlying skin envelope by configuring energy and/or force delivery to produce a uniform tightening of the skeletonized fibrous septae. Selected flap dissection that transects fibrous septae will also correct cellulite in addition to promoting tightening of the skin envelope.

The creation of a thermal lesion for a desired therapeutic effect can be achieved by a number of means. In an embodiment, the creation of lesions can be facilitated by configuring energy delivery during a Thermage or other treatment to produce a delivered thermal dose that is both substantially uniform and of an amount that will result in a directed wound healing response capable of producing one or more of aesthetic contouring, tissue tightening or tissue reshaping. There are a variety of factors which may be considered in producing such a wound healing response. Such factors can include without limitation, the pattern of energy application, the pattern of force delivery and vectored pre-positioning of the tissue. In an embodiment, vectored pre-positioning of the selected tissues can be used to shape the thermal lesion so as to create or facilitate the creation of a directed wound healing response. To this end, a number of surgical techniques can be employed, including but not limited to, pre-positioning the selected tissue by hand, suturing the tissue in place, using a steri strip, using a surgical/tissue adhesive, or using a surgical clamping device known in the art.

Referring now to FIGS. 41a-41f, a discussion will now be presented of various embodiments of energy delivery methods to produce selectable lesions 87l, or adhesion 87 and subsequent aesthetic outcomes, e.g., tissue re-contouring. In one embodiment, energy can be delivered using probe 112 to create a series of discrete or semi-discrete lesions 87l or adhesions 87 to produce a desired contour 9c. However, this approach may result in contour irregularities or discontinuities 9ci caused by untreated areas or margins 9ua between or adjacent treated areas 9ta. In other embodiments, this problem can be solved by the use of a pattern or series of overlapping energy applications 93 to grid sites 86. In these embodiments, energy delivery device 18 is used to perform a series of overlapping energy applications 93 to generate a substantially continuous and uniform lesion 87u comprised of one or more lesions 87l. The amount of overlap 9o can be pre-selected or determined by assessment of the developing lesion 87u by qualitative and/or quantitative methods e.g., visual observations, palpitation, ultrasound imaging, infra-red imaging or measurements at treatment site 9. These same methods can be used to assess the uniformity of the final lesion 87u to allow re-treatment of any untreated areas 9ua which can include areas of under-treatment. In various embodiments, the amount of overlap 9o can be in the range of 1 to 99% with specific embodiments of 10, 25, 50 and 75%. Also, the amount of overlap 9o can be determined based on one or more of the following: (i) tissue characteristics (e.g., hydration levels and thickness); (ii) lesion dimensions (e.g. length and depth), and (iii) desired aesthetic outcome (e.g. amount of contouring). For example, overlap can be increased for greater amounts of contouring.

In one embodiment, a treatment algorithm uses energy delivery techniques described herein, wherein the appropriate treatment site is first selected with consideration given to avoidance of areas prone to unsightly complications. A grid pattern 86 is then marked or overlaid on the selected treatment site 9, the pattern including individual grid sites 86s. A uniform thermal dose can then be produced using multiple energy applications or passes to a grid site 86s that overlaps the margins of the grid 86m to generate a continuous or uniform lesion 87u as described above. Each application can be configured to impart a thermal dose sufficient to generate an adhesion 87 or lesion 87l which can comprise part of lesion 87u. Also, an overlapping application can be made while all or portions of an adjacent site are still hyperthermic so as to produce a cumulative heating effect in the adjacent site (e.g. due to conduction) and thus increase the total thermal dose to the entire target tissue site. This approach not only allows for increased total thermal doses to be delivered to the tissue site vs. a single treatment, but also does so while the increasing the likelihood of staying at or below the patient's pain threshold. This reduces the likelihood of procedure interruption caused by patient discomfort and/or anesthetic administration. Embodiments employing overlapping energy applications can thus be configured to provide one or more of the following: improved aesthetic outcome, more uniform thermal lesions, reduced contour irregularities, reduced contour discontinuities, reduced untreated areas, increased amounts of tissue tightening and increased thermal dosing. For thermal doses approaching or exceeding the patient's pain tolerance and/or for the anxious or pain sensitive patient, additional analgesia and sedation medication can be administered to increase the delivered energy dose.

A discussion will now be presented of thermal dosing. The adequate dose (also called a sufficient thermal dose) is configured to be sufficient to cause one or more of the following: tissue tightening, tissue remodeling or collagen contraction of at least a portion of tissue in a target tissue site. In various embodiments, the adequacy of the thermal dose can be determined using one or more of RF dose levels known in the art, a generated patient population database of RF dose levels, or database of RF dose levels developed for an individual patient or a patient group applicable (e.g. patients having sun damaged skin) to a selected patient. In an embodiment, determination of the adequacy of the thermal dose can be made by delivering energy until visible tightening of the treatment area is observed or another qualitative or quantitative indicia of tightening is observed. Such indicia can include, without limitation, skin temperature, elasticity, displacement, tension, and impedance (thermal or electrical).

The surface area in the treatment area is another factor in achieving an adequate thermal dose. Better results can be achieved with broad treatment areas that involve the face and neck rather than small treatment areas involving the face. It may be desirable to continue treatment until a visible and immediate tightening of the face and neck is apparent. In various embodiments, this can be achieved by making multiple energy applications to a treatment site such as the jowls, nasolabial folds and submentum. To avoid distraction of the tissues by gravity, in various embodiments, post-treatment support of the treatment site with a vectored compression garment can also be part of the treatment algorithm.

Figure 42:
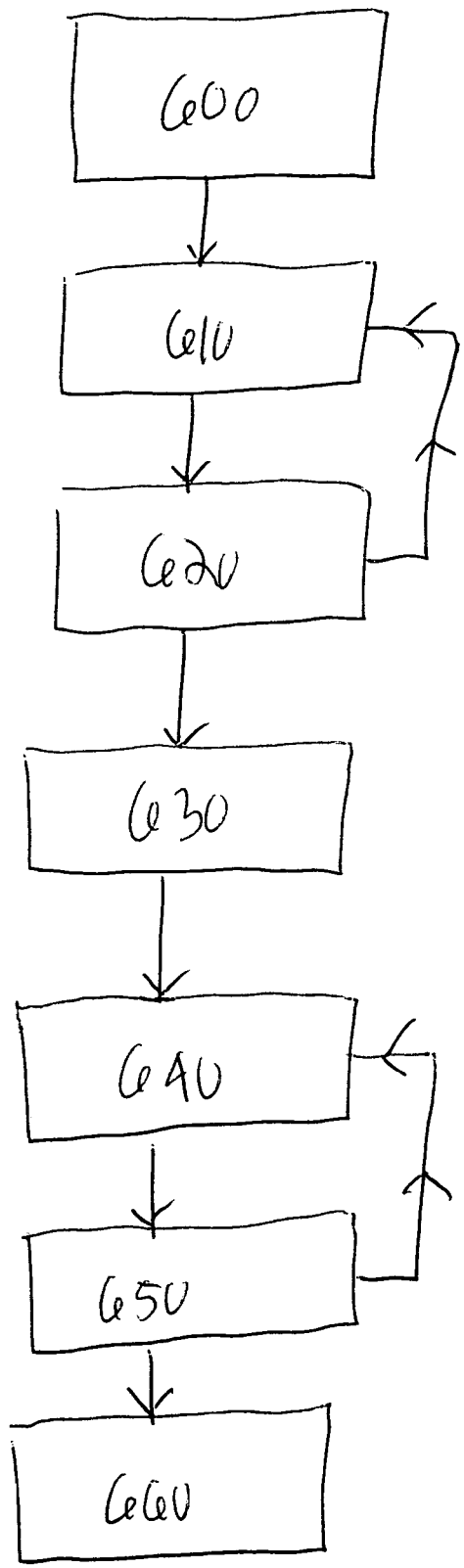
FIG. 42 is a flow chart illustrating embodiments of treatment algorithms applicable to one or methods of the invention.

A discussion will now be presented of various treatment algorithms involving combinations of treatment embodiments and/or time sequenced treatment embodiments. The order of steps in these algorithms is exemplary, and the sequence of one or more steps can be altered. As shown in FIG. 42, in an embodiment an initial energy application step 600 (which can be a series of overlapping energy applications) can be followed by a treatment evaluation step 610 where the results of the initial treatment are quantitatively and/or qualitatively evaluated, for example, using visual observation or tissue property measurement methods described herein. Based on the evaluation step 610, a re-treatment step 620 can be performed where one or more additional energy applications are made over one or more grid sites 86s to deliver additional thermal doses to those sights. The additional thermal dose can be substantially less than, equal to or greater than the initial dose. In various embodiments the additional thermal dose can be in the range of about 1 to about 500% of the initial dose with specific embodiments of 25, 50, 75, 100, 150, 250, 350 and 400% of the initial dose. The determination of the additional dose can be made on a qualitative basis such as visual observation of the degree of skin or tissue tightening at the treatment site or on a quantitative basis using measurements of skin or tissue contraction, tension, impedance, thickness, hydration and combinations thereof. After each re-treatment step 620, another evaluation step 610 can be performed with this process repeated as many times as necessary until the desired endpoint 630 is obtained (see below).

In an embodiment, treatment and re-treatment steps 600 and 620 are performed essentially during a single patient visit to produce a selected aesthetic or clinical primary endpoint 630 (e.g., 50% reduction in wrinkle depth, 25% reduction thigh diameter, raising of the eyebrow by 0.5 inch, etc.). In other embodiments, a subsequent series of time sequenced re-treatment steps 650 involving energy delivery to one or more grid sites 86s can be made days, weeks, months or years after initial treatment step. The number and time sequence of re-treatment steps 650 can be determined using a post treatment evaluation step 640 which can employ a similar method as evaluation step 620 or other evaluation methods known in the art. In various embodiments, one or more re-treatment steps 650 can be done to enhance, augment, correct or improve the outcome from endpoint 630 so as to obtain a secondary endpoint 660. After each re-treatment step 650 another evaluation step 640 can be performed until the desired endpoint 660 is obtained.

In various embodiments, a site selection algorithm can be employed to determine which area to treat and what areas to avoid. The selection algorithm can be based on visual observation as well as use of digital imaging, processing and display means such as digital maps. As will be discussed herein, in use such algorithms can provide for an improved aesthetic outcome while reducing the incidence of undesirable aesthetic outcomes due to factors such as unwanted contour reduction and accentuation of pre-existing aesthetic deformities.

A discussion will now be presented on the background on of the use of such algorithms. The broad application of a radio-frequency energy to areas such as the face and neck can produce a variety of clinical results for the aesthetic patient. For many patients the clinical aesthetic results are positive due to a generalized thermal lipolysis and wound healing response of the face and neck. However, for other patients, the results can be mixed due to an accentuation of pre-existing aesthetic deformities. Referring now to FIGS. 43a-43b, when a treatment site 9 having a substantially convex portion 109x and a substantially flat portion 109f is treated over both the convex portion and flat portion by an RF probe 112 the resulting post treatment contour 109pc can be substantially unchanged or can even become accentuated, for example more convex. For this reason, the patient selection process can be based not only on a broad generalized determination of patient suitability but also on a more selective evaluation of the localized aesthetic deformities of a particular patient, e.g. selection based on the shape and tissue properties of the deformity.

Referring now to FIG. 44, a discussion will now be presented of aesthetic deformities. Aesthetic deformities 109d can include a convex deformity 109xd, an example of which is shown in FIG. 44. Convex deformity 109xd comprises mostly a substantially convex portion 109x having convex contour 109xc. Convex deformity 109xd can have one or more adjacent flat portions 109f and can have an angle of elevation of 109ea relative to flat portion 109f. The area 109xa of deformity 109xd can be defined by a secant 109xs.

In various embodiments the treatment site 9 can be selected based on the amount of convexity of the tissue site and/or the amount of convexity of a deformity 109d at the tissue site 9. Sites to be selected can include those having a convex deformity 109xd, while sites to be avoided can include adjacent flat sites 109fs comprising mostly a substantially flat portion 109f having a substantially flat contour. In an embodiment, sites 9 having a convex contour 109xc, such as sites with a convex deformity 109xd, can be thermally treated while adjacent flat sites 109fs having substantial flat portions 109f or otherwise non convex portions can be avoided. Non-convex areas include those that are substantially flat or substantially concave.

In various embodiments the amount of convexity of site 9 and/or deformity 109d can be defined based on the angle of elevation 109ea or the ratio of secant 109xs relative to area 109xa. Accordingly in various embodiments, sites can be selected for treatment based on an amount of convexity defined by an angle of elevation 109ea in the range from about 1 to about 90° with specific embodiments having an angle of elevation 109ea greater than about 5, 10, 15, 30, 45, 60 or 75°. Alternatively, sites can be selected for treatment based on an amount of convexity defined by a ratio of secant 109xs to area 109xa in the range from about 9:10 to about 1:10 with specific embodiments of 4:5, 3:4, 2:3, 1:2, 1:3, 1:4, 1:5 and 1:9.

Referring now to FIGS. 45a and 45b a selected tissue 9 having a convex deformity 109xd and/or contour 109xc can be treated with a Thermage or other energy treatment via the application of a series/pattern of overlapping energy applications 93 confined to convex portion 109x while substantially avoiding adjacent flat portions 109f. As shown in FIG. 45b, this form of selected treatment results in the site having a post treatment contour 109pc with a substantially uniform amount of flattening and little or nor accentuation of the pretreatment contour deformity.

In various embodiments, assessment of the degree of convexity can be made visually, using mechanical or optical measurement tools known in the art, or using digital imaging, processing and/or mapping means known in the art. Examples of digital processing means can include logic resources such as one or more microprocessors. Examples of digital imaging means include any number of digital cameras known in the art.

In an embodiment, a digital image can be taken of the selected region and displayed as a digital map that is configured to highlight contours of a selectable region. Further, the digital map can be configured to highlight areas having selectable amounts of convexity. For example, areas having convexity as determined by a radius of curvature, or an amount of curvature exceeding a certain amount, could be color-coded. Further, digital processing means can contain a treatment modeling module or program, configured to calculate and display a probable post treatment contour utilizing manipulation of an initial image and inputted parameters such as selected treatment area (e.g. size and contour), tissue properties (e.g., age, skin thickness, hydration), or amount of delivered energy. The program can employ a mathematical model (e.g., a polynomial model, cubic spline, etc.) and/or finite element analysis methods to correlate thermal treatment effects (e.g. collagen tissue contraction) to these parameters and calculate and display the contour resulting from those effects. Such correlations can be established from patient populations or sub populations (e.g. elderly females with sun damage) or even from the same patient who was previously treated. The program can include graphical indications of both a predicted nominal contour and predicted contours falling within a given confidence interval (e.g. one or two standard deviations from the nominal contour) so as to account for margins of error in the model and/or computational method. In this way, a treatment modeling program can be employed by the medical practioner to improve aesthetic outcomes by seeing predicted graphical displays of those aesthetic outcomes in advance in order to facilitate determination of what tissue areas to treat and what areas to avoid.

Referring now to FIGS. 46 and 47, in various embodiments site selection methods can be used to treat aesthetic deformities 109d in the facial region, including without limitation the jowls 111, nasolabial folds 112 and the submentum 113. Selected treatment sites 9 in these areas can be selected based on the convexity of a deformity 109d and then treated using a closely overlapping pattern of energy applications 93 from a Thermage treatment until a visible clinical endpoint of contour reduction is achieved. During a treatment session, multiple passes of overlapping energy applications may also be performed to achieve a desired visible clinical endpoint (e.g. reduction in jowl area by 50% or more). Treatment of adjacent flat portions 109f of the cheeks, face and neck is substantially avoided in order to avoid reductions in contour in these areas. This approach minimizes or prevents, the accentuation of the convexity of the jowls, nasolabial folds and submentum which may occur from contour reduction in adjacent flat areas, thus resulting in an improved aesthetic outcome. For more difficult aesthetic deformities, a sequence of multiple treatments over several weeks may be performed.

In other embodiments, site selection methods can be employed to treat other areas of the body. For example, site selection methods can be used to treat deformities in the hip area such as the violin deformity of the female hip and lateral trochanteric thigh. For these and related deformities, the superior hip and lateral thigh areas can be treated but the flattened contour between the two areas is avoided. This approach produces an improved aesthetic outcome by minimizing or preventing accentuation of the violin contour of this area.

Referring now to FIGS. 48a-48e, in various embodiments the delivery of energy in a Thermage or other energy treatment can be configured to reduce convex deformities by one or more of three mechanisms. In the first mechanism shown in FIGS. 48a and 48b, energy is delivered using an RF probe to cause inward contouring (i.e. in the Z direction relative to the skin surface) of a convex deformity by thermal lipolysis of fat tissue 109ft underlying the deformity. More specifically, energy is delivered to thermally degrade or ablate a volume of fat tissue 109lv (described as lipolysis volume 109lv) underlying the deformity 109d. The destruction of the lipolysis volume 109lv serves to decrease the volume of the deformity and, in so doing, produce a flattened post treatment contour 109pc. Accordingly in this embodiment, treatment can be performed to maximize thermal lipolysis. This can be accomplished using tissue temperature and other tissue property measurements to deliver energy in a regimen (e.g. RF frequency, power and duty cycle, etc.) configured to optimize thermal lipolysis.

In the second mechanism shown in FIGS. 48c and 48d, sufficient energy is delivered using an RF probe to cause two-dimensional thermal contraction 110c (e.g., due to collagen contraction) of the section of skin 110s overlying convex deformity 109xd. The contraction decreases the length 110l and area 110a of section 110s from initial amounts of 110l1 and 110a1, to contracted amounts 110l2 and 110a2. It also increases the tension 110t in overlying skin section 110s and, in so doing, exerts a normal force 110n that acts to pull and flatten the deformity downward. Accordingly, in this embodiment, treatment can be performed to optimize skin tightening through collagen contraction and other means. This can be accomplished using tissue temperature and other tissue property measurements to deliver energy in a regimen (e.g. RF frequency, power and duty cycle, etc.) configured to maximize collagen contraction.

In the third mechanism shown in FIGS. 48e and 48f, site selection treatment methods are used to deliver, RF, or other energy, to the convex deformity 109xd employing a series of overlapping energy applications 93 substantially confined to the convex portions 109x while substantially avoiding flat portions 109f or other non convex portions. This method results in a substantially uniform post treatment contour 109pc by reducing the convexity of the convex contour 109xc over deformity 109xd while substantially not reducing the contour 109fc over flat portions 109f or other non convex portions.

In another embodiment of a treatment algorithm, the algorithm can include the use of a method or treatment plan (herein called treatment plan) determined by the condition of the patient and/or appearance of the selected tissue site, e.g., by identifying specific aesthetic deformities, such as a convex deformity. The physician can select the treatment plan based on the type and location (e.g., the face) of the deformity. Such treatments can include, without limitation, dermal treatment plans, two dimensional skin tightening plans (e.g., to treat skin redundancy), sub-dermal treatment plans and three dimensional inward contouring plans (e.g., to treat skin convex deformities).

In various embodiments, a given treatment plan can include, without limitation, the selection of one or more of the electrode size, energy delivery parameters (e.g. power levels, delivery time, etc.) and cooling parameters (e.g. pre-cooling time and cooling time). In one embodiment, the treatment plan can include identification of the deformity and then the selection of a RF electrode or electrodes to treat that particular deformity. For example, smaller electrodes (e.g., having smaller surface areas) can be used for more superficial treatments to treat skin redundancies to produce two-dimensional tightening, while larger electrodes can be used for deeper treatments to produce thermal lipolysis to treat convex deformities to produce three dimensional contouring. In various embodiments, the selected electrodes can include individual RF electrodes configured for a given energy depth (e.g. dermal, sub-dermal, etc.) or a multi-electrode comprising a matrix of joined individual electrodes configured for a given energy delivery depth. The latter embodiments are configurable to allow for more superficial treatment over a larger skin surface area.

In an embodiment, the desired treatment plan or method can be selected from a matrix of treatment plans, which can include a matrix of plans for particular skin conditions and/or deformities. For example, there can be separate treatment plans for patients with sun-damaged skin, mature skin, skin laxity, aesthetic deformities, convex aesthetic deformities, cellulite and combinations thereof. Each of these plans can include a time and dose controlled energy delivery regimen, which can be delivered in one or more treatment sessions. Also the matrix of treatment plans can be electronically stored in logic or memory resources described herein and subsequently retrieved and used to control all or a portion of a treatment session.

In various embodiments, the treatment plan can include a combination of energy treatments delivered to different tissue depths (e.g. more or less superficial). In these embodiments, both the dose and depth of energy delivery can be controlled (e.g., via control system 54 or other control means described herein). Referring back to FIG. 41e, in various embodiments energy can be delivered to different tissue depths 9td to achieve the same or different tissue effects at each depth. For example, energy can be delivered to a first tissue depth 9td1 to achieve a first tissue effect and to a second depth 9td2 to achieve a second tissue effect. In one embodiment, one energy application energy can be delivered more superficially to the dermal tissue layers to achieve dermal contraction and two dimensional tightening of the skin surface. Then in subsequent energy applications, energy can be delivered deeper to the sub-dermal layers including one or more of the subcutaneous fat layer, fibrous septae, muscle fascia and muscle. Deeper energy deliveries can be configured to achieve one or more of the following tissue effects: i) thermal contraction of one more of the fibrous septae, fascia and muscle with three dimensional deep tissue repositioning of convex aesthetic deformities; and ii) thermal lipolysis with three dimensional inward contouring of convex aesthetic deformities.

In various embodiments, the depth and/or dose of energy delivery can be controlled by a number of means. These include, without limitation, control or selection of one or more of the following: RF frequency, power levels, pre-cooling periods, size of the electrodes, energy delivery time, use of mono-polar vs. bi-polar delivery (the former producing a deeper thermal effect) and tissue hydration levels (e.g., using infusion of conductive solutions). Deeper thermal deliveries can be achieved by increasing the size of the electrodes, increased power levels, increased energy delivery times (to allow more time for thermal conduction), decreased rates of cooling, decreased pre-cooling periods (e.g. cooling prior to energy delivery) and decreased cooling periods.

EXAMPLES

Various embodiments of the invention will now be further illustrated with reference to the following examples. However, it will be appreciated that these examples are presented for purposes of illustration and the invention is not to be limited by these specific examples or the details therein.

Example I

Patient #1

This patient was a 51 year old white female that had ptosis of the eyebrows and who desired a forehead thermoplasty. After following the patient treatment algorithm (PTA) with the application of EMLA, the grid pattern was applied to the forehead. The treatment was commenced in the glabellar region of the forehead between the eyebrows. Treatment levels were titrated by using heat perception signaling by the patient. Due to the thicker tissues of the glabella, levels 14.5 to 15.0 were required to produce a level 2 heat perception signaling by the patient. The lateral aspect of the glabella required less heat energy (14.5) than the medial glabella (15.5). The thinner soft tissues of the lateral superior forehead required treatment levels to be titrated down to 13.5 because of level 3 signaling by the patient. Areas signaled as heat perception level 1 were retreated at a treatment level that produced level 2 signaling by the patient. The glabellar region received a second pass at 14.5. Pre and post treatment photos were taken as per protocol. Immediate and visible raising of the eyebrows was evident.

Example II

Patient #2

This patient was a 53 year old white female with ptosis of the eyebrows, especially in the lateral aspect. The patient had also undergone a bilateral upper blepharoplasty 3 years ago. She desired raising of her eyelids to further highlight the improvement in the appearance if her upper eyelids. Following the PTA with the application of EMLA, the grid pattern was applied to the forehead. Treatment levels were titrated up to level 14.5 in the glabella where level 2 signaling by the patient occurred. For the lateral superior forehead, titration down to 13.5 was required because of level 3 signaling by the patient. Grid areas that signaled with level 1 were retreated with treatment levels 14.5 in the glabellar region and 13.5 in the lateral superior aspect of the forehead. The photographic protocol with pre and post treatment photos was followed. The patient had moderate but demonstrable elevation of the eyebrows with improvement in the upper eyelids where a larger portion of the pretarsal segment was visible.

Example III

Patient #3

This patient was a 53 year old male who was treated in the jowl area. Following the PTA with the application of EMLA, a 1 cm grid pattern was drawn on the left cheek area including the nasolabial fold and the lateral portion of the upper lip. The inferior aspect of the grid was extended to the mandibular margin. The treat level was titrated to up to 15.5 on the inferior cheek area due to the thickness of the soft tissue. At this treatment level, patient signaling changed from a level 1 to a level 2. The superior portion of the cheek over the Zygoma and the infraorbital rim was titrated down to 14.0 to 14.5 because level 3 signaling occurred at 15.5. These tissues are significantly thinner than the lower cheek jowl area. A second pass on the jowl area was performed at 15.5. Significant demonstrable raising and flattening of the jowls, nasolabial folds with reduction of lower eyelid wrinkling was immediately evident.

Example IV

Patient #4

The patient is a 45 year old women with a thin face with minimal lipodystrophy of the cheeks, jowls and submentum but the patient has a moderate degree of skin redundancy of the cheeks and neck. A treatment plan could include treating the entire lower mid face and neck with a superficial treatment tip using overlapping applications and multiple passes as needed until tightening of the face and neck skin is visualized.

Example V

Patient #5

The patient is a 55 year old man with prominent nasolabial folds, jowls and submentum with a moderate degree of skin redundancy of the cheeks and neck. A treatment plan could include treating the nasolabial folds, jowls and submentum with a deep treatment tip and treating the entire mid lower face and neck with a superficial treatment tip. Then a pattern of closely overlapping applications and multiple passes of overlapping applications is applied until flattening of the nasolabial folds, jowls and submentum with tightening of redundant skin is visualized.

Example VI

Patient #6

The patient is a 35 year old woman with prominent nasolabial folds, jowls and submentum without a significant degree of skin redundancy of the cheeks and neck. A treatment plan could include treating the nasolabial folds, jowls and submentum with a deep treatment tip. Then a pattern of closely overlapping applications with multiple passes of overlapping applications is applied until flattening of the nasolabial folds, jowls and submentum is visualized. Treatment of the skin envelope over the nasolabial folds, jowls and submentum may also be considered.

CONCLUSION

It will be appreciated that embodiments of the invention presented herein are applicable to a wide variety of medical, dermatological and surgical procedures known in the art, including without limitation, reconstructive and plastic surgery procedures and minimally invasive procedures. It will also be appreciated that the foregoing description of various embodiments of the invention has been presented for purposes of illustration and description. It is not intended to limit the invention to the precise forms disclosed. Many modifications, variations and combinations within the scope of the invention will be apparent to practitioners skilled in the art. Also elements or acts from one embodiment can be readily substituted with elements or acts of another embodiment. Further, elements or acts from one embodiment can be readily recombined with elements or acts from other embodiments to provide further embodiments within the scope of the invention.

It is intended that the scope of the invention be defined by the following claims and their equivalents.

What is claimed is:

1. A method of treating a target tissue site, the method comprising:
   selecting the tissue site based on a tissue profile or condition of the tissue site;
   using an energy delivery device to apply a combination of electromagnetic energy treatments delivered to different tissue depths;
   delivering RF energy following a first treatment plan set for the tissue site that controls both first dose and first depth of the RF energy delivered to the tissue site in order to achieve a first tissue effect, wherein the first tissue effect is a two dimensional tightening of the tissue site;
   delivering RF energy following a second treatment plan set for the tissue site that controls both second dose and second depth of the RF energy delivered to the tissue site in order to achieve a second tissue effect, wherein the second tissue effect is a three dimensional tissue repositioning or inward contouring, wherein the first treatment plan and the second treatment plan are generated by a software program and are different from each other; and
   remodeling at least a portion of tissue at the tissue site.

2. The method of claim 1, wherein the tissue site is selected based on an amount of convexity at the tissue site or an image of the tissue site.

3. The method of claim 1, wherein at least one of the first or the second tissue effects is a thermal adhesion or lesion.

4. The method of claim 1, wherein the second tissue effect results from at least one of heating or thermal lipolysis, heating or thermal contraction of the fibrous septae, heating or thermal contraction of muscle or muscle layer, heating or thermal contraction of fascia layer, heating or thermal contraction of a ligament, heating or thermal contraction of tendons, and heating or thermal contraction of subcutaneous layer.

5. The method of claim 1, wherein the energy delivery device for delivering energy to the first or the second depth is one of an RF energy delivery device, a microwave energy delivery device, a laser or an ultrasound energy delivery device.

6. The method of claim 1, further comprising:
   producing a thermal adhesion or lesion at the tissue site; and
   remodeling at least a portion of tissue at the tissue site utilizing the thermal adhesion or lesion.

7. The method of claim 1, further comprising:
   delivering a pattern of energy applications to the tissue site using the energy delivery device; and
   producing a plurality of thermal adhesions or lesions wherein the plurality of adhesions or lesions is substantially continuous or at least partially overlapping.

8. The method of claim 1, further comprising:
   delivering a vectored force to the tissue site.

9. The method of claim 1, further comprising:
   cooling a layer of tissue or a surface layer of tissue of at least a portion of the tissue site.

10. The method of claim 1, further comprising:
    producing a reverse thermal gradient within at least a portion of the tissue site.

11. The method of claim 1, further comprising:
    producing at least one of a wound healing response or scar collagen induction within the tissue site.

12. The method of claim 1, further comprising:
    substantially preserving at least a portion of a surface, a tissue layer or an epidermal layer at or adjacent the tissue site.

13. The method of claim 1, wherein RF energy is delivered following the second treatment plan before following the first treatment plan.

14. The method of claim 1, wherein RF energy is delivered repeatedly following the first or the second treatment plans.

15. The method of claim 1, wherein the controlled first and second doses to deliver RF energy following the first and the second treatment plans are different.

16. The method of claim 1, wherein the first and the second depths to deliver RF energy are different.

17. The method of claim 16, wherein the second depth to deliver RF energy is deeper than the first depth.

18. The method of claim 1, wherein the first treatment plan delivers the RF energy to the tissue surface at the tissue site.

19. The method of claim 1, further comprising:
    evoking, initiating, and starting a wound healing response in at least one of lipolysis, heating or contraction of the fibrous septae, heating or contraction of muscle or muscle layer, heating or contraction of fascia layer, a ligament, tendons, and subcutaneous layer.

20. The method of claim 1, further comprising:
delivering a mechanical force in addition to the RF energy to reduce skin tension for the two dimensional tightening of the skin surface.

21. The method of claim 1, further comprising:
delivering a mechanical force in addition to the RF energy to place the skin surface into an anatomically corrected configuration to reduce resting skin tension.

22. The method of claim 1, further comprising:
delivering a mechanical force in addition to the RF energy to increase resting tension for two dimensional tightening or stretching of adjacent skin surface of the tissue site.

23. The method of claim 1, further comprising:
delivering a mechanical force in addition to the RF energy to apply compression for the three dimensional tissue repositioning or inward contouring.

24. The method of claim 1, further comprising:
delivering the RF energy following the first and the second treatment plans using substantially overlapping applications of the RF energy.

25. A method of treating a target tissue site, the method comprising:
identifying an aesthetic deformity at the treatment site;
choosing a plurality of treatment plans based on the aesthetic deformity, wherein the plurality of treatment plans are generated by a software program and are different from each other;
delivering RF energy following the plurality of treatment plans of application set specifically for the tissue site that controls both dose and depth of the RF energy delivered to the tissue site in order to achieve a tissue effect to correct the deformity using an energy delivery device; and
remodeling at least a portion of tissue at the tissue site.

26. The method of claim 25, wherein the aesthetic deformity is identified based on a degree of convexity, a degree of skin redundancy or an image of the treatment site.

27. The method of claim 25, wherein the tissue effect is at least one of a heating or thermal adhesion or lesion, heating or thermal lipolysis, three dimensional inward contouring of convex deformities, heating or thermal contraction of the fibrous septae, heating or thermal contraction of muscle, heating or thermal contraction of fascia, or three dimensional deep tissue repositioning of convex deformities.

28. The method of claim 25, wherein the plurality of treatment plans include a dermal treatment plan, a sub-dermal treatment plan, a two dimensional skin tightening plan or a three dimensional inward contouring plan.

29. The method of claim 25, further comprising:
controlling at least one of dose or the depth of energy delivery responsive to the identified deformity.

30. The method of claim 29, wherein the dose or depth or depth of energy delivery is controlled by at least one of the selection of electrode size, power, pre-cooling period, cooling period, or energy delivery time.

31. A method of treating a target tissue surface, the method comprising:
identifying a deformity at the tissue surface;
choosing a plurality of treatment plans based on the deformity, wherein the plurality of treatment plans are generated by a software program and are different from each other;
delivering RF energy following the plurality of treatment plans of application set specifically for the tissue site that controls both dose and depth of the RF energy delivered to the tissue surface in order to achieve a tissue effect to correct the deformity using an energy delivery device; and
remodeling at least a portion of tissue at or under the tissue surface.

32. The method of claim 31, further comprising:
minimizing electromagnetic edge effects when delivering the RF energy via an electrode by moving the electrode across skin surface.

33. The method of claim 31, further comprising:
minimizing electromagnetic edge effects when delivering the RF energy via an electrode by moving the electrode across the tissue surface.

34. The method of claim 31, further comprising:
utilizing patient feedback to reduce thermal injury to non target tissue and/or the patient's level of pain or discomfort resulting from the delivery of the RF energy to the tissue site.

35. The method of claim 31, wherein:
the tissue effect is non invasive treatment of pelvic prolapse and stress incompetence.

* * * * *